(12) United States Patent
Heintzelman et al.

(10) Patent No.: US 6,903,109 B2
(45) Date of Patent: *Jun. 7, 2005

(54) ARYLINDENOPYRIDINES AND RELATED THERAPEUTIC AND PROPHYLACTIC METHODS

(75) Inventors: Geoffrey R. Heintzelman, Annandale, NJ (US); Kristin M. Averill, High Bridge, NJ (US); John H. Dodd, Stockton, NJ (US); Keith T. Demarest, Flemington, NJ (US); Yuting Tang, Whitehouse Station, NJ (US); Paul F. Jackson, Whitehouse Station, NJ (US)

(73) Assignee: Ortho-Muniel Pharmaceutical, Inc., Raritan, NJ (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/259,139

(22) Filed: Sep. 27, 2002

(65) Prior Publication Data

US 2004/0082578 A1 Apr. 29, 2004

Related U.S. Application Data

(63) Continuation-in-part of application No. 10/123,389, filed on Apr. 16, 2002.
(60) Provisional application No. 60/284,465, filed on Apr. 18, 2001.

(51) Int. Cl.[7] .................... A61K 31/438; C07D 221/16
(52) U.S. Cl. ........................................ 514/290; 546/111
(58) Field of Search ......................... 546/111; 514/290

(56) References Cited

U.S. PATENT DOCUMENTS 6,063,788 A * 5/2000 Brandes et al. ............. 514/290

FOREIGN PATENT DOCUMENTS

| EP | 0825185 A | 2/1998 |
|---|---|---|
| EP | 0825185 A1 | 2/1998 |
| JP | 139556 A | 5/2001 |
| WO | WO 93 08167 A | 4/1993 |
| WO | WO 94/09002 A1 | 4/1994 |
| WO | WO 99/03846 A1 | 1/1999 |
| WO | WO 00/42019 A1 | 7/2000 |
| WO | WO 00/68230 A1 | 11/2000 |
| WO | WO 01/21621 A1 | 3/2001 |
| WO | WO 01 62233 A | 8/2001 |
| WO | WO 02 085894 A | 10/2002 |
| WO | WO 03 088963 A | 10/2003 |

OTHER PUBLICATIONS

Ulrich Rose, 1990, Journal of Heterocyclic Chemistry, "5–Oxo–1,4–dihydroindenopyridine: . . . ", 27(2):237–42.*
Copy of PCT International Search Report for Appln No. PCT/US02/11823 dated Aug. 27, 2002.

Afsah, E.M. et al.: "Introduction of some pharmaceuticially active heterocycles into the benzylic moiety of 2–benzyl–1, 3–indandione"; Pharmazie 45 (1990), H.4, pp. 255–257.
Ascherio, A. et al: "Prospective Study of Caffeine Consumption and Risk of Parkinson's Diesease in Men and Women"; Annals of Neurology, 2001, 50, pp. 56–63.
Bocker, R.H. et al.: "Oxidation of 4–Aryl–and 4–AlkylSubstituted 2,6–Dimethyl–3,5–bis(alkoxycarbonyl)–1,4–dihydropyridines by Human Liver Microsomes and Immunochemical Evidence for the Involvement of a Form of Cytochrome P–450"; J. Med. Chem. 1986, 29, pp. 1596–1603.
Bradley, G. et al.: "2,3–Dihydroquinolin–4(1H)–ones. Part I. Halogen–substituted 2,3–Dihydroquinolin–4(1H)–ones and their 1–(2–Acylethyl) Derivatives"; J. Chem. Soc., Perkin Trans. 1, 1972, pp 2019–2023.
Bullington, J.L. et al.: "The Development of NOvel and Selective p56lck Tyrosine Kinase Inhibitors[1]"; Bioorg. Med. Chem. Lett. 1998, 8, pp. 2489–2494.
Chatterjea, J.N. et al.; "Synthesis in the 4–Azafluorene Group. Part III"; J. Indian Chem. Soc., vol. LV, 1978, pp. 149–153.
Chen, J.F. et al.: "Neuroprotection of Caffeine and $A_{2A}$ Adenosine Receptor Inactivation in a Model of Parkinson's Disease"; J. of Neuroscience, 2001, vol. 21 RC143, pp. 1–6.
Chen, W. et al.: "A Colorimetric Assay for Measuring Activation of $G_s$–$G_q$–Coupled Signaling Pathways"; Analytical Biochemistry, 1995, 226, pp. 349–354.
Ferre, S. et al.: "Stimulation of high–affinity adenosine $A_2$ receptors decreases the affinity of dopamine $D_2$ receptors in rat striatal membranes"; Proceedings of the Nat'l Academy of Sciences of the USA, 1991, 88, pp. 7238–7241.
Fink, J.S. et al.: "Molecular cloning of the rat $A_2$ adenosine receptor: selective co–expression with $D_2$ dopamine receptors in rat striatum"; Molecular Brain Research, 14 (1992), pp. 186–195.

(Continued)

Primary Examiner—Joseph Mckane
Assistant Examiner—Robert Shiao
(74) Attorney, Agent, or Firm—Peter L. Herridge

(57) ABSTRACT

This invention provides novel arylindenopyridines of the formula:

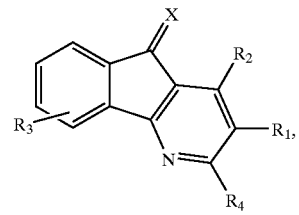

and pharmaceutical compositions comprising same, useful for treating disorders ameliorated by antagonizing Adensine A2a receptors or reducing PDE activity in appropriate cells. This invention also provides therapeutic and prophylactic methods using the instant pharmaceutical compositions.

24 Claims, No Drawings

OTHER PUBLICATIONS

Gessi, S. et al.: "$A_{2A}$ adenosine receptors in human peripheral blood cells"; British J. of Pharm., 2000, 129, pp. 2–11.

Gorlitzer, K. et al.: "Indeno[1,2-b]pyridin-4-yl-amine[3]"; Pharmazie 52 (1997) 7, pp. 504–510.

Ikeda, K. et al.: "Neuroprotection by adenosine $A_{2A}$ receptor blockade in experimental models of Parkinson's disease"; J. of Neurochemistry, 2002, 80, pp. 262–270.

Impagnatiello, F. et al.: "Adenosine receptors in neurological disorders"; Emerging Therapeutic Targets, 2000, 4, pp. 635–664.

Jursic, B.S. et al.: "A Simple Preparation of Amides from Acids and Amines by Heating of their Mixture"; Synthetic Comm. 1993, 23, pp. 2761–2770.

Kobayashi, T. et al: "Novel 2–Amino–1,4–dihydropyridine Calcium Antagonists. I. Synthesis and Antihypertensive Effects of 2–Amio–1,4–dihydropyridine Derivatives Having Nitroxyalkoxycarbonyl Groups at 3– and/or 5–Position"; Chem. Pharm. Bull. 1995, 43, pp. 788–796.

Li, L. et al.: "CD3– and CD28–Dependent Induction of PDE7 Required for T Cell Activation"; Science, 1999, vol. 283, pp. 848–851.

Lusis, V. et al.: "Synthesis and Isomerization of 1H–4,4a,5,9b–Tetrahydroindeno–[1,2–b]pyridines"; Tetrahedron, 1991, vol. 47, No. 35, pp. 7429–7436.

Mally, J. et al.: "Efficacy of an adenosine antagonist, theophylline, in essential tremor: comparison with placebo and propranolol"; J. of the Neurological Sciences, 1995, 132, pp. 129–132.

Martinez, A. et al.: "Benzyl Derivatives of 2,1,3–Benzo– and Benzothieno[3,2–a]thiadiazine 2,2–Dioxides: First Phosphodiesterase 7 Inhibitors"; J. Med. Chem. 2000, 43, pp. 683–689.

Ogawa, T. et al.: Synthesis and Configurational Assignment of Methyl 3–Nitrooxypropyl 1,4–Dihydro–2,6–dimethyl–4–(3–nitrophenyl)pyridine–3,5–dicarboxylate; J. Chem. Soc. Perkin Trans 1, 1993, pp. 525–528.

Omuaru, V.O.T.: "Reactions of cyclic anhydrides with aromatic primary amines: Part 3—Synthesis of novel 3–(N–arylcarbamoyl)–and 3–(N–naphthylcarbamoyl)carboxylic acids"; Indian J. of Chem., 1998, vol. 37B pp. 814–816.

Petrow, V. et al.: "New Syntheses of Heterocyclic Compounds. Part X. 4–Azafluorenones"; JCS, 1949, pp. 2134–2139.

Reddy, A.S. et al.: "A convenient method for the preparation of hydroxamic acids"; Tetrahedron Letters 41 (2000), pp. 6285–6288.

Rose, U.: "5–Oxo–1,4–dihydroindenopyridines: Calcium Modulators with Partial Calcium Agonistic Activity"; J. Heterocyclic Chem., 27, (1990), pp. 237–242.

Rosin, D.L. et al.: "Immunohistochemical Localization of Adenosine $A_{2A}$ Receptors in the Rat Central Nervous System"; The J. of Comparative Neurology, 1998, 401, pp. 163–186.

Salim, H. et al.: "Activation of Adenosine $A_1$ and $A_{2A}$ Receptors Modulates Dopamine $D_2$ Receptor–Induced Responses in Stably Transfected Human Neuroblastoma Cells"; J. of Neurochemistry, 2000, 74, pp. 432–439.

Sausin'sh, A. et al.: "Methods for the Synthesis of 4–Pyrazolyl– and 4–Pyridyl–5–Oxo–1,4,5,7–Tetrahydrofuro[3,4–b]Pyridines"; Chem. of Heterocyclic Compounds, vol. 31, No. 7, 1995, pp. 841–846.

Stiles, G. et al.: "Adenosine Receptors"; The J. of Biological Chem., 1992, vol. 267 No. 10, pp. 6451–6454.

Vanden Eynde, JJ. et al.: "Old Reagents, New Results: Aromatization of Hantzsch 1,4–Dihydropyridines with Manganese Dioxide and 2,3–Dichloro–5,6–dicyano–1,4–benzoquinone."; Tetrahedron, 1995, vol. 51, No. 23, pp. 6511–6516.

Varani, K. et al.: "Pharmacological and biochemical characterization of purified $A_{2a}$ adenosine receptors in human platelet membranes by [$^3$H]–CGS 21680 binding"; British J. of Pharmacology, 1996, 117, pp. 1693–1701.

Vigante, B. et al.: Latv. PSR Zinat. Akad. Vestis, Kin. Ser. 1980, pp. 707–715.

Vigante, B.A. et al.: "Infrared Absorption of 4,5–Dihydroindeno[1,2–b]Pyridines"; Chem. Het. Compounds, 25(5) 1989, pp. 524–527.

Weissman, S.A. et al.: "Efficient Synthesis of N–Arylpiperazinones via a Selective Intramolecular Mitsunobu Cyclodehydration"; Tetrehedron Lett. 1998, 39, pp. 7459–7462.

Zandersons, A.Z. et al.: Synthesis of 5–Oxoindeno[1,2–b] Pyridinium Salts; Chem. Het. Compounds 22(1), 1986, pp. 73–76.

Zimmer, H. et al.: Substituted y–Lactones. 28.[1] 3–(Phenylmethylene)2–3,4(3H,5H)–furandiones.; J. Org. Chem. vol. 43, No. 8, 1978, pp. 1541–1544.

Chemical Abstracts, vol. 59, No. 6, Sep. 16, 1963; XP–002211132.

Copy of PCT International Search Report for Appln No. PCT/US02/30825 dated Nov. 25, 2002.

Database CHEMCATS 'Online' (Feb. 11, 2002), Interbioscreen Compound Library: 2002:3027027, XP002220645.

Database CHEMCATS 'Online' (Jan. 21, 2002), Ambinter: Exploratory Library: 2002:2845045, 2002: XP002220646.

Database CHEMCATS 'Online' (Jan. 21, 2002), Ambinter: Exploratory Library: 2002:1552297, XP002220647.

Database CHEMCATS 'Online' (Jan. 15, 2002), Bionet Research: 2001:2494341, 2001:2494321, XP002220648.

Database CHEMCATS 'Online' (Jul. 1, 2001), Compounds for Screening: 2001:1603530, XP002220649.

Database CA 'Online' Chemical Abstracts Service, Columbus, OH, US; Kandeel, Ez–El–Din M.: "Synthesis of some new functionalized pyridines, 5–oxoindeno'1, 2–b!pyridines and related compounds of potential pharmaceutical interest" 136:200063 XP002220650 abstract & Mansura Science Bulletin, A; Chemistry (2000), 27(2), 35–49.

Database CA 'Online' Chemical Abstracts Service, Columbus, OH, US; Sausins, A. et al: "Methods of synthesis of 4–(pyridyl)–5–oxo–1, 4, 5, 7–tetrehyrofuro'3, 4–b!pyridines" 124:202067 XP002220651 & Khimiya Geterotsiklicheskikh Soedinenii (1995), (7), 966–72.

Database CA 'Online' Chemical Abstracts Service, Columbus, OH, US; Geies, Ahmed A. et al.: "Synthesis of indeno'1, 2–b!pyridines and indeno'1, 2–b!thieno'3, 2–e!pyridines" 128:244011 XP002220652 & Bulletin of the Polish Academy of Sciences, Chemistry (1997), 45(4), 381–390, 2 plates.

Database CA 'Online' Chemical Abstracts Service, Columbus, OH, US; Lusis, V. et al: "Synthesis and isomerization of 1H–4, 4a, 5, 9b–tetrahydroindeno'1, 2–b!pyridines" 116:20903 XP 002220653 & Tetrahedron (1991), 47(35), 7429–36.

Database CA 'Online' Chemical Abstracts Service, Columbus, OH, US; Zandersons, A. et al: "Synthesis of substituted 5–oxoindeno'1, 2–b!pyridinium salts" 105:208733 XP002220654 & Khimiya Geterotsiklicheskikh Soedinenii (1986), (1), 88–90.

Database CA 'Online' Chemical Abstracts Service, Columbus, OH, US; Stankevich, E. et al: "Polynuclear heterocyclic compounds, XIII. New derivatives of 9, 11–dioxo–10–phenyl–11H–indeno'1, 2–b!tetrahydroquinoline" 59:35503 XP002220655 & Latvijas Psr Zinatnu Akad. Vestis, Kim. Ser. (1962), (No. 2), 283–6.

Database CA 'Online' Chemical Abstracts Service, Columbus, OH, US; Vanags, G. et al: "Polynuclear heterocyclic compounds. VI. 4, 6 –Diphenyl—2, 3—(CO)—benzoylenepyridine" 58:14816 XP002220656 & Zh. Obshch. Khim. (1962), 32, 1151–9.

Database CA 'Online' Chemical Abstracts Service, Columbus, OH, Vigante, B. et al: "Ethyl esters of 1, 4–dihydropyridine–3, 5–di– and 2–methyl–4–aryl–5oxo–4, 5 dihydro–1H–indeno'1, 2–b!pyridine–3–carbothionic acids" 101:6372 XP002220657 & Khim. Geterotsikl. Soedin. (1984), (2), 210–16.

Database CA 'Online' Chemical Abstracts Service, Columbus, OH, Vigante, B. et al: "Infrared absorption of 4, 5–dihydroindeno'1, 2–b!pyridines" 112:97907 XP002220658 & Khimiya Geterotsiklicheskikh Soedinenii (1989), (5), 629–32.

Database CA 'Online' Chemical Abstracts Service, Columbus, OH, Zandersons, A. et al: "Synthesis of substituted 5–oxoindeno'1, 2–b!pyridinium salts" 105:208733 XP002220659 & Khimiya Geterotsiklicheskikh Soedinenii (1986), (1), 88–90.

Database CA 'Online' Chemical Abstracts Service, Columbus, OH, Vigante, B. et al: "Synthesis and properties of 5–oxo–1, 4–dihydroindeno'1, 2–b!pyridine–3–casbothiolic acid esters" 95:7009 XP002220660 & Latv. Psr Zinat. Akad. Vestis, Kim. Ser. (1980), (6), 707–16.

Database CA 'Online' Chemical Abstracts Service, Columbus, OH, Mucsenietce, D. et al: "Reduction and basic hydrolysis of 5–oxoindeno'1, 2–b!pyridinium salts" 107:236463 XP002220661 & Khimiya Geterotsiklicheskikh Soedinenii (1987), (1), 86–9.

Database CA 'Online' Chemical Abstracts Service, Columbus, OH, Zandersons, A. et al: "Synthesis of substituted 5–oxoindeno'1, 2–b!pyridinium salts" 105:208733 XP002220662 & Khimiya Geterotsiklicheskikh Soedinenii (1986), (1), 88–90.

Goerlitzer, K. et al: "Indeno(1,2–b)pyridin–4–yl–amine" Pharmazie, vol. 52, No. 7, 1997, pp. 504–510, XP002211131 ISSN: 0031–7144 cited in the application p. 506; compounds of formulae 8b–10b compounds excluded by proviso.

Database CHEMCATS 'Online' (Jul. 9, 2002) Interchim Intermediats: 2002:2525250 and other XP002220663.

Database CHEMCATS 'Online' (Jul. 9, 2002) Interchim Intermediats: 2002:2403473,–3487,–3488,–3489 and 2002:2548348 XP002220664.

Database CHEMCATS 'Online' (Jul. 9, 2002) Interchim Intermediats: 2002:3011492 to 2002:3011513 XP002220665.

El–Tawell F. M. A. et al.: "Synthetic Routes to Fluorenone, Indenopyirdine, 4H–NaphthoA2, 1–Bupyrans and Pyridine Derivaties", Bolettino Chimico Farmaceutico, Societa Editoriale Farmacautica, Milano, Italy, vol. 140, No. 5, 2001, pp. 306–310, XP009025181, ISSN: 0008–8848 See compound 14.

Goerlitzer K. et al.: "IndenoA1, 1–Dupyrimidin–4–YL–Amine IndenoA1, 2Upyrimidin–4–YL–Amines" Pharmazle, Veb Verlag Volk Und Gesundheit. Berlin, DD vol. 52, No. 9, 1997 pp. 670–672, XP001179310, ISSN: 0031–7144 see compounds 3, 6–8 and whole article, especially 2.2.1.

Burger K. et al. "Trifluormethyl–Substituierte Pyrimidine Aus Enaminen Und Trifluoracetonitril TrifluoromethylSubstituted Pyramidines from Enamines and Trifluoroacetonitrile" Liabigs Annatan Der Chemia, Verlag Chemia GmbH Weinheim, DE, vol. 5, 1984, pp. 991–1002 XP001179309 ISSN: 0170–2041 see compund 18a.

Dermerac S. et al., "6H–IndenoA1, 2–Dupyrumidin–5–Ones" Austrailian Journal of Chemistry, XX, XX, vol. 25, 1972, pp. 2651–2657, XP009025111 issn: 0004–9425 see compounds 5a–5e and 9–11.

Augustin, M.: "Synthese und Reaktionen von 2–ABIS-(Alklthio)–Methylidenu–Indan–1,3–Dionen Synthesis and Reactions of 2–Abis–(Alkylthio)–Methlidenu–Indan–1,3–Dion", Journal Fuer Praktische Chemia, Wiley Wein Heim, DE, vol. 321, No. 2, 1979, pp. 205–214, XP009025100, ISSN: 1436–9966, see 11b, p. 212 and 11c, p213.

N El–Rayyes; "Heterocycles. 14. Synthesis of 5H–Indenopyrumidines" J. Chem. Eng. Data, vol. 32, 1987, pp. 481–483, XP002270517 see formula VII, f, h,j, Va–k.

Kappe C. O. et al. 'Synthesis and Reactions of Biginelli-Compounds. Part I' Journal of Heterocyclic Chemistry, Heterocorporation Provo, US, Jan. 1989 (1989–01), pp. 55–64, XP002952094, ISSN: 00220152X, see compound 29a.

A. Rosowsky; 'One Step Synthesis of Nove 2, 4–Diaminopyrumudube Antifolates' J. Heterocyclcl Chemistry vol. 38, 1999, pp. 723–728, XP002270518 see 20(14).

Kandeel, E.M. et al.: "Synthesis of New 1, 2–Dihydro–4–Amino–2–Thioxo–5H–Indend 1, 2–D Pyrimidin–5–One Derivaties" Pakistan Journal of Scientific and Industrial Research, XX, XX, vol. 29, No. 6, Dec. 1988 (1988–12) pp. 424–426, XP009025187 ISSN: 0030–9885 see V1a, V1b, Va, Vb.

PCT Search Report dated Jan. 3, 2004, for PCT Appl. No. PCT/US03/31471.

* cited by examiner

ARYLINDENOPYRIDINES AND RELATED THERAPEUTIC AND PROPHYLACTIC METHODS

CROSS-REFERENCE TO RELATED APPLICATIONS

This application is a continuation-in-part of co-pending application Ser. No. 10/123,389, filed on Apr. 16, 2002, which claims the benefit of Provisional application Ser. No. 60/284,465 filed Apr. 18, 2001, which are incorporated herein by reference.

FIELD OF THE INVENTION

This invention relates to novel arylindenopyridines and their therapeutic and prophylactic uses. Disorders treated and/or prevented using these compounds include neurodegenerative and movement disorders ameliorated by antagonizing Adenosine A2a receptors and inflammatory and AIDS-related disorders ameliorated by inhibiting phosphodiesterace activity.

BACKGROUND OF THE INVENTION
Adenosine A2a Receptors

Adenosine is a purine nucleotide produced by all metabolically active cells within the body. Adenosine exerts its effects via four subtypes of cell-surface receptors (A1, A2a, A2b and A3), which belong to the G protein coupled receptor superfamily (Stiles, G. L. Journal of Biological Chemistry, 1992, 267, 6451). A1 and A3 couple to inhibitory G protein, while A2a and A2b couple to stimulatory G protein. A2a receptors are mainly found in the brain, both in neurons and glial cells (highest level in the striatum and nucleus accumbens, moderate to high level in olfactory tubercle, hypothalamus, and hippocampus etc. regions) (Rosin, D. L.; Robeva, A.; Woodard, R. L.; Guyenet, P. G.; Linden, J. Journal of Comparative Neurology, 1998, 401, 163).

In peripheral tissues, A2a receptors are found in platelets, neutrophils, vascular smooth muscle and endothelium (Gessi, S.; Varani, K.; Merighi, S.; Ongini, E.; Borea, P. A. British Journal of Pharmacology, 2000, 129, 2). The striatum is the main brain region for the regulation of motor activity, particularly through its innervation from dopaminergic neurons originating in the substantia nigra. The striatum is the major target of the dopaminergic neuron degeneration in patients with Parkinson's Disease (PD). Within the striatum, A2a receptors are co-localized with dopamine D2 receptors, suggesting an important site of for the integration of adenosine and dopamine signaling in the brain (Fink, J. S.; Weaver, D. R.; Rivkees, S. A.; Peterfreund, R. A.; Pollack, A. E.; Adler, E. M.; Reppert, S. M. Brain Research Molecular Brain Research, 1992, 14, 186).

Neurochemical studies have-shown that activation of A2a receptors reduces the binding affinity of D2 agonist to their receptors. This D2R and A2aR receptor-receptor interaction has been demonstrated in striatal membrane preparations of rats (Ferre, S.; von Euler, G.; Johansson, B.; Fredholm, B. B.; Fuxe, K. Proceedings of the National Academy of Sciences of the United States of America, 1991, 88, 7238) as well as in fibroblast cell lines after transfected with A2aR and D2R cDNAs (Salim, H.; Ferre, S.; Dalal, A.; Peterfreund, R. A.; Fuxe, K.; Vincent, J. D.; Lledo, P. M. Journal of Neurochemistry, 2000, 74, 432). In vivo, pharmacological blockade of A2a receptors using A2a antagonist leads to beneficial effects in dopaminergic neurotoxin MPTP (1-methyl-4-pheny-l,2,3,6-tetrahydropyridine)-induced PD in various species, including mice, rats, and monkeys (Ikeda, K.; Kurokawa, M.; Aoyama, S.; Kuwana, Y. Journal of Neurochemistry, 2002, 80, 262). Furthermore, A2a knockout mice with genetic blockade of A2a function have been found to be less sensitive to motor impairment and neurochemical changes when they were exposed to neurotoxin MPTP (Chen, J. F.; Xu, K,; Petzer, J. P.; Staal, R.; Xu, Y. H.; Beilstein, M.; Sonsalla, P. K.; Castagnoli, K.; Castagnoli, N., Jr.; Schwarzschild, M. A. Journal of Neuroscience, 2001, 21, RC143).

In humans, the adenosine receptor antagonist theophylline has been found to produce beneficial effects in PD patients (Mally, J.; Stone, T. W. Journal of the Neurological Sciences, 1995, 132, 129). Consistently, recent epidemiological study has shown that high caffeine consumption makes people less likely to develop PD (Ascherio, A.; Zhang, S. M.; Hernan, M. A.; Kawachi, I.; Colditz, G. A.; Sp izer, F. E.; Willett, W. C. Annals of Neurology, 2001, 50, 56). In summary, adenosine A2a receptor blockers may provide a new class of antiparkinsonian agents (Impagnatiello, F.; Bastia, E.; Ongini, E.; Monopoli, A. Emerging Therapeutic Targets, 2000, 4, 635).

Phosphodiesterase Inhibitors

There are eleven known families of phosphodiesterases (PDE) widely distributed in many cell types and tissues. In their nomenclature, the number indicating the family is followed by a capital letter that indicates a distinct gene. A PDE inhibitor increases the concentration of CAMP in tissue cells, and hence, is useful in the prophylaxis or treatment of various diseases caused by the decrease in cAMP level which is induced by the abnormal metabolism of CAMP. These diseases include conditions such as hypersensitivity, allergy, arthritis, asthma, bee sting, animal bite, bronchospasm, dysmenorrhea, esophageal spasm, glaucoma, premature labor, a urinary tract disorder, inflammatory bowel disease, stroke, erectile dysfunction, HIV/AIDS, cardiovascular disease, gastrointestinal motility disorder, and psoriasis.

Among known phosphodiesterases today, PDE1 family are activated by calcium-calmodulin; its members include PDE1A and PDE1B, which preferentially hydrolyze cGMP, and PDE1C which exhibits a high affinity for both CAMP and cGMP. PDE2 family is characterized as being specifically stimulated by cGMP. PDE2A is specifically inhibited by erythro-9(2-hydroxy-3-nonyl)adenine (EHNA). Enzymes in the PDE3 family (e.g. PDE3A, PDE3B) are specifically inhibited by cGMP. PDE4 (e.g. PDE4A, PDE4B, PDE4C, PDE4D) is a cAMP specific PDE present in T-cells, which is involved in inflammatory responses. A PDE3 and/or PDE4 inhibitor would be predicted to have utility in the following disorders: autoimmune disorders (e.g. arthritis), inflammatory bowel disease, bronchial disorders (e.g. asthma), HIV/AIDS, and psoriasis. A PDE5 (e.g. PDE5A) inhibitor would be useful for the treatment of the following disorders: cardiovascular disease and erectile dysfunction. The photoreceptor PDE6 (e.g. PDE6A, PDE6B, PDE6C) enzymes specifically hydrolyze cGMP. PDE8 family exhibits high affinity for hydrolysis of both cAMP and cGMP but relatively low sensitivity to enzyme inhibitors specific for other PDE families.

Phosphodiesterase 7 (PDE7A, PDE7B) is a cyclic nucleotide phosphodiesterase that is specific for cyclic adenosine monophosphate (cAMP). PDE7 catalyzes the conversion of cAMP to adenosine monophosphate (AMP) by hydrolyzing the 3'-phosphodiester bond of cAMP. By regulating this conversion, PDE7 allows for non-uniform intracellular distribution of cAMP and thus controls the activation of distinct kinase signalling pathways. PDE7A is primarily expressed in T-cells, and it has been shown that induction of PDE7A is required for T-cell activation (Li, L.; Yee, C.; Beavo, J. A. *Science* 1999, 283, 848). Since PDE7A activation is necessary for T-cell activation, small molecule inhibitors of PDE7 would be useful as immunosuppressants. An inhibitor of PDE7A would be predicted to have immunosuppressive effects with utility in therapeutic areas such as organ transplantation, autoimmune disorders (e.g. arthritis), HIV/AIDS, inflammatory bowel disease, asthma, allergies and psoriasis.

Few potent inhibitors of PDE7 have been reported. Most inhibitors of other phosphodiesterases have $IC_{50}$'s for PDE7 in the 100 μM range. Recently, Martinez, et a/. (*J. Med. Chem.* 2000, 43, 683) reported a series of PDE7 inhibitors, among which the two best compounds have PDE7 $IC_{50}$'s of 8 and 13 μM. However, these compounds were only 2–3 times selective for PDE7 over PDE4 and PDE3.

Finally the following compounds have been disclosed, and some of them are reported to show antimicrobial activity against strains such as *Plasmodium falciparum, Candida albicans* and *Staphylococcus aureus* (Gorlitzer, K.; Herbig, S.; Walter, R. D. *Pharmazie* 1997, 504):

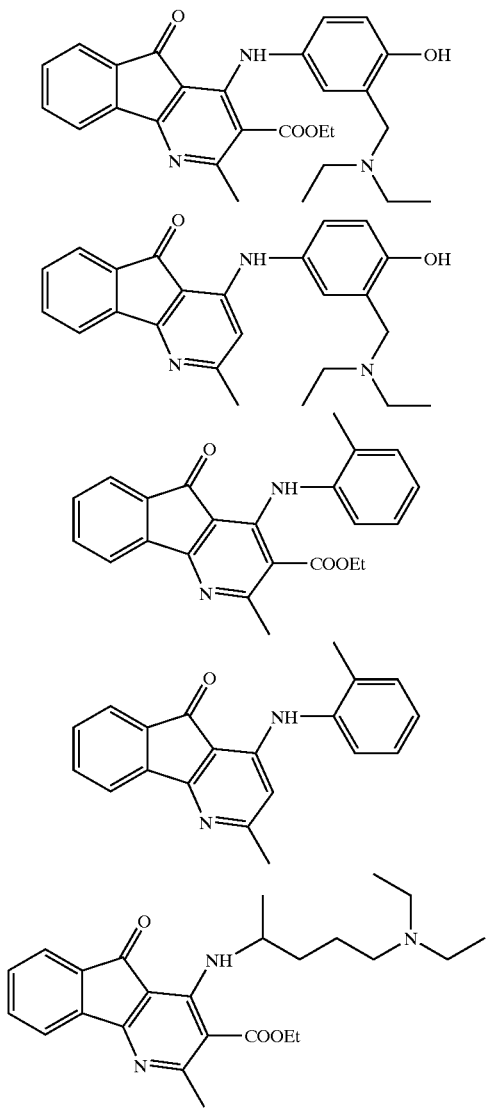

-continued

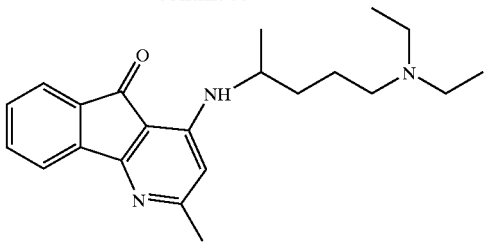

SUMMARY OF THE INVENTION

This invention provides a compound having the structure of Formula I

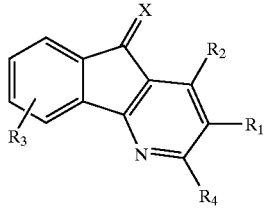

Formula I or a pharmaceutically acceptable salt thereof, wherein (a) $R_1$ is selected from the group consisting of:
  (i) —$COR_5$, wherein $R_5$ is selected from H, optionally substituted $C_{1-8}$ straight or branched chain alkyl, optionally substituted aryl and optionally substituted arylalkyl;
  wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, aryl, or heteroaryl or $NR_{20}R_{21}$ taken together form a heterocycle or heteroaryl;
  (ii) $COOR_6$, wherein $R_6$ is selected from H, optionally substituted $C_{1-8}$ straight or branched chain alkyl, optionally substituted aryl and optionally substituted arylalkyl;
  wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, aryl, or heteroaryl or $NR_{20}R_{21}$ taken together form a heterocycle or heteroaryl;
  (iii) cyano;
  (iv) a lactone or lactam formed with $R_4$;
  (v) —$CONR_7R_8$ wherein $R_7$ and $R_8$ are independently selected from H, $C_{1-8}$ straight or branched chain alkyl, $C_{3-7}$ cycloalkyl, trifluoromethyl, hydroxy, alkoxy, acyl, alkylcarbonyl, carboxyl, arylalkyl, aryl, heteroaryl and heterocyclyl;
  wherein the alkyl, cycloalkyl, alkoxy, acyl, alkylcarbonyl, carboxyl, arylalkyl, aryl, heteroaryl and heterocyclyl groups may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy or arylalkyl, or $R_7$ and $R_8$ taken together with the nitrogen to which they are attached form a heterocycle or heteroaryl group;

(vi) a carboxylic ester or carboxylic acid bioisostere including optionally substituted heteroaryl groups (b) $R_2$ is selected from the group consisting of optionally substituted alkyl, optionally substituted aryl, optionally substituted heteroaryl, optionally substituted heterocyclyl and optionally substituted $C_{3-7}$ cycloalkyl;

(c) $R_3$ is from one to four groups independently selected from the group consisting of:

(i) hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, aryl, heteroaryl, and heterocyclyl;

(ii) '$NR_{12}R_{11}$ wherein $R_{10}$ and $R_{11}$ are independently selected from H, $C_{1-8}$ straight or branched chain alkyl, arylalkyl, $C_{3-7}$ cycloalkyl, carboxyalkyl, aryl, heteroaryl, and heterocyclyl or $R_{10}$ and $R_{11}$ taken together with the nitrogen form a heteroaryl or heterocyclyl group;

(iii) —$NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxyalkyl, $R_{30}R_{31}N(CH_2)_p$—, $R_{30}R_{31}NCO(CH_2)_p$—, aryl, arylalkyl, heteroaryl and heterocyclyl or $R_{12}$ and $R_{13}$ taken together with the carbonyl form a carbonyl containing heterocyclyl group, wherein, $R_{30}$ and $R_{31}$ are independently selected from H, OH, alkyl, and alkoxy, and p is an integer from 1–6, wherein the alkyl group may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy or arylalkyl;

(d) $R_4$ is selected from the group consisting of (i) hydrogen, (ii) $C_{1-3}$ straight or branched chain alkyl, (iii) benzyl and (iv) —$NR_{13}R_{14}$, wherein $R_{13}$ and $R_{14}$ are independently selected from hydrogen and $C_{1-6}$ alkyl;

wherein the $C_{1-3}$ alkyl and benzyl groups are optionally substituted with one or more groups selected from $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, amino, $NR_{13}R_{14}$, aryl and heteroaryl; and (e) X is selected from S and O;

with the proviso that when $R_4$ is isopropyl, then $R_3$ is not halogen.

In an alternative embodiment, the invention is directed to compounds of Formula I wherein $R_1$, $R_3$ and $R_4$ are as described above and $R_2$ is —$NR_{15}R_{16}$ wherein $R_{15}$ and $R_{16}$ are independently selected from hydrogen, optionally substituted $C_{1-8}$ straight or branched chain alkyl, arylalkyl, $C_{3-7}$ cycloalkyl, aryl, heteroaryl, and heterocyclyl or $R_{15}$ and $R_{16}$ taken together with the nitrogen form a heteroaryl or heterocyclyl group; with the proviso that when $R_2$ is $NHR_{16}R_1$ is not —$COOR_6$ where $R_6$ is ethyl.

This invention also provides a pharmaceutical composition comprising the instant compound and a pharmaceutically acceptable carrier.

This invention further provides a method of treating a subject having a condition ameliorated by antagonizing Adenosine A2a receptors or by reducing PDE activity in appropriate cells, which comprises administering to the subject a therapeutically effective dose of the instant pharmaceutical composition.

This invention further provides a method of preventing a disorder ameliorated by antagonizing Adenosine A2a receptors or by reducing PDE activity in appropriate cells in a subject, comprising administering to the subject a prophylactically effective dose of the compound of claim 1 either preceding or subsequent to an event anticipated to cause a disorder ameliorated by antagonizing Adenosine A2a receptors or reducing PDE activity in appropriate cells in the subject.

DETAILED DESCRIPTION OF THE INVENTION

Compounds of Formula 1 are potent small molecule antagonists of the Adenosine A2a receptors that have demonstrated potency for the antagonism of Adenosine A2a, A1, and A3 receptors.

Compounds of Formula I are also potent small molecule phosphodiesterase inhibitors that have demonstrated potency for inhibition of PDE7, PD E5, and PDE4. Some of the compounds of this invention are potent small molecule PDE7 inhibitors which have also demonstrated good selectivity against PDE5 and PDE4.

Preferred embodiments for $R_1$ are $COOR_6$, wherein $R_6$ is selected from H, optionally substituted $C_{1-8}$ straight or branched chain alkyl, optionally substituted aryl and optionally substituted arylalkyl. Preferably $R_6$ is H, or $C_{1-8}$ straight or branched chain alkyl which may be optionally substituted with a substituent selected from CN and hydroxy.

Preferred embodiments for $R_2$ are optionally substituted heterocycle, optionally substituted aryl and optionally substituted heteroaryl. Preferred substituents are from one to three members selected from the group consisting of halogen, alkyl, alkoxy, alkoxyphenyl, halo, triflouromethyl; trifluoro or difluoromethoxy, amino, alkylamino, hydroxy, cyano, and nitro. Preferably, $R_2$ is optionally substituted furan, phenyl or napthyl or $R_2$ is

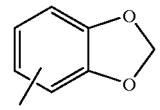

optionally substituted with from one to three members selected from the group consisting of halogen, alkyl, hydroxy, cyano, and nitro. In another embodiment of the instant compound, $R_2$ is —$NR_{15}R_{16}$.

Preferred substituents for $R_3$ include:

(i) hydrogen, halo, $C_{1-8}$ straight or branched chain alkyl, $C_{1-8}$ alkoxy, cyano, $C_{1-4}$ carboalkoxy, trifluoromethyl, $C_{1-8}$ alkylsulfonyl, halogen, nitro, and hydroxy;

(ii) —$NR_{10}R_{,11}$ wherein $R_{10}$ and $R_{11}$ are independently selected from H, $C_{1-8}$ straight or branched chain alkyl, aryl$C_{1-8}$alkyl, $C_{3-7}$ cycloalkyl, carboxy$C_{1-8}$alkyl, aryl, heteroaryl, and heterocyclyl or $R_{10}$ and $R_{11}$, taken together with the nitrogen form a heteroaryl or heterocyclyl group;

(iii) —$NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxy$C_{1-8}$alkyl, aryl, arylalkyl, $R_{30}R_{31}N$ $(CH_2)_p$—, $R_{30}R_{31}NCO(CH_2)_p$—, heteroaryl and heterocyclyl or $R_{12}$ and $R_{13}$ taken together with the carbonyl form a carbonyl containing heterocyclyl group, wherein, $R_{30}$ and $R_{31}$ are independently selected from H, OH, alkyl, and alkoxy, and p is an integer from 1∝6.

Particularly, $R_3$ is selected from the group consisting of

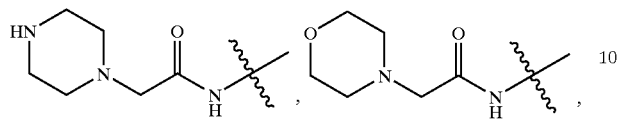

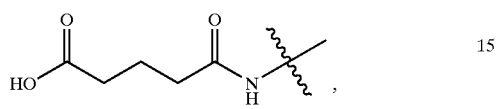

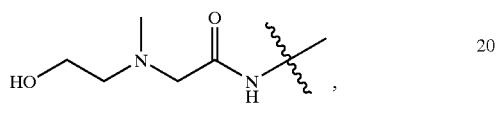

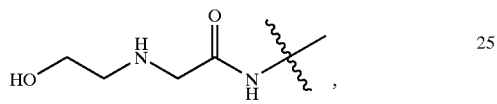

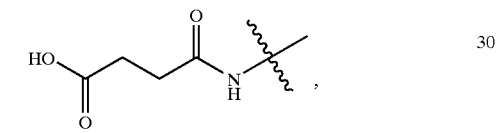

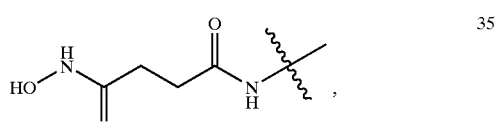

alkyl(CO)NH—, $NH_2$, and $NO_2$.

Preferred embodiments for $R_4$ include hydrogen, $C_{1-3}$ straight or branched chain alkyl, particularly methyl, amine and amino.

In a further embodiment of the instant compound, $R_1$ is $COOR_6$ and $R_2$ is selected from the group consisting of substituted phenyl, and substituted naphthyl or $R_2$ is $NR_{15}R_{16}$.

More particularly, $R_1$ is $COOR_6$ where $R_6$ is alkyl, $R_2$ is substituted phenyl or naphthyl or $R_2$ is $NR_{15}R_{16}$, and $R_3$ is selected from the group consisting of H, nitro, amino, NHAc, halo, hydroxy, alkoxy, or a moiety of the formulae:

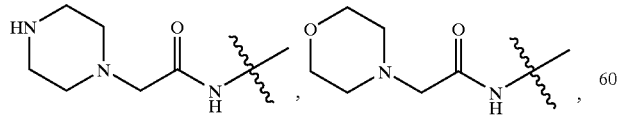

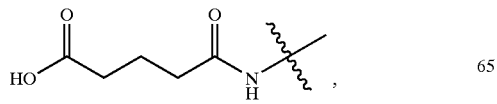

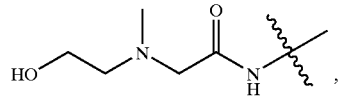

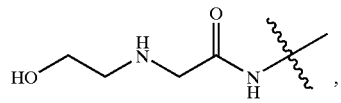

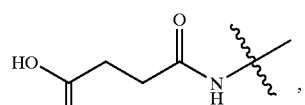

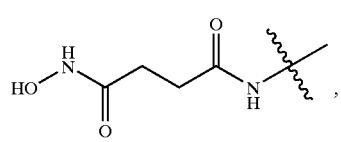

alkyl(CO)NH—, and $R_4$ is selected from hydrogen, $C_{1-3}$ straight or branched chain alkyl, particularly methyl, and amino.

In a preferred embodiment, the compound is selected from the group of compounds shown in Table 1 hereinafter.

More preferably, the compound is selected from the following compounds:

Compound 22

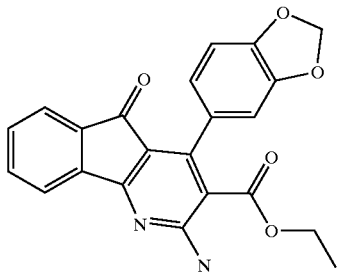

5H-indeno[1,2-b]pyridine-3-carboxylic acid, 2-amino4(1,3-benzodioxol-5yl)-5-oxo-, ethyl ester Compound 24

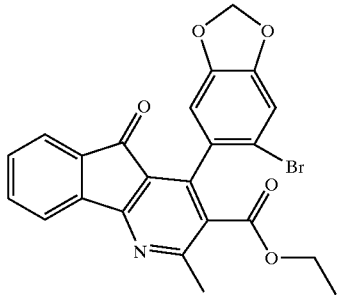

5H-indeno[1,2-b]pyridine-3-carboxylic acid, 4-(6-bromo-1,3-benzodioxol-5-yl)-2-methyl-5-oxo-, ethyl ester Compound 40

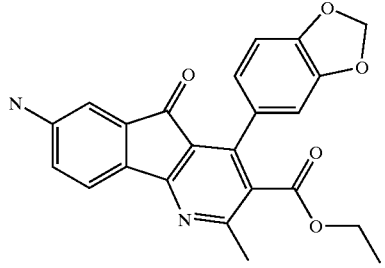

5H-indeno[1,2-b]pyridine-3-carboxylic acid, 8-(acetylamino)41,3-benzodioxol-5-yl)-2-methyl-5-oxo-, ethyl ester Compound 67

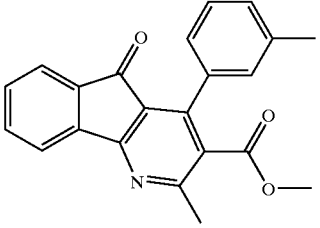

5H-indeno[1,2-b]pyridine-3-carboxylic acid, 7-amino4-(1,3-benzodioxol-5-yl)-2-methyl-5-oxo-, ethyl ester Compound 49

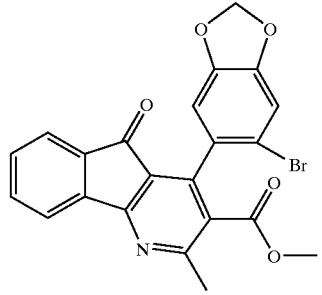

5H-indeno[1,2-b]pyridine-3-carboxylic acid, 2-methyl4-(3-methylphenyl)5-oxo-, methyl ester Compound 82

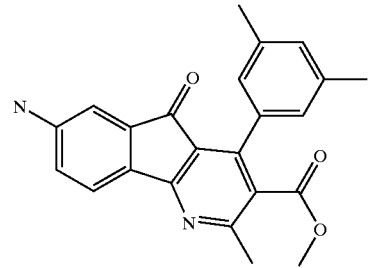

5H-indeno[1,2-b]pyridine-3-carboxylic acid, 4-(6-bromo-1,3-benzodioxol-5-yl)-2-methyl-5-oxo-, methyl ester Compound 51

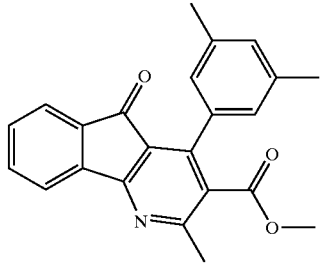

5H-indeno[1,2-b]pyridine-3-carboxylic acid, 7-amino-4-(3,5-dimethylphenyl)-2-methyl-5-oxo-, methyl ester Compound 90

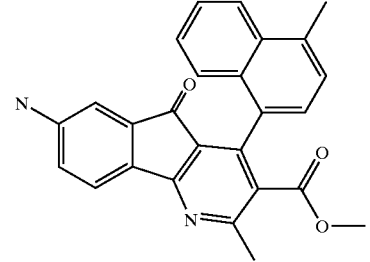

5H-indeno[1,2-b]pyridine-3-carboxylic acid, 4-(3,5-dimethylphenyl)-2-methyl-5-oxo-, methyl ester Compound 56

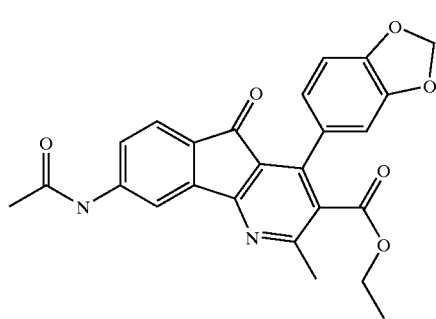

5H-indeno[1,2-b]pyridine-3-carboxylic acid, 7-amino-2-methyl4-(4-methyl-1-naphthalenyl)-5-oxo-, methyl ester Compound 169

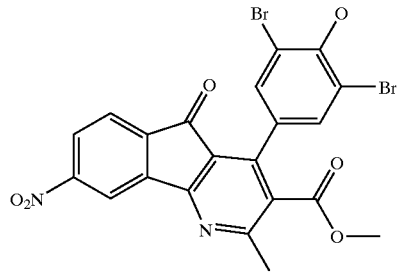

5H-indeno[1,2-b]pyridine-3-carboxylic acid, 4-(3, 5dibromo-4-hydroxyphenyl)-2-methyl-8-nitro-5-oxo-, methyl ester Compound 170

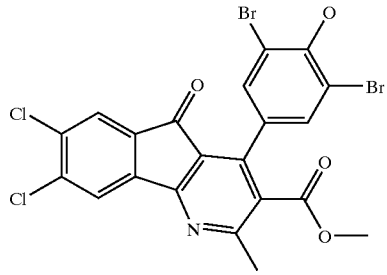

5H-indeno[1,2-b]pyridine-3-carboxylic acid, 8-[(3-carboxy-1-oxopropyl)amino]-4-(3,5-dimethylphenyl-2-methyl-5-oxo-, methyl ester Compound 242

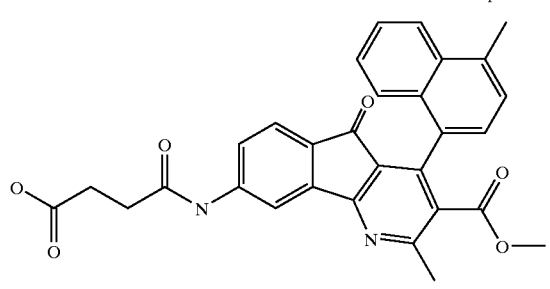

5H-indeno[1,2-b]pyridine-3-carboxylic acid, 7,8-dichloro-4-(3,5-dibromo-4-hydroxyphenyl)-2-methyl-5-oxo-, methyl ester Compound 192

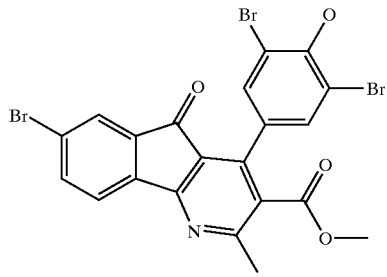

5H-indeno[1,2-b]pyridine-3-carboxylic acid, 8-[(3-carboxy-1-oxopropyl)amino]-2-methyl-4-(4-methyl-1-naphthalenyl)-5oxo-, methyl ester Compound 245

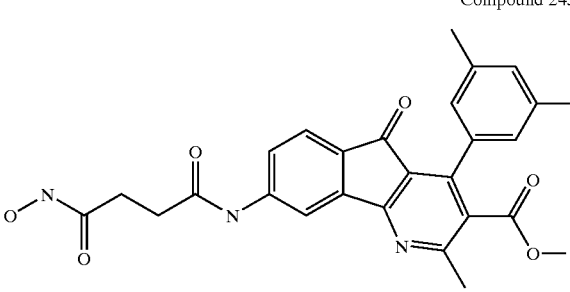

5H-indeno[1,2-b]pyridine-3-carboxylic acid, 7-bromo(3,5-dibromo-4-hydroxyphenyl)-2-methyl-5-oxo-, methyl ester Compound 193

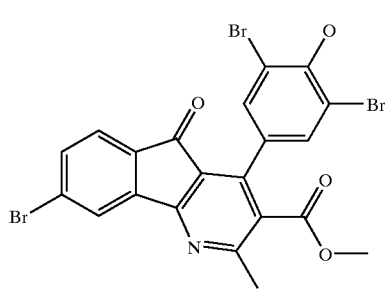

5H-indeno[1,2-b]pyridine-3-carboxylic acid, 4-(3,5-dimethylphenyl)-8-[[4-(hydroxyamino)-1,4-dioxobutyl]amino]-2-methyl-5-oxo-, methyl ester Compound 250

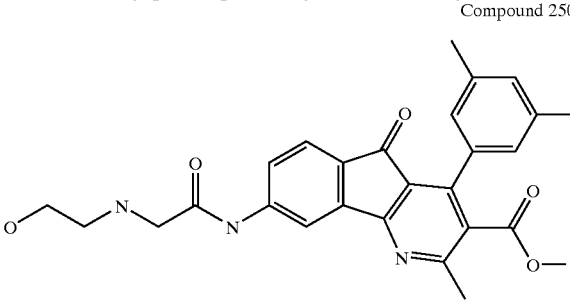

5H-indeno[1,2-b]pyridine-3-carboxylic acid, 8-bromo-4-(3,5-dibromo-4-hydroxyphenyl)2-methyl-5-oxo-, methyl ester Compound 241

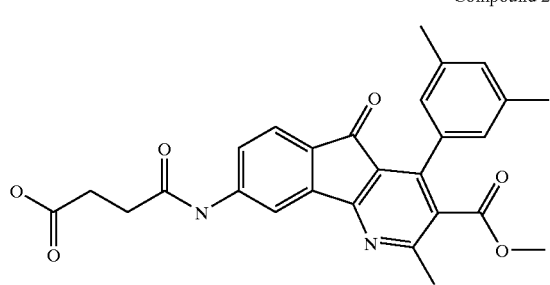

5H-indeno[1,2-b]pyridine-3-carboxylic acid, 4-(3, 5dimethylphenyl)-8[[[(2-hydroxyethyl)amino]acetyl]amino]-2-methyl-5-oxo, methyl ester Compound 251

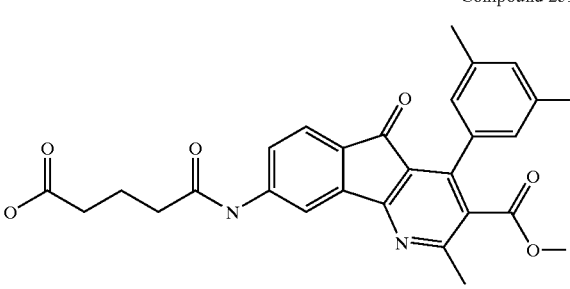

13

5H-indeno[1,2-b]pyridine-3-carboxylic acid, 8-[(4-carboxy-1-oxobutyl)amino]-4-(3,5-dimethylphenyl)-2-methyl-5-oxo-, methyl ester Compound 254

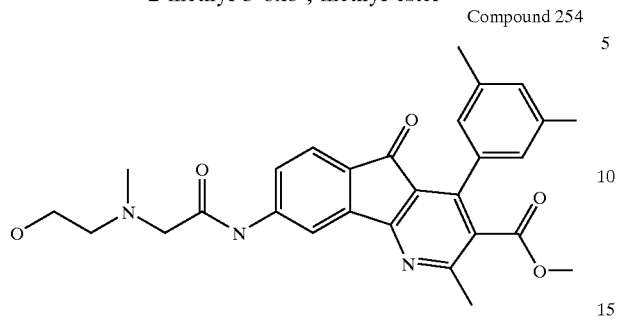

5H-indeno[1,2-b]pyridine-3-carboxylic acid, 4-(3,5-dimethylphenyl)-8-[[[(2-hydroxyethyl)methylamino]acetyl]amino]-2-methyl-5-oxo-, methyl ester Compound 261

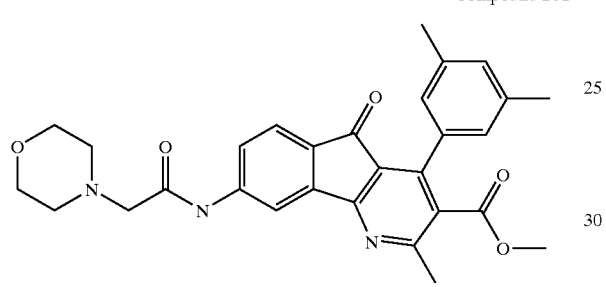

5H-indeno[1,2-b]pyridine-3-carboxylic acid, 4-(3,5dimethylphenyl)-2-methyl-8-[(4-morpholinylacetyl)amino]-5-oxo-, methyl ester Compound 262

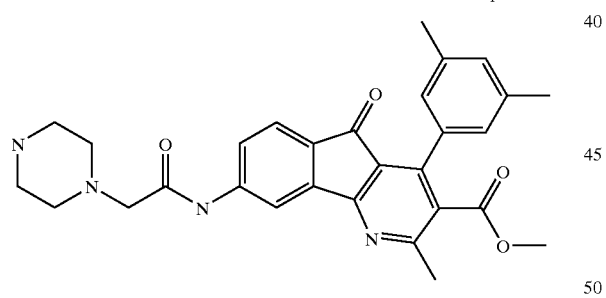

5H-indeno[1,2-b]pyridine-3-carboxylic acid, 4-(3,5-dimethylphenyl)-2-methyl-5-oxo-8-[(1-piperazinylacetyl)amino]-, methyl ester Compound 27

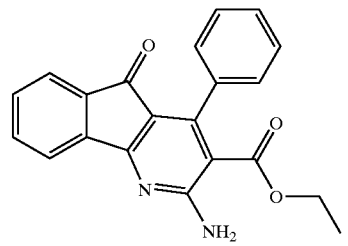

14

5H-indeno[1,2-b]pyridine-3-carboxylic acid, 4-phenyl-2-amino-oxo-, ethyl ester

Compound 66

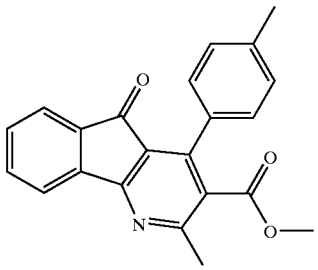

5H-indeno[1,2-b]pyridine-3-carboxylic acid, 4-(4-methylphenyl)-2-methyl-5-oxo-, methyl ester Compound 85

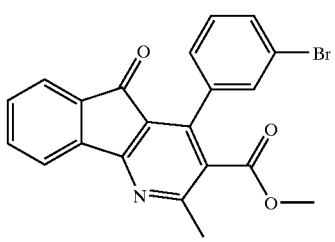

5H-indeno[1,2-b]pyridine-3-carboxylic acid, 4-(3-bromophenyl)2-methyl-5-oxo-, methyl ester Compound 221

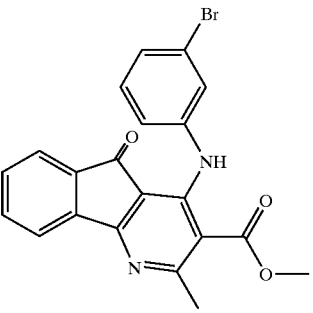

5H-indeno[1,2-b]pyridine-3-carboxylic acid, 4-(3-bromophenylamino)-2-methyl-5-oxo-, methyl ester Compound 265

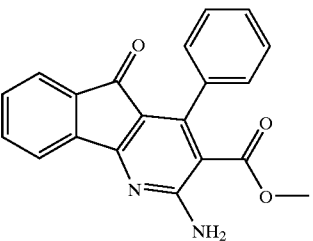

5H-indeno[1,2-b]pyridine-3-carboxylic acid, 4-phenyl-2-amino-5-oxo-, methyl ester Compound 272

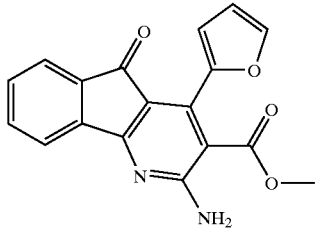

5H-indeno[1,2-b]pyridine-3-carboxylic acid, 4-(2-furyl)-2-amino-5-oxo-, methyl ester Compound 268

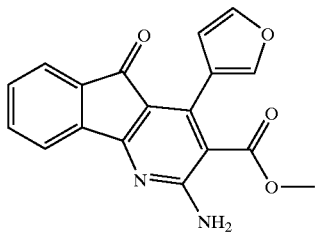

5H-indeno[1,2-b]pyridine-3-carboxylic acid, 4-(3-furyl)-2-amino-5-oxo-, methyl ester Compound 267

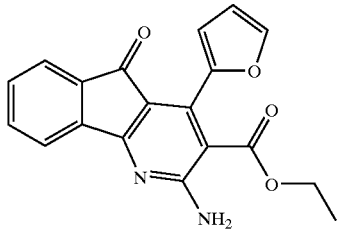

5H-indeno[1,2-b]pyridine-3-carboxylic acid, 4-(2-furyl)-2-amino-5-oxo-, ethyl ester The instant compounds can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention also provides a pharmaceutical composition comprising the instant compound and a pharmaceutically acceptable carrier.

Pharmaceutically acceptable carriers are well known to those skilled In the art and include, but are not limited to, from about 0.01 to about 0.1 M and preferably 0.05 M phosphate buffer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by antagonizing Adenosine A2a receptors or by reducing PDE activity in appropriate cells, which comprises administering to the subject a therapeutically effective dose of the instant pharmaceutical composition.

In one embodiment, the disorder is a neurodegenerative or movement disorder. In another embodiment, the disorder is an inflammatory disorder. In still another embodiment, the disorder is an AIDS-related disorder. Examples of disorders treatable by the instant pharmaceutical composition include, without limitation, Parkinson's Disease, Huntington's Disease, Multiple System Atrophy, Corticobasal Degeneration, Alzheimer's Disease, Senile Dementia, organ transplantation, autoimmune disorders (e.g. arthritis), immune challenge such as a bee sting, inflammatory bowel disease, bronchial disorders (e.g. asthma), HIV/AIDS, cardiovascular disorder, erectile dysfunction, allergies, and psoriasis.

In one preferred embodiment, the disorder is rheumatoid arthritis.

In another preferred embodiment, the disorder is Parkinson's disease.

As used herein, the term "subject" includes, without limitation, any animal or artificially modified animal having a disorder ameliorated by reducing PDE activity in appropriate cells. In a preferred embodiment, the subject is a human. In a more preferred embodiment, the subject is a human, As used herein, "appropriate cells" include, by way of example, cells which display PDE activity. Specific examples of appropriate cells include, without limitation, T-lymphocytes, muscle cells, neuro cells, adipose tissue cells, monocytes, macrophages, fibroblasts.

Administering the instant pharmaceutical composition can be effected or performed using any of the various methods known to those skilled in the art. The instant compounds can be administered, for example, intravenously, intramuscularly, orally and subcutaneously. In the preferred embodiment, the instant pharmaceutical composition is administered orally. Additionally, administration can comprise giving the subject a plurality of dosages over a suitable period of time. Such administration regimens can be determined according to routine methods.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.001 mg/kg of body weight to about 200 mg/kg of body weight of the instant pharmaceutical composition. In another embodiment, the therapeutically and/or prophylactically effective dose is a dose sufficient to deliver from about 0.05 mg/kg of body weight to about 50 mg/kg of body weight. More specifically, in one embodiment, oral doses range from about 0.05 mg/kg to about 100 mg/kg daily. In another embodiment, oral doses range from about 0.05 mg/kg to about 50 mg/kg daily, and in a further embodiment, from about 0.05 mg/kg to about 20 mg/kg daily. In yet another embodiment, infusion doses range from about 1.0 $\mu$g/kg/min to about 10 mg/kg/min of inhibitor, admixed with a pharmaceutical carrier over a period ranging from about several minutes to about several days. In a further embodiment, for topical administration, the instant compound can be combined with a pharmaceutical carrier at a drug/carrier ratio of from about 0.001 to about 0.1.

This invention still further provides a method of preventing an inflammatory response in a subject, comprising administering to the subject a prophylactically effective amount of the instant pharmaceutical composition either preceding or subsequent to an event anticipated to cause the inflammatory response in the subject. In the preferred embodiment, the event is an insect sting or an animal bite.

Definitions and Nomenclature

Unless otherwise noted, under standard nomenclature used throughout this disclosure the terminal portion of the designated side chain is described first, followed by the adjacent functionality toward the point of attachment.

As used herein, the following chemical terms shall have the meanings as set forth in the following paragraphs: "independently", when in reference to chemical substituents, shall mean that when more than one substituent exists, the substituents may be the same or different;.

"Alkyl" shall mean straight, cyclic and branched-chain alkyl. Unless otherwise stated, the alkyl group will contain 1–20 carbon atoms. Unless otherwise stated, the alkyl group may be optionally substituted with one or more groups such as halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, carboxamide, hydroxamic acid, sulfonamide, sulfonyl, thiol, aryl, aryl($c_1$-$c_8$)alkyl, heterocyclyl, and heteroaryl.

"Alkoxy" shall mean —O-alkyl and unless otherwise stated, it will have 1–8 carbon atoms.

The term "bioisostere " is defined as "groups or molecules which have chemical and physical properties producing broadly similar biological properties." (Burger's Medicinal Chemistry and Drug Discovery, M. E. Wolff, ed. Fifth Edition, Vol. 1, 1995, Pg. 785).

"Halogen" shall mean fluorine, chlorine, bromine or iodine; "PH" or "Ph" shall mean phenyl; "Ac" shall mean acyl; "Bn" shall mean benzyl.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

"Aryl" or "Ar," whether used alone or as part of a substituent group, is a carbocyclic aromatic radical Including, but not limited to, phenyl, 1- or 2-naphthyl and the like. The carbocyclic aromatic radical may be substituted by independent replacement of 1 to 5 of the hydrogen atoms thereon with halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Whether used alone or as part of a substituent group, "heteroaryl" refers to a cyclic, fully unsaturated radical having from five to ten ring atoms of which one ring atom is selected from S, O, and N; 0–2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrroyl, pyrazolyl, imidazolyl , thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, 2-oxazepinyl, azepinyl, N-oxo-pyridyl, 1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, benzothiopyranyl, indazolyl, indolizinyl, benzofuryl, chromonyl, coumarinyl, cinnolinyl, quinoxalinyl, indazolyl, pyrrolopyridinyl, furopyridinyl (such as furo[2,3-c]pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, thienothienyl, and furyl. The heteroaryl group may be substituted by independent replacement of 1 to 5 of the hydrogen atoms thereon with halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Heteroaryl may be substituted with a mono-oxo to give for example a 4-oxo-1H-quinoline.

The terms "heterocycle," "heterocyclic," and "heterocycle" refer to an optionally substituted, fully or partially saturated cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolyl; oxazolidinyl; isoxazolinyl; thiazolidinyl;

isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; dihydrobenzothiopyranyl; dihydrobenzothiopyranyl sulfone; dihydrobenzopyranyl; indolinyl; isochromanyl; isoindolinyl; piperonyl; tetrahydroquinolinyl; and the like.

Substituted aryl, substituted heteroaryl, and substituted heterocycle may also be substituted with a second substituted-aryl, a second substituted-heteroaryl, or a second substituted-heterocycle to give, for example, a 4-pyrazol-1-yl-phenyl or 4-pyridin-2-yl-phenyl.

Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

I. General Synthetic Schemes

Representative compounds of the present invention can be synthesized in accordance with the general synthetic methods described below and illustrated in the following general schemes. The products of some schemes can be used as intermediates to produce more than one of the instant compounds. The choice of intermediates to be used to produce subsequent compounds of the present invention is a matter of discretion that is well within the capabilities of those skilled in the art.

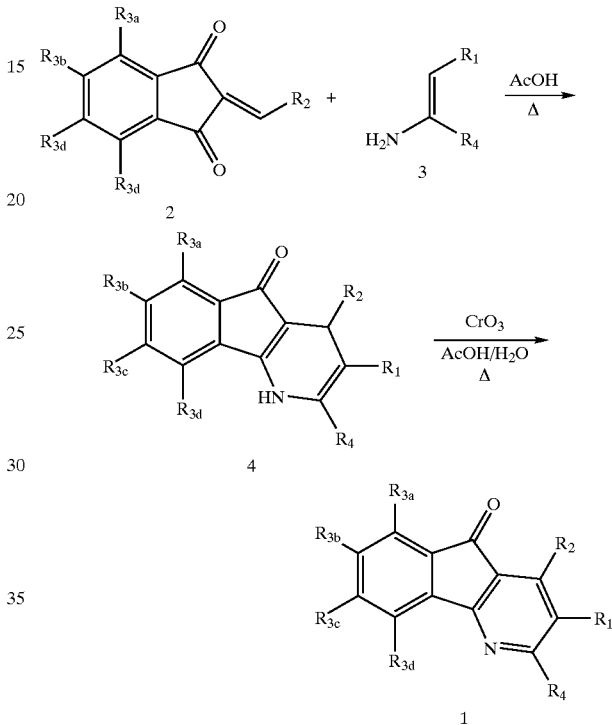

Procedures described in Scheme 1, wherein $R_{3a}$, $R_{3b}$, $R_{3c}$, and $R_{3d}$ are independently any $R_3$ group, and $R_1$, $R_2$, $R_3$, and $R_4$ are as described above, can be used to prepare compounds of the invention wherein X is O.

Benzylidenes 2 may be obtained by known methods (Bullington, J. L; Cameron, J. C.; Davis, J. E.; Dodd, J. H.; Harris, C. A.; Henry, J. R.; Pellegrino-Gensey, J. L.; Rupert, K. C.; Siekierka, J. J. Bioorg. Med. Chem. Lett. 1998, 8, 2489; Petrow, V.; Saper, J.; Sturgeon, B. J. Chem. Soc. 1949, 2134). Hantzsch reaction of the benzylidene compounds with enamines 3 can be performed in refluxing acetic acid (Petrow et al., supra). When the desired enamines are not available, alternate Hantzsch conditions may be utilized which involve adding ammonium acetate to the reaction. The resulting dihydropyridines 4 are oxidized with chromium trioxide to obtain the desired pyridines 1 (Petrow et al., supra). In cases where the substitution pattern on the fused aromatic ring ($R_3$) leads to a mixture of regioisomers, the products can be separated by column chromatography.

In some cases, especially where $R_2$ is an alkyl group, another modification of the Hantzsch may be performed which uses three components (Bocker, R. H.; Buengerich, P. J. Med. Chem. 1986, 29, 1596). Where $R_2$ is an alkyl group it is also necessary to perform the oxidation with DDQ or $MnO_2$ instead of chromium (VI) oxide (Vanden Eynde, J. J.; Delfosse, F.; Mayence, A.; Van Haverbeke, Y. *Tetrahedron*

1995, 51, 6511).

Scheme 2

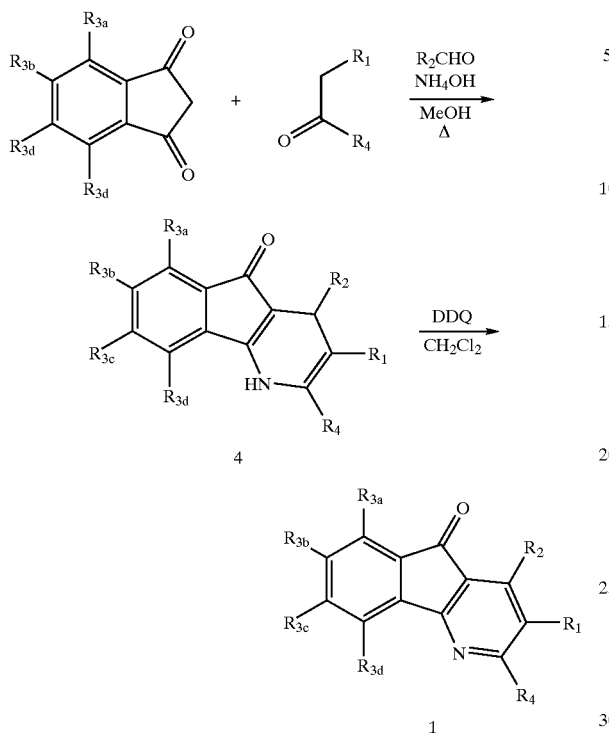

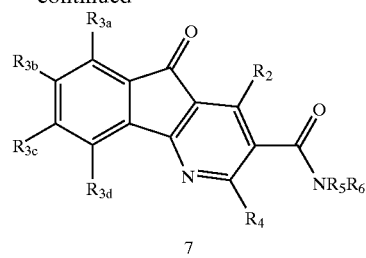

The procedure for making compounds where $R_4$ is $NH_2$ may be slightly modified. These compounds are prepared in one step from the benzylidenes 2 and alkyl amidinoacetate (Kobayashi, T.; Inoue, T.; Kita, Z.; Yoshiya, H.; Nishino, S.; Oizumi, K.; Kimura, T. Chem. Pharm. Bull. 1995, 43, 788) as depicted in Scheme 4 wherein R is $R_5$ or $R_6$ as described above.

Scheme 4

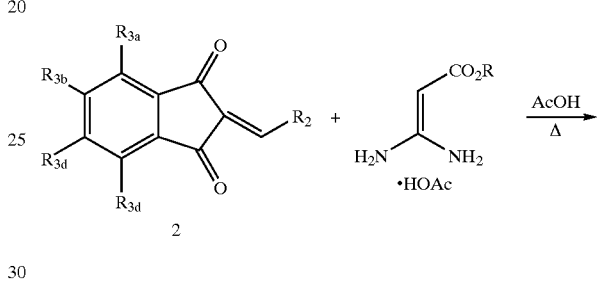

In order to obtain the corresponding carboxylic acids and amides, the cyanoethyl esters 5 are prepared as described above. The esters are converted to the carboxylic acids by treatment with sodium hydroxide in acetone and water (Ogawa, T.; Matsumoto, K.; Yokoo, C.; Hatayama, K.; Kitamura, K. *J. Chem. Soc., Perkin Trans.* 1 1993, 525). The corresponding amides can then be obtained from the acids using standard means.

Scheme 3

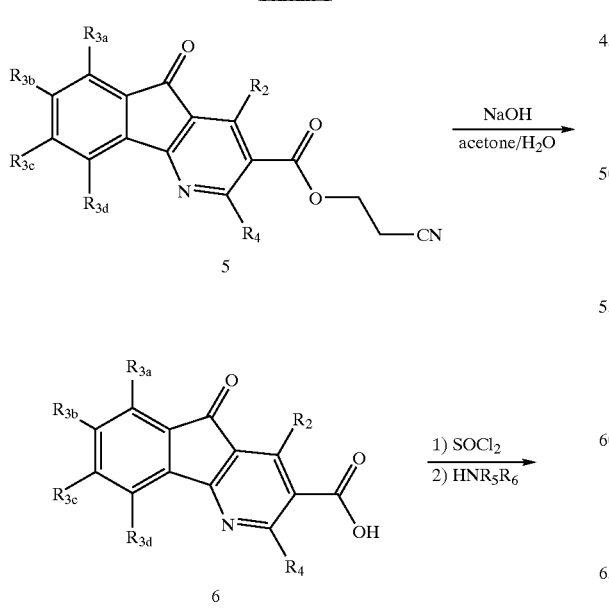

The dihydropyridine lactones 9 can be synthesized from benzylidenes 8 (Zimmer, H.; Hillstrom, W. W.; Schmidt, J. C.; Seemuth, P. D.; Vogeli, R. *J. Org. Chem.* 1978, 43, 1541) and 1,3-indanedione, as shown in Scheme 5, and the corresponding pyridine is then obtained by oxidation with manganese dioxide.

Scheme 5

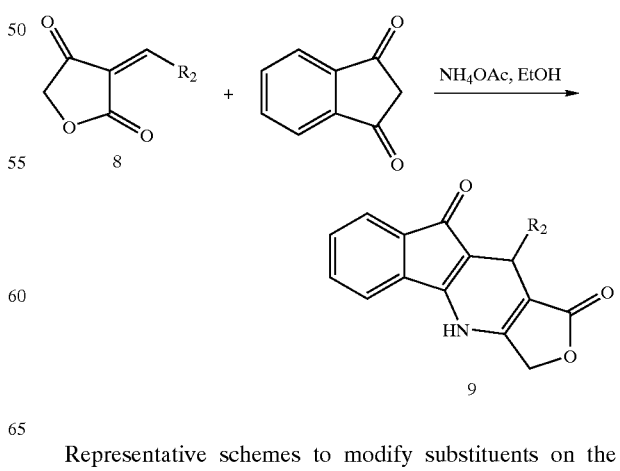

Representative schemes to modify substituents on the fused aromatic ring are shown below. The amines 11 are obtained from the corresponding nitro compounds 10 by reduction with tin (II) chloride (Scheme 6). Reaction of the amines with acetyl chloride provide the amides 12.

Scheme 6

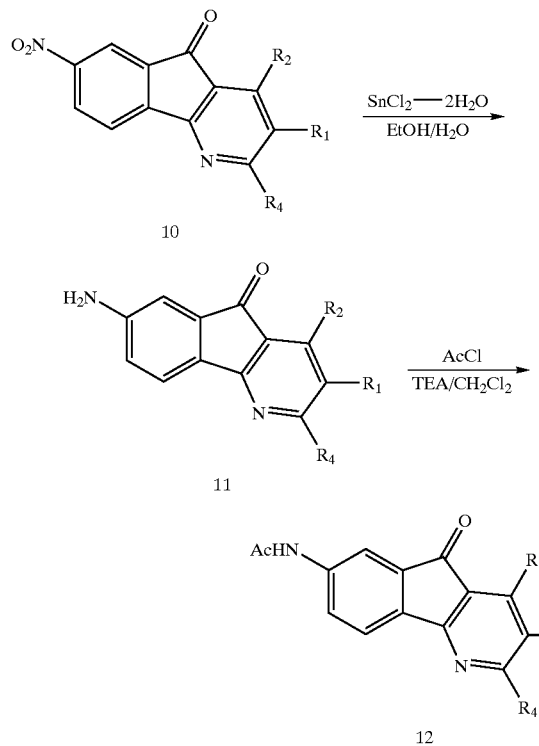

In accordance with Scheme 7 wherein Y is 0, and n is an integer from 1–3, an alkyl chain with a carboxylic acid at the terminal end can also be added to the amines 11. For example, reaction with either succinic anhydrid (Omuaru, V. O. T.; *Indian J. Chem.*, Sect B. 1998, 37, 814) or β-propiolactone (Bradley, G.; Clark, J.; Kernick, W. *J. Chem. Soc., Perkin Trans.* 1 1972, 2019) can provide the corresponding carboxylic acids 13. These carboxylic acids are then converted to the hydroxamic acids 14 by treatment with ethyl chloroformate and hydroxylamin (Reddy, A. S.; Kumar, M. S.; Reddy, G. R. *Tetrahedron Lett.* 2000, 41, 6285).

Scheme 7

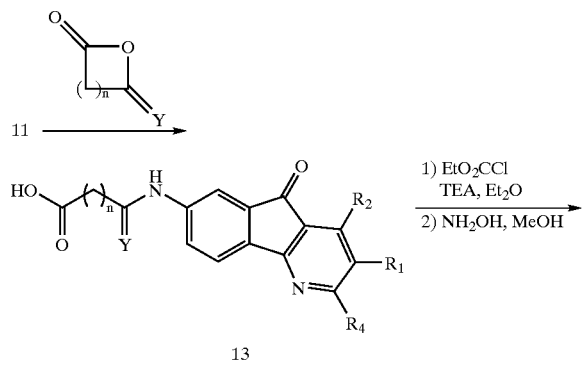

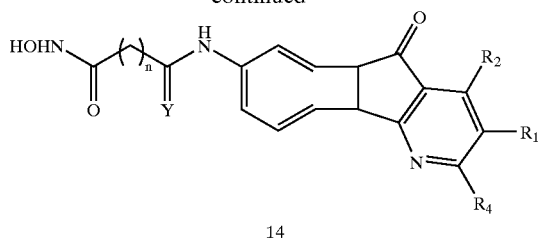

The amines 11 can also be treated with glycolic acid to afford alcohols 15 (Jursic, B. S.; Zdravkovski, Z. *Synthetic Comm.* 1993,23, 2761) as shown in Scheme 8.

Scheme 8

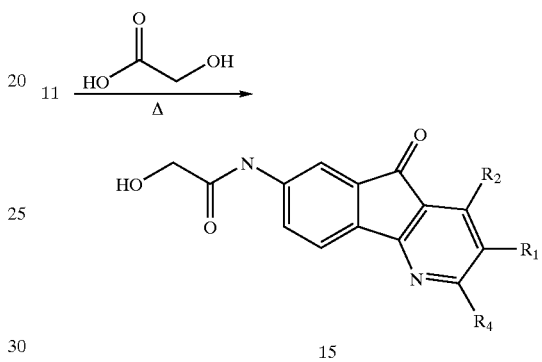

As shown in Scheme 9, the aminoindenopyridines 11 may also be treated with chloroacetylchloride followed by amines to provide the more elaborate amines 16 (Weissman, S. A.; Lewis, S.; Askin, D.; Volante, R. P.; Reider, P. J. *Tetrahedron Led.* 1998, 39,7459). Where $R_6$ is a hydroxyethyl group, the compounds can be further converted to piperazinones 17.

Scheme 9

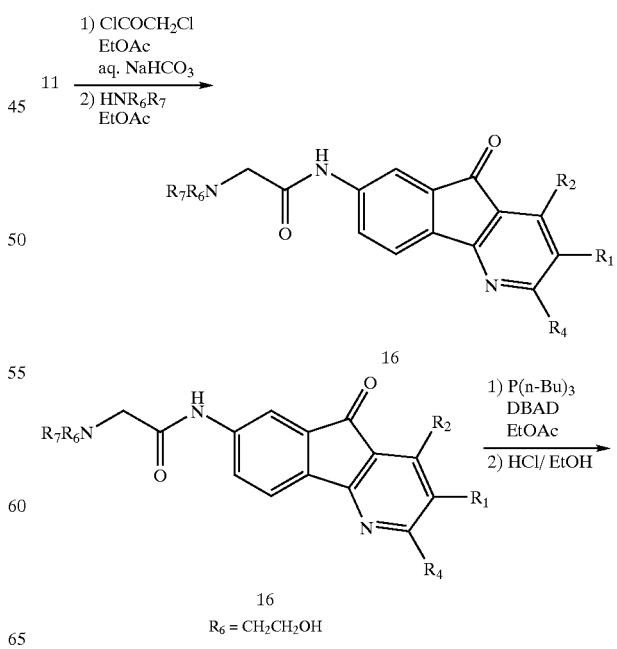

-continued

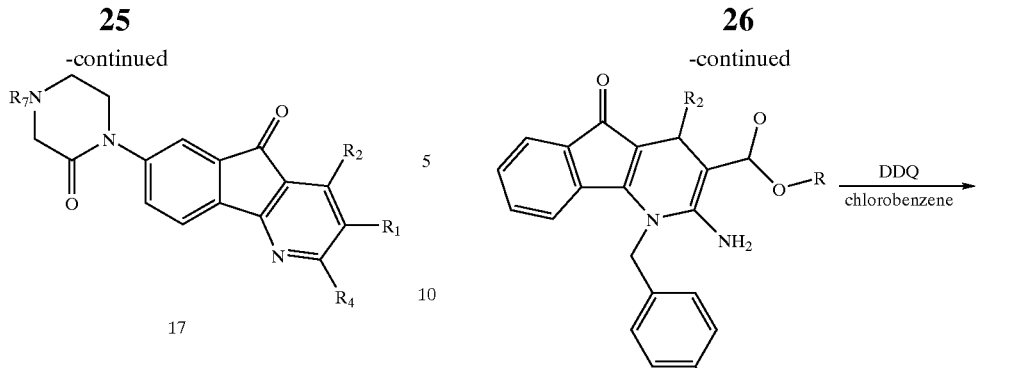

17

The 4-aminoindenopyridines 19 can be synthesized from the 4-chloroindenopyridines 18 using a known procedure (Gorlitzer, K.; Herbig, S.; Walter, R. D. *Pharmazie* 1997, 504) or via palladium catalyzed coupling (Scheme 10).

Scheme 10

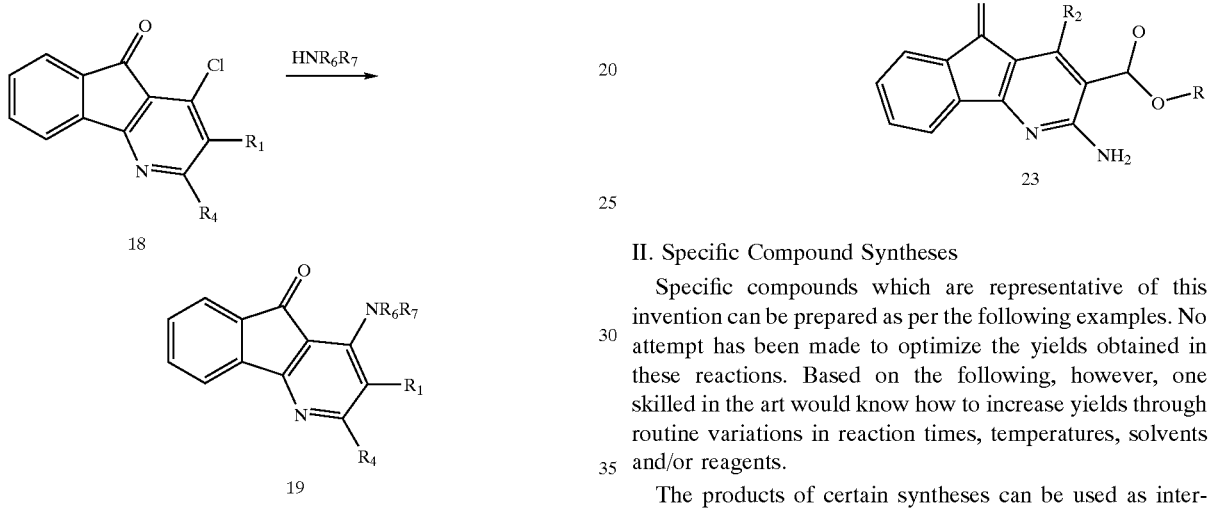

Cyanoesters 20 can be prepared by known methods (Lee, J.; Gauthier, D.; Rivero, R. A. *J. Org. Chem.* 1999, 64, 3060). Reaction of 20 with enaminone 21 (Iida, H.; Yuasa, Y.; Kibayashi, C. *J. Org. Chem.* 1979, 44, 1074) in refluxing 1-propanol and triethylamine gave dihydropyridine 22, wherein R is $R_5$ or $R_6$ as described above, (Youssif, S.; El-Bahaie, S.; Nabih, E. *J. Chem. Res. (S)* 1999, 112 and Bhuyan, P.; Borush, R. C.; Sandhu, J. S. *J. Org. Chem.* 1990, 55, 568), which can then be oxidized and subsequently deprotected to give pyridine 23.

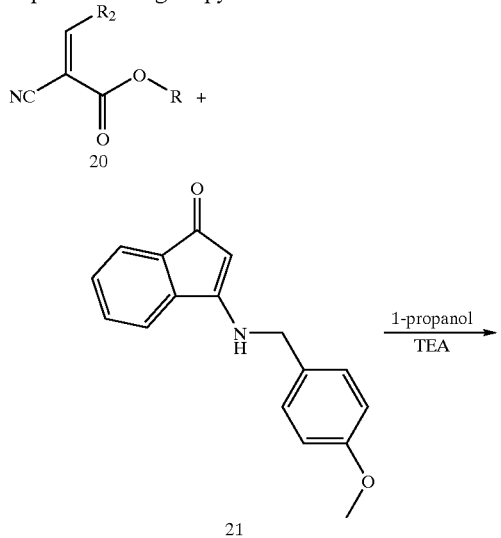

-continued

22

23

II. Specific Compound Syntheses

Specific compounds which are representative of this invention can be prepared as per the following examples. No attempt has been made to optimize the yields obtained in these reactions. Based on the following, however, one skilled in the art would know how to increase yields through routine variations in reaction times, temperatures, solvents and/or reagents.

The products of certain syntheses can be used as intermediates to produce more than one of the instant compounds. In those cases, the choice of intermediates to be used to produce compounds of the present invention is a matter of discretion that is well within the capabilities of those skilled in the art.

EXAMPLE 1

Hantzsch Condensation to Form Dihydropyridine 4 ($R_1$=COOMe; $R_2$=3,5-dimethylphenyl; $R_{3b,c}$=Cl; $R_{3a,b}$=H; $R_4$=Me)

To a refluxing solution of benzylidene 2 (0.500 g, 1.5 mmol) in acetic acid (10 mL) was added methyl-3-aminocrotonate (0.695 g, 6.0 mmol). The reaction was heated to reflux for 20 minutes, then water was added until a precipitate started to form. The reaction was cooled to room temperature. The mixture was filtered and washed with water to obtain 0.354 g (55%) of a red solid. MS m/z 450 ($M^+$+23), 428 ($M^+$+1).

EXAMPLE 2

Alternate Hantzsch Conditions to Form Dihydropyridine 4 ($R_1$=$CO_2Me$; $R_2$=2,4-dimethylphenyl; $R_3$=H; $R_4$=Et)

To a refluxing solution of benzylidene 2 (1.00 g, 3.82 mmol) in acetic acid (12 Ml) was added methyl propionylacetate (1.98 g, 15.2 mmol) and ammonium acetate (1.17 g, 15.2 mmol). The reaction was heated for 20 min and then cooled to room temperature. No product precipitated from the solution, so the reaction was heated to reflux and then water was added until a solid began to precipitate. After cooling to room temperature, the mixture was filtered and the red solid washed with water to yield 1.29 g (90%) of product. MS m/z 396 ($M^++23$), 374 ($M^++1$).

EXAMPLE 3

Oxidation of Dihydropyridine 4 to Pyridine 1 ($R_1$=COOMe; $R_2$=3,5-dimethylphenyl; $R_{3a,b}$=Cl; $R_{3a,d}$=H; $R_4$=Me)

To a refluxing solution of dihydropyridine 4 (0.250 g, 0.58 mmol) in acetic acid (10 mL) was added a solution of chromium (VI) oxide (0.584 g, 0.58 mmol) in 1 mL water. After 30 minutes at reflux, the reaction was diluted with water until a precipitate started to form. The mixture was cooled to room temperature and allowed to stand overnight. The mixture was filtered and washed with water to give 0.199 g (81%) of a yellow solid. MS m/z 448 ($M^++23$), 426 ($M^++1$).

EXAMPLE 4

Oxidation of Dihydropyridine 4 to Pyridine 1 ($R_1$=COOMe; $R_2$=(4-methyl)-1-naphthyl; $R_{3b,c}$=H, $NO_2$/$NO_2$, H; R=Me)

To a refluxing suspension of regioisomeric dihydropyridines 4 (3.59 g, 8.16 mmol) in acetic acid (40 mL) was added a solution of chromium (VI) oxide (0.816 g, 8.16 mmol) in 3 mL water. After 20 minutes at reflux, the reaction was diluted with water until a precipitate started to form. The mixture was cooled to room temperature and allowed to stand overnight. The mixture was filtered and washed with water to yield the mixture of regioisomers as a yellow solid. The products were purified by column chromatography eluting with hexanes:ethyl acetate to yield 1.303 g (37%) of pyridine 1 ($R_{3b}$=$NO_2$; $R_{3c}$=H) and 0.765 g (21%) of its regioisomer ($R_{3b}$=H; $R_{3c}$=$NO_2$). MS m/z 461 ($M^++23$), 439 ($M^++1$).

EXAMPLE 5

Alternate Three Component Hantzsch Reaction to Form Dihydropyridine 4 ($R_1$=$CO_2Me$; $R_2$=cyclohexyl; $R_3$=H; $R_4$=Me)

Cyclohexane carboxaldehyde (2.0 g, 17.8 mmol), 1,3-indandione (2.6 g, 17.8 mmol), methylacetoacetate (2.0 g, 17.8 mmol), and ammonium hydroxide (1 mL) were refluxed in 8 mL of methanol for 1.5 hours. The temperature was lowered to approximately 50° C. and the reaction was stirred overnight. The reaction was cooled to room temperature, filtered and the solid washed with water. The residue was then dissolved in hot ethanol and filtered while hot. The filtrate was concentrated to yield 4.1 g (68%) of the product which was used without purification. MS m/z 336 ($M^--1$).

EXAMPLE 6

DDQ Oxidation of Dihydropyridine 4 ($R_1$=$CO_2Me$; $R_2$=cyclohexyl: $R_3$=H; $R_4$=Me)

To a solution of dihydropyridine 4 (2.50 g, 7.40 mmol) in 15 mL of dichloromethane was added 2,3-dichloro-3,6-dicyano-1,4-benzoquinone (1.70 g, 7.40 mmol). The reaction was stirred at room temperature for four hours. The mixture was filtered and the residue was washed with dichloromethane. After the filtrate was concentrated, the residue was purified by column chromatography eluting with ethyl acetate: hexanes to yield 0.565 g (23%) of a yellow solid. MS m/z 358 ($M^++23$), 336 ($M^++1$).

EXAMPLE 7

$MnO_2$ Oxidation of Dihydropyridine 4 ($R_1$=$CO_2Me$; $R_2$=4-(dimethylamino)phenyl: $R_3$=H; $R_4$=Me)

To a solution of dihydropyridine 4 (0.50 g, 1.3 mmol) in 10 mL of dichloromethane was added manganese dioxide (2.5 g, 28.7 mmol). The reaction was stirred at room temperature overnight before filtering and washing with dichloromethane. The filtrate was concentrated to yield 0.43 g (88%) of orange solid 1. MS m/z 395 ($M^++23$), 373 ($M^++1$).

EXAMPLE 8

Cleavage of Carboxylic Ester 5 ($R_2$=2,4-dimethylphenyl; $R_3$=H; $R_4$=Me)

To a suspension of ester 5 (2.75 g, 6.94 mmol) in acetone (50 mL) was added aqueous 1 M NaOH (100 mL). After stirring at room temperature for 24 hours, the reaction mixture was diluted with 100 mL of water and washed with dichloromethane (2×100 mL). The aqueous layer was cooled to 0° C. and acidified with concentrated HCl. The mixture was filtered and washed with water to yield 1.84 g (77%) yellow solid 6. MS m/z 366 ($M^++23$), 343 ($M^++1$).

EXAMPLE 9

Preparation of Amide 7 ($R_2$=2.4-dimethylphenyl; $R_3$=H; $R_4$=Me; $R_5$=H; $R_6$=Me)

A solution of carboxylic acid 6 (0.337 g, 0.98 mmol) in thionyl chloride (10 mL) was heated at reflux for 1 hour. The solution was cooled and concentrated in vacuo. The residue was diluted with $CCl_4$ and concentrated to remove the residual thionyl chloride. The residue was then dissolved in THF (3.5 mL) and added to a 0° C. solution of methylamine (1.47 mL of 2.0 M solution in THF, 2.94 mmol) in 6.5 mL THF. The reaction was warmed to room temperature and stirred overnight. The mixture was poured into water, filtered, washed with water and dried to yield 0.263 g (75%) of tan solid. MS m/z 357($M^++1$).

EXAMPLE 10

Preparation of Pyridine 1 ($R_1$=$CO_2Et$: $R_2$=4-nitrophenyl; $R_3$=H; $R_4$=$NH_2$)

To a refluxing solution of benzylidene 2 (1.05 g, 3.76 mmol) in 10 mL of acetic acid was added ethyl amidinoacetate acetic acid salt (0.720 g. 3.76 mmol). The resulting solution was heated at reflux overnight. After cooling to room temperature, the resulting precipitate was removed by filtration and washed with water. This impure residue was heated in a minimal amount of ethanol and then filtered to yield 0.527 g (35%) of a yellow solid. MS m/z 412 ($M^++23$), 390 ($M^++1$).

EXAMPLE 11

Hantzsch Condensation of Benzylidene 8 ($R_2$=3-methoxyphenyl) and 1,3-indandione The benzylidene 8 (2.00 g, 9.2 mmol), 1,3-indandione (1.34 g, 0.2 mmol) and ammonium acetate (2.83 g, 36.7 mmol) were added to 30 mL of ethanol and heated to reflux overnight. The reaction mixture was cooled to room temperature and diluted with ethanol. A yellow precipitate was collected by filtration, washed with ethanol, and dried under vacuum to yield 1.98 g (63%) of the dihydropyridine 9. MS m/z 346 ($M^+ +1$).

EXAMPLE 12

Reduction to Prepare Amine 11 ($R_1=CO_2Me$; $R_2=$4-methylnaphthyl; $R_4=Me$)

To a refluxing suspension of pyridine 10 (0.862 g, 1.97 mmol) in 35 mL of ethanol was added a solution of tin (II) chloride dihydrate (1.33 g, 5.90 mmol) in 6 mL of 1:1 ethanol: concentrated HCl. The resulting solution was heated at reflux overnight. Water was added until a precipitate started to form and the reaction was cooled to room temperature. The mixture was then filtered and washed with water. After drying, the residue was purified by column chromatography eluting with hexanes: ethyl acetate to yield 0.551 g (69%) of an orange solid. MS m/z 431 ($Me^+ +23$), 409 ($M^+ +1$).

EXAMPLE 13

Acetylation of Amine 11 ($R_1=CO_2Et$; $R_2=$3,4-methylenedioxyphenyl; $R_4=Me$)

To a solution of amine 11 (0.070 g, 0.174 mmol) in 15 mL of dichloromethane was added triethylamine (0.026 g, 0.261 mmol) and acetyl chloride (0.015 g, 0.192 mmol). After stirring overnight at room temperature, the reaction mixture was diluted with water and then extracted with dichloromethane (3×35 mL). The combined organics were washed with brine, dried over $MgSO_4$, and concentrated. The residue was purified by silica gel chromatography eluting with hexanes: ethyl acetate to yield 0.054 g (70%) of amide 12. MS m/z 467 ($M^+ +23$), 445 ($M^+ +1$).

EXAMPLE 14

Preparation of Carboxylic Acid 13 ($R_1=CO_2Me$; $R_2=$3,5dimethylphenyl; $R_4=Me$; Y=O; n=2)

To a suspension of amine 11 (0.079 g, 0.212 mmol) in 5 mL of benzene was added succinic anhydride (0.021 g, 0.212 mmol). After heating at reflux for 24 hours, the reaction mixture was filtered and washed with benzene. The residue was dried under high vacuum and then washed with ether to remove the excess succinic anhydride. This yielded 0.063 g (63%) of carboxylic acid 13. MS m/z 473 ($M^+ +1$).

EXAMPLE 15

Preparation of Carboxylic Acid 13 ($R_1=CO_2Me$; $R_2=$3,5-dimethylphenyl: $R_4=Me$; $Y=H_2$: n=1)

To a refluxing solution of amine 11 (0.078 g, 0.210 mmol) in 5 mL of acetonitrile was added β-propiolactone (0.015 g, 0.210 mmol). The reaction was heated to reflux for 72 hours before cooling to room temperature. The reaction mixture was concentrated. The residue was mixed with 10% aqueous sodium hydroxide and washed sequentially with ether and ethyl acetate. The aqueous layer was acidified with concentrated HCl and extracted with dichloromethane (2×25 mL). The combined organics were dried over $MgSO_4$, filtered, and concentrated. The residue was purified by column chromatography eluting with 5% MeOH in dichloromethane to yield 0.020 g (21%) of an orange solid. MS m/z 467 ($M^+ +23$), 445 ($M^+ +1$).

EXAMPLE 16

Preparation of Hydroxamic Acid 14 ($R_1=CO_2Me$; $R_2=$(4-methyl)-1-naphthyl: Y=O; n=2; $R_4=Me$)

To a 0° C. suspension of carboxylic acid 13 (0.054 g, 0.106 mmmol) in 10 mL of diethyl ether was added triethylamine (0.014 g, 0.138 mmol) and then ethyl chloroformate (0.014 g, 0.127 mmol). The mixture was stirred at 0° C. for 30 minutes and them warmed to room temperature. A solution of hydroxylamine (0.159 mmol) in methanol was added and the reaction was stirred overnight at room temperature. The mixture was filtered and the residue was washed with ether and dried under vacuum to yield 0.030 g (54%) of a yellow solid. MS m/z 524 ($M^+ +1$).

EXAMPLE 17

Preparation of Amide 15 ($R_1=CO_2Me$; $R_2=$3,5-dimethylphenyl: $R_4=Me$)

A mixture of amine 11 (0.201 g, 0.54 mmol) and glycolic acid (0.049 g, 0.65 mmol) was heated at 120–160° C. for 30 minutes. During heating, more glycolic acid was added to ensure that excess reagent was present. Once the starting material was consumed, the reaction was cooled to room temperature, and diluted with dichloromethane. The resulting mixture was extracted with 20% NaOH, followed by 10% HCl, and finally water. The combined organics were concentrated and triturated with ether. Purification by column chromatography eluting with ethyl acetate: hexanes yielded 0.012 g, (5%) of a yellow solid. MS m/z453 ($M^+ +23$), 431 ($M^+ +1$).

EXAMPLE 18

Preparation of Amide 16 ($R_1=CO_2Me$; $R_2=$3,5-dimethylphenyl; $R_4=Me$; $NR_6R_7=$morpholino)

To a 0° C. mixture of amine 11 (0.123 g, 0.331 mmol) in 2 mL of 20% a aqueous $NaHCO_3$ and 3 mL of ethyl acetate was added chloroacetyl chloride (0.047 g, 0.413 mmol). The reaction was warmed to room temperature and stirred for 45 minutes. The mixture was poured into a separatory funnel and the aqueous layer was removed. The organic layer containing the crude chloroamide was used without purification. To the ethyl acetate solution was added morpholine (0.086 g, 0.992 mmol) and the reaction was heated to approx. 65° C. overnight. The reaction was diluted with water and cooled to room temperature. After extraction with ethyl acetate (3×25 mL), the combined organics were washed with brine, dried over $MgSO_4$ and concentrated to yield 0.130 g (79%) of a yellow solid. MS m/z 522 ($M^+ +23$), 500 ($M^+ +1$).

EXAMPLE 19

Preparation of piperazinone 17 ($R_1=CO_2Me$; $R_2=$3,5-dimethylphenyl; $R_4=Me$; $R_7=H$)

To a 0° C. solution of amide 16 ($R_6=CH_2CH_2OH$) (0.093 g, 0.20 mmol), tri n-butylphosphine (0.055 g, 0.27 mmol) in 0.35 mL ethyl acetate was slowly added di-tert-butyl azodicarboxylate (0.062 g, 0.27 mmol) in 0.20 mL ethyl acetate. The reaction was allowed to stand for 15 minutes and then heated to 40° C. overnight. 4.2 M ethanolic HCl was added dropwise. The mixture was cooled to 0° C. and allowed to stand for 2 hours. The mixture was filtered and washed with cold ethyl acetate. Purification by column chromatography with 1–5% MeOH in $CH_2Cl_2$ yielded 0.011 (12%) of a white solid. MS m/z 478 ($M^+ +23$), 456 ($M^+ +1$).

EXAMPLE 20

Preparation of 4-Aminoindenopyridine 19 ($R_1$=$CO_2Me$; $R_4$=Me; $R_6$=Me; $R_7$=phenyl)

To a solution of 4-chloroindenopyridine 18 (0.069 g, 0.240 mmol) in 10 mL of 2-ethoxyethanol was added N-methylaniline (0.026 g, 0.240 mmol). The reaction was heated at reflux for 96 hours. After cooling to room temperature, the solution was concentrated. The residue was purified by column chromatography eluting with hexanes: ethyl acetate to yield 0.029 g (34%) of an orange solid. MS m/z 359 ($M^+$+1).

EXAMPLE 21

Preparation of 4-Aminoindenopyridine 19 ($R_1$=$CO_2Me$; $R_4$=Me; $R_6$=H; $R_7$=cyclopentyl) by Palladium Catalyzed Coupling A mixture of 4-chloroindenopyridine 18 (0.100 g, 0.347 mmol), cyclopentylamine (0.035 g, 0.416 mmol), palladium (II) acetate (0.004 g, 0.0017 mmol), 2-(di-t-butylphosphino)biphenyl (0.010 g, 0.0035 mmol), and cesium carbonate (0.124 g, 0.382 mmol) in 10 mL of dioxane was heated at reflux overnight. The reaction was cooled to room temperature, diluted with water, and extracted with ethyl acetate (3×35 mL). The combined organics were washed with brine, dried over $Na_2SO_4$, and concentrated. The residue was purified by column chromatography eluting with ethyl acetate: hexanes. The purified oil was dissolved in ether and cooled to 0° C. To this solution was slowly added 1.0 M HCl in ether. The resulting precipitate was isolated by filtration, washed with ether, and dried under vacuum to yield 0.032 g (25%) of a yellow solid. MS m/z 359 ($M^+$+23), 337 ($M^+$+1).

EXAMPLE 22

Preparation of Dihydropyridine 21 ($R_1$=$CO_2Me$; $R_2$=2-furyl; $R_3$=H; $R_4$=$NH_2$)

Unsaturated cyanoester 20 (0.20g, 1.10 mmol), enamine 21 (0.20g, 0.75 mmol) and 5 drops of triethylamine were refluxed in 1-propanol (4 mL). After 3 hours, the reaction was concentrated to half the volume and cooled. The resulting precipitate was filtered and washed with 1-propanol. The precipitate was a mixture of products and therefore was combined with the filtrate and concentrated. Purification by column chromatography, eluting with ethyl acetate: hexane yielded 0.11 g (34%) of the red product 22. MS m/z465 ($M^+$+23).

EXAMPLE 23

DDQ Oxidation/Deprotection of Dihydropyridine 22 ($R_1$=$CO_2Me$; $R_2$=3-furyl; $R_3$=H; $R_4$=$NH_2$)

To a solution of dihydropyridine 22(0.05 g, 0.11 mmol) in chlorobenzene (4 mL) was added 2,3-dichloro-3,6-dicyano-1,4-benzoquinone (0.05g, 0.22 mmol). The reaction was refluxed overnight before cooling to room temperature and diluting with diethyl ether. The reaction mixture was filtered through celite and concentrated in vacuo. Purification by column chromatography, eluting with ethyl acetate:hexane yielded 0.018 g (52%) of yellow product 23. MS m/z 343 ($M^+$+23), 321 ($M^+$+1).

Following the general synthetic procedures outlined above and in Examples 1–21, the compounds of Table 1 below were prepared.

TABLE 1
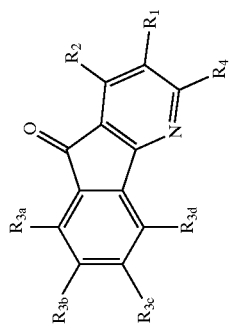
Ia
| No. | R₁ | R₂ | R₃ₐ | R₃ᵦ | R₃ᵧ | R₃ᵨ | R₄ | MS (M+1) |
|---|---|---|---|---|---|---|---|---|
| 1 | CN | C₇H₅O₂ (benzo[1,3]dioxol-5-yl) | H | H | H | H | Me | 341 |
| 2 | CO₂Et | C₇H₅O₂ (benzo[1,3]dioxol-5-yl) | H | H | H | H | Me | 388 |
| 3 | CO₂-t-Bu | C₇H₅O₂ (benzo[1,3]dioxol-5-yl) | H | H | H | H | Me | 416 |

TABLE 1-continued

Ia
| No. | R₁ | R₂ | R₃ₐ | R₃ᵦ | R₃c | R₃d | R₄ | MS (M + 1) |
|---|---|---|---|---|---|---|---|---|
| 4 | CO₂t-Bu |  C₈H₉O₂ | H | H | H | H | Me | 432 |
| 5 | CO₂Et |  C₆H₄NO₂ | H | H | H | H | Me | 389 |
| 6 | CO₂H |  C₇H₅O₂ | H | H | H | H | Me | 360 |

TABLE 1-continued

Ia

| No. | R₁ | R₂ | R₃ₐ | R₃ᵦ | R₃c | R₃d | R₄ | MS (M + 1) |
|---|---|---|---|---|---|---|---|---|
| 7 | CO₂Et | 4-benzyloxy-3-methoxyphenyl (C₁₄H₁₃O₂) | H | H | H | H | Me | 480 |
| 8 | CO₂Et | 3-bromo-4,5-dimethoxyphenyl (C₈H₈BrO₂) | H | H | H | H | Me | 482 |

TABLE 1-continued
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 9 | $CO_2Et$ | 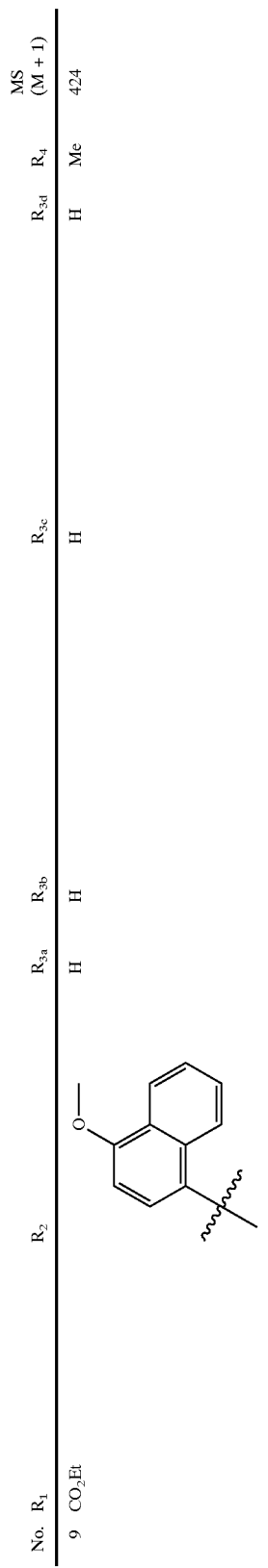 $C_{11}H_9O$ | H | H | H | H | Me | 424 |
| 10 | $CO_2H$ |  $C_8H_9O_2$ | H | H | H | H | Me | 376 |
| 11 | $CO_2Et$ | Ph | H | H | H | H | Me | 344 |

TABLE 1-continued

| No. | R1 | R2 | R3a | R3b | R3c | R3d | R4 | MS (M+1) |
|---|---|---|---|---|---|---|---|---|
| 12 | CO2Et | 4-methoxyphenyl-C(Me)- (C7H7O) | H | H | H | H | Me | 374 |
| 13 | CO2Et | 3,4,5-trimethoxyphenyl-C(Me)- (C9H11O3) | H | H | H | H | Me | 434 |
| 14 | CO2Et | 3-bromo-4,5-dihydroxyphenyl-C(Me)- (C6H4BrO2) | H | H | H | H | Me | 454 |

TABLE 1-continued
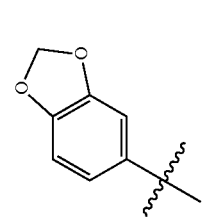
| No. | R₁ | R₂ | R₃ₐ | R₃ᵦ | R₃c | R₃d | R₄ | MS (M + 1) |
|---|---|---|---|---|---|---|---|---|
| 15 | CO₂Bn | 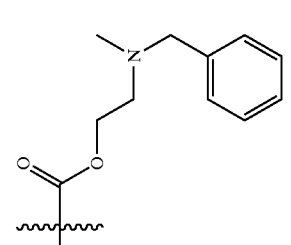 C₇H₅O₂ | H | H | H | H | Me | 450 |
| 16 | (structure) C₁₁H₁₄NO₂ | (structure) C₇H₅O₂ | H | H | H | H | Me | 507 |

TABLE 1-continued
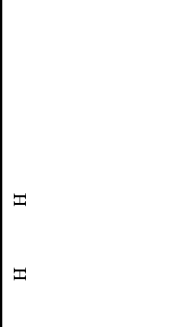
| No. | R₁ | R₂ | R₃ₐ | R₃b | R₃c | R₃d | R₄ | MS (M + 1) |
|---|---|---|---|---|---|---|---|---|
| 17 | CO₂Me | 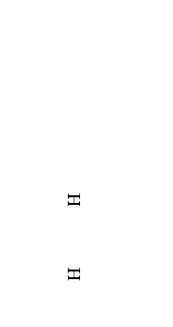 C₈H₉O₂ | H | H | H | H | Me | 390 |
| 18 | CO₂Me | 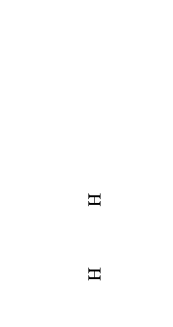 C₇H₅O₂ | H | H | H | H | Me | 374 |
| 19 | CO₂Et |  C₈H₉O₂ | H | H | H | H | Me | 404 |

TABLE 1-continued
| No. | R₁ | R₂ | R₃ₐ | R₃ᵦ | R₃c | R₃d | R₄ | MS (M + 1) |
|---|---|---|---|---|---|---|---|---|
| 20 | CO₂Et |  C₈H₉O₂ | H | H | H | H | Me | 404 |
| 21 | CO₂Et |  C₇H₆BrO | H | H | H | H | Me | 454 |
| 22 | CO₂Et |  C₇H₅O₂ | H | H | H | H | NH₂ | 411 (M + 23) |

TABLE 1-continued

Ia

| No. | R₁ | R₂ | | R₃ₐ | R₃ᵦ | R₃c | R₃d | R₄ | MS (M + 1) |
|---|---|---|---|---|---|---|---|---|---|
| 23 | CO₂Et | benzo[1,3]dioxol-4-yl (C₇H₅O₂) | | H | H | H | H | Me | 388 |
| 25 | CO₂Et | 3,4-dimethoxyphenyl (C₈H₉O₂) | | H | H | H | H | NH₂ | 405 |
| 26 | CO₂Et | 4-nitrophenyl (C₆H₄NO₂) | | H | H | H | H | NH₂ | 390 |

TABLE 1-continued

Ia

| No. | R₁ | R₂ | R₃ₐ | R₃ᵦ | R₃ᵧ | R₃ᵨ | R₄ | MS (M+1) |
|---|---|---|---|---|---|---|---|---|
| 27 | $CO_2Et$ | Ph | H | H | H | H | $NH_2$ | 345 |
| 28 | $CO_2Et$ | $C_9H_{11}O$ (4-methoxy-2,3-dimethylphenyl) | H | H | H | H | Me | 402 |
| 29 | $CO_2Et$ | $C_8H_8BrO_2$ (4-bromo-3,5-dimethoxyphenyl) | H | H | H | H | Me | 483 |
| 30 | $CO_2Me$ | Ph | H | H | H | H | Me | 330 |

TABLE 1-continued
Ia
| No. | R₁ | R₂ | R₃ₐ | R₃ᵦ | R₃c | R₃d | R₄ | MS (M + 1) |
|---|---|---|---|---|---|---|---|---|
| 31 | CO₂Et | 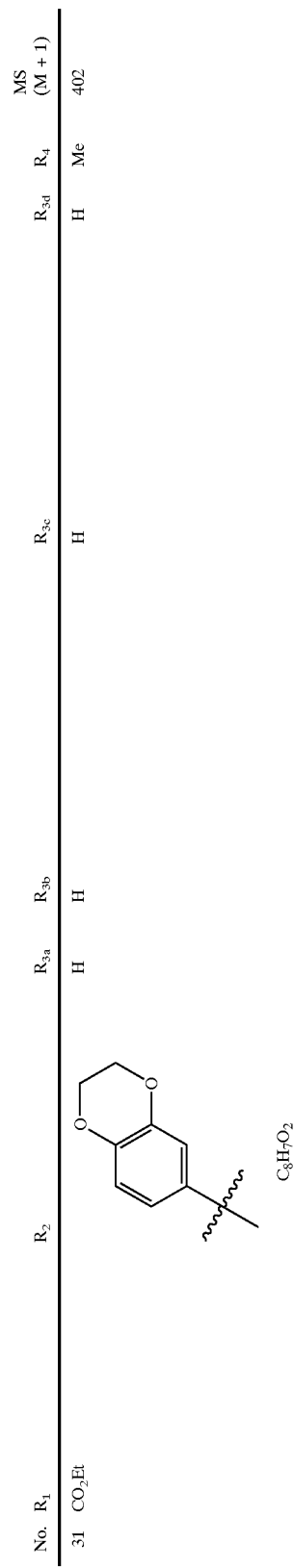 C₈H₇O₂ | H | H | H | H | Me | 402 |
| 32 | CO₂Et | C₇H₅O₂ | H | NO₂ | H | H | Me | 433 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 33 | C₄H₄NO₂ (2-cyanoethyl methyl ester group) | C₇H₅O₂ (benzo[1,3]dioxol-5-yl-methyl) | H | H | H | H | Me | 413 |
| 34 | CO₂Et | C₇H₄NO₄ (6-nitro-benzo[1,3]dioxol-5-yl-methyl) | H | H | H | H | Me | 433 |

TABLE 1-continued
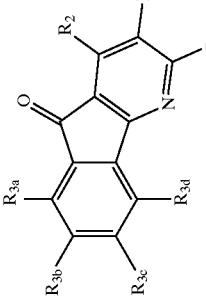
Ia
| No. | R₁ | R₂ | R₃ₐ | R₃ᵦ | R₃c | R₃d | R₄ | MS (M + 1) |
|---|---|---|---|---|---|---|---|---|
| 35 | CO₂Et | 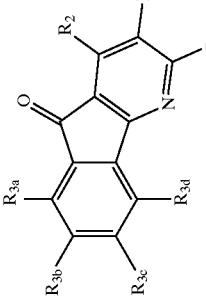 C₇H₅O₂ | H | H | NO₂ | H | Me | 433 |
| 36 | CO₂Me | 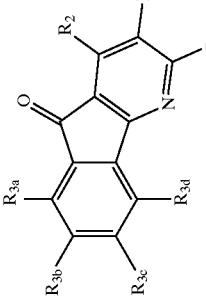 C₇H₄F₃ | H | H | H | H | Me | 398 |
| 37 | CO₂Et | 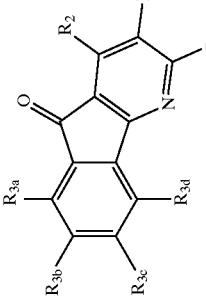 C₇H₅O₂ | H | H | NH₂ | H | Me | 403 |

TABLE 1-continued
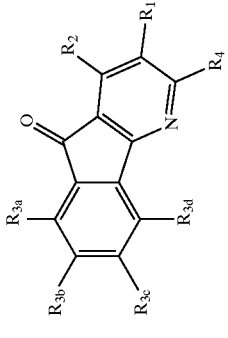
Ia
| No. | R1 | R2 | R3a | R3b | R3c | R3d | R4 | MS (M+1) |
|---|---|---|---|---|---|---|---|---|
| 38 | CONH2 | 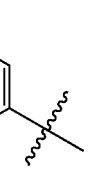 C7H5O2 | H | H | H | H | Me | 359 |
| 39 | CO2Et | C8H9 | H | H | H | H | Me | 372 |
| 40 | CO2Et | 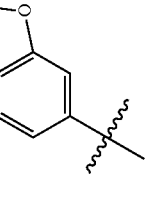 C7H5O2 | H | NH2 | H | H | Me | 403 |

TABLE 1-continued
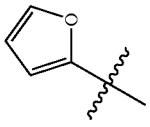
Ia
| No. | $R_1$ | $R_2$ | | $R_{3a}$ | $R_{3b}$ | $R_{3c}$ | $R_{3d}$ | $R_4$ | MS (M + 1) |
|---|---|---|---|---|---|---|---|---|---|
| 41 | $CO_2Et$ | 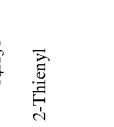 $C_4H_3O$ | | H | H | H | H | Me | 334 |
| 42 | $CO_2Et$ | 2-Thienyl | | H | H | H | H | Me | 350 |
| 43 | $CO_2Me$ | 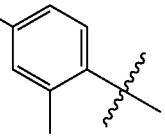 $C_8H_9$ | | H | H | H | H | Me | 358 |
| 44 | $CO_2Me$ | 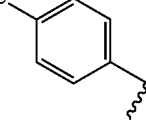 $C_8H_7O_2$ | | H | H | H | H | Me | 388 |

TABLE 1-continued

Ia (structure shown: tricyclic indeno-pyridinone with substituents R1, R2, R4 on pyridine ring and R3a, R3b, R3c, R3d on benzene ring)

| No. | R1 | R2 | R3a | R3b | R3c | R3d | R4 | MS (M + 1) |
|---|---|---|---|---|---|---|---|---|
| 45 | CO2Me | 6-nitro-benzo[1,3]dioxol-5-yl-methyl (C7H4NO4) | H | H | H | H | Me | 419 |
| 46 | CO2Me | 4-methoxy-2,3-dimethylphenyl-methyl (C9H11O) | H | H | H | H | Me | 388 |
| 47 | CO2Me | 4-Pyridyl | H | H | H | H | Me | 331 |
| 48 | CO2Me | benzo[1,3]dioxol-4-yl-methyl (C7H5O2) | H | H | H | H | Me | 374 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 49 | CO₂Me | 6-bromo-1,3-benzodioxol-5-yl (C₇H₄BrO₂) | H | H | H | H | Me | 454 |
| 50 | CO₂Me | 5-bromo-2-methoxyphenyl (C₇H₆BrO) | H | H | H | H | Me | 439 |

TABLE 1-continued
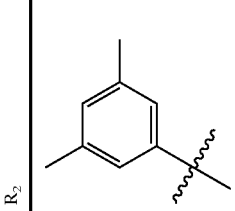
Ia
| No. | R1 | R2 | R3a | R3b | R3c | R3d | R4 | MS (M + 1) |
|---|---|---|---|---|---|---|---|---|
| 51 | CO2Me | 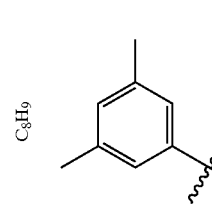 C8H9 | H | H | H | H | Me | 358 |
| 52 | CO2Et | 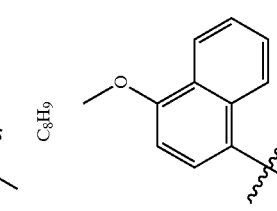 C8H9 | H | H | H | H | Me | 372 |
| 53 | CO2Me |  C11H9O | H | H | H | H | Me | 410 |

TABLE 1-continued
Ia
| No. | R₁ | R₂ | R₃ₐ | R₃ᵦ | R₃c | R₃d | R₄ | MS (M + 1) |
|---|---|---|---|---|---|---|---|---|
| 54 | CO₂Me |  C₆H₄NO₂ | H | H | H | H | Me | 375 |
| 55 | CO₂Et | 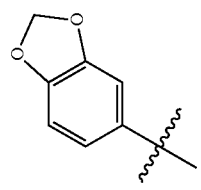 C₇H₅O₂ | H | NHAc | H | H | Me | 445 |

TABLE 1-continued

[Structure Ia: tricyclic indeno-pyridinone with R1, R2, R3a, R3b, R3c, R3d, R4 substituents]

| No. | R1 | R2 | R3a | R3b | R3c | R3d | R4 | MS (M + 1) |
|---|---|---|---|---|---|---|---|---|
| 56 | CO₂Et | benzo[d][1,3]dioxol-5-yl-C(CH₃)- (C₇H₅O₂) | H | H | NHAc | H | Me | 445 |
| 57 | CO₂Et | (3-methylphenyl)-C(CH₃)- (C₇H₇) | H | H | H | H | Me | 358 |
| 58 | CO₂Et | (2-methylphenyl)-C(CH₃)- (C₇H₇) | H | H | H | H | Me | 358 |

TABLE 1-continued
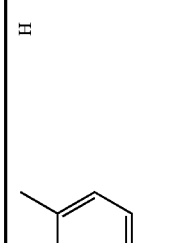
Ia
| No. | $R_1$ | $R_2$ | | $R_{3a}$ | $R_{3b}$ | $R_{3c}$ | $R_{3d}$ | $R_4$ | MS (M + 1) |
|---|---|---|---|---|---|---|---|---|---|
| 59 | $CO_2Et$ | 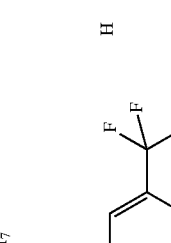 | $C_7H_7$ | H | H | H | H | Me | 358 |
| 60 | $CO_2Et$ | 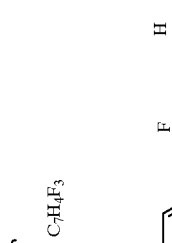 | $C_7H_4F_3$ | H | $NO_2$ | H | H | Me | 457 |
| 61 | $CO_2Et$ | 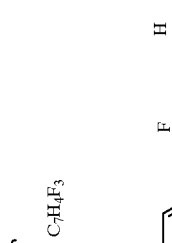 | $C_7H_4F_3$ | H | H | $NO_2$ | H | Me | 457 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 62 | CO₂Me | 2-methylphenyl-CH(CH₃)- (C₇H₇) | H | H | H | H | Me | 344 |
| 63 | CO₂Et | 3-(trifluoromethyl)phenyl-CH(CH₃)- (C₇H₄F₃) | H | NH₂ | H | H | Me | 427 |
| 64 | CO₂Et | 3-(trifluoromethyl)phenyl-CH(CH₃)- (C₇H₄F₃) | H | H | NH₂ | H | Me | 427 |

TABLE 1-continued

Ia

| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 65 | CO$_2$Me | 3,5-bis(trifluoromethyl)phenyl-C(CH$_3$)- (C$_8$H$_3$F$_6$) | H | H | H | H | Me | 466 |
| 66 | CO$_2$Me | 4-methylphenyl-C(CH$_3$)- (C$_7$H$_7$) | H | H | H | H | Me | 344 |
| 67 | CO$_2$Me | 3-methylphenyl-C(CH$_3$)- (C$_7$H$_7$) | H | H | H | H | Me | 344 |

TABLE 1-continued
Ia
| No. | R₁ | R₂ | R₃ₐ | R₃ᵦ | R₃c | R₃d | R₄ | MS (M + 1) |
|---|---|---|---|---|---|---|---|---|
| 68 | CO₂Me |  C₇H₄F₃ | H | NO₂ | H | H | Me | 443 |
| 69 | CO₂Me |  C₇H₄F₃ | H | H | NO₂ | H | Me | 443 |
| 70 | CO₂Et |  C₈H₉ | H | H | H | H | i-Pr | 400 |

TABLE 1-continued

Ia (structure shown with R1, R2, R3a-d, R4 substituents on the fused ring system)

| No. | R1 | R2 | R3a | R3b | R3c | R3d | R4 | MS (M + 1) |
|---|---|---|---|---|---|---|---|---|
| 71 | CO$_2$Me | C$_7$H$_4$F$_3$ (3-trifluoromethylphenyl) | H | NH$_2$ | H | H | Me | 413 |
| 72 | CO$_2$Me | C$_6$H$_3$Cl$_2$ (3,5-dichlorophenyl) | H | H | H | H | Me | 399 |
| 73 | CO$_2$Me | C$_8$H$_9$ (2,4-dimethylphenyl) | H | H | H | H | Et | 372 |

TABLE 1-continued

Ia (structure shown with R₁, R₂, R₃ₐ, R₃ᵦ, R₃ᵧ, R₃ᵨ, R₄ substituents on indeno-pyridinone core)

| No. | R₁ | R₂ | R₃ₐ | R₃ᵦ | R₃ᵧ | R₃ᵨ | R₄ | MS (M + 1) |
|---|---|---|---|---|---|---|---|---|
| 74 | $CO_2Me$ | 4-(trifluoromethyl)phenyl, $C_7H_4F_3$ | H | H | H | H | Me | 398 |
| 75 | $CO_2Me$ | 6-methylnaphth-2-yl, $C_{11}H_9$ | H | H | H | H | Me | 394 |

TABLE 1-continued
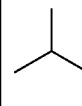
Ia
| No. | R₁ | R₂ | | R₃ₐ | R₃ᵦ | R₃ᵧ | R₃d | R₄ | MS (M + 1) |
|---|---|---|---|---|---|---|---|---|---|
| 76 | CO₂Me | 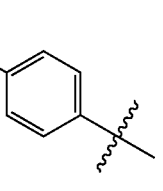 | C₉H₁₁ | H | H | H | H | Me | 372 |
| 77 | CO₂Me | 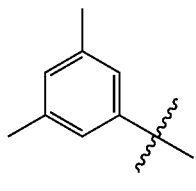 | C₈H₉ | H | NO₂ | H | H | Me | 403 |
| 78 | CO₂Me | 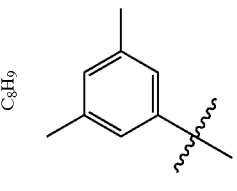 | C₈H₉ | H | H | NO₂ | H | Me | 403 |

TABLE 1-continued
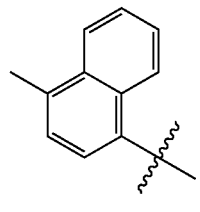
| No. | R₁ | R₂ | | R₃ₐ | R₃ᵦ | R₃꜀ | R₃d | R₄ | MS (M+1) |
|---|---|---|---|---|---|---|---|---|---|
| 79 | CO₂Me | 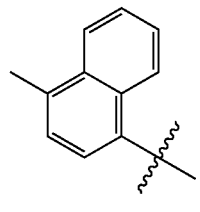 | C₁₁H₉ | H | H | H | H | Me | 394 |
| 80 | CO₂Me | 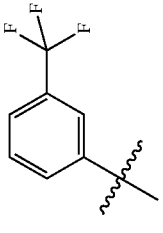 | C₇H₄F₃ | H | NHAc | H | H | Me | 455 |
| 81 | CO₂Me | 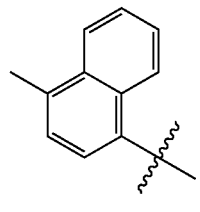 | C₆H₃Br₂ | H | H | H | H | Me | 488 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 82 | CO₂Me | 3,5-dimethylphenyl-C(CH₃)- (C₈H₉) | H | NH₂ | H | H | Me | 373 |
| 83 | CO₂Me | 3,5-dimethylphenyl-C(CH₃)- (C₈H₉) | H | H | NH₂ | H | Me | 373 |
| 84 | CO₂Me | 3-fluoro-2-methylphenyl-C(CH₃)- (C₇H₆F) | H | H | H | H | Me | 362 |

TABLE 1-continued

Ia

| No. | R₁ | R₂ | | R₃ₐ | R₃ᵦ | R₃c | R₃d | R₄ | MS (M+1) |
|-----|-----|-----|-----|-----|-----|-----|-----|-----|------|
| 85 | CO₂Me | 3-bromophenyl (C₆H₄Br) | | H | H | H | H | Me | 431 (M+23) |
| 86 | CO₂Me | 1-naphthyl (C₁₀H₇) | | H | H | H | H | Me | 380 (M+23) |
| 87 | CO₂Me | 4-methyl-1-naphthyl (C₁₁H₉) | | H | NO₂ | H | H | Me | 439 |

TABLE 1-continued

Ia (structure shown with R1, R2, R3a, R3b, R3c, R3d, R4 substituents on a fused ring system with a ketone and pyridine nitrogen)

| No. | R1 | R2 | R3a | R3b | R3c | R3d | R4 | MS (M + 1) |
|-----|------|------|-----|-----|-----|-----|-----|------------|
| 88 | CO2Me | 4-methylnaphthyl (C11H9) | H | H | NO2 | H | Me | 439 |
| 89 | CO2Me | phenanthryl (C14H9) | H | H | H | H | Me | 430 |

TABLE 1-continued

Ia

| No. | R₁ | R₂ | R₃a | R₃b | R₃c | R₃d | R₄ | MS (M + 1) |
|---|---|---|---|---|---|---|---|---|
| 90 | CO₂Me | 4-methylnaphthalen-1-yl (C₁₁H₉) | H | NH₂ | H | H | Me | 409 |
| 91 | CO₂Me | 4-methylnaphthalen-1-yl (C₁₁H₉) | H | H | NH₂ | H | Me | 409 |
| 92 | 2-cyanoethyl 2-methylpropanoate (C₄H₄NO₂) | 2,4-dimethylphenyl (C₈H₉) | H | H | H | H | Me | 397 |

TABLE 1-continued

Ia (structure shown with R1, R2, R3a–R3d, R4 substituents on an indeno-pyridinone core)

| No. | R1 | R2 | R3a | R3b | R3c | R3d | R4 | MS (M + 1) |
|---|---|---|---|---|---|---|---|---|
| 93 | CN | 2,4-dimethylphenyl-C(Me)-, C8H9 | H | H | H | H | Me | 325 |
| 94 | CO2Me | 2,4-dimethylphenyl-C(Me)-, C8H9 | H | H | H | H | NH2 | 359 |
| 95 | CO2Me | 4-methylnaphthyl-C(Me)-, C11H9 | H | H | H | H | NH2 | 395 |

TABLE 1-continued

Ia
[structure: tricyclic indeno-pyridinone core with substituents R1, R2, R3a, R3b, R3c, R3d, R4]

| No. | R1 | R2 | R3a | R3b | R3c | R3d | R4 | MS (M+1) |
|---|---|---|---|---|---|---|---|---|
| 96 | CO2H | 2,4-dimethylphenyl (C8H9) | H | H | H | H | Me | 344 |
| 97 | -C(Me)-O-C(O)-CH2CH2-C≡N (C4H4NO2) | 4-methylnaphthyl (C11H9) | H | H | H | H | Me | 433 |

TABLE 1-continued

| No. | R1 | R2 | R3a | R3b | R3c | R3d | R4 | MS (M + 1) |
|---|---|---|---|---|---|---|---|---|
| 98 | CN | (4-methylnaphthalen-1-yl)methyl, C11H9 | H | H | H | H | Me | 361 |
| 99 | (acetoxy), C2H2O2 | (benzo[d][1,3]dioxol-5-yl), C7H5O2 | H | H | H | H | C2H2O2 | 358 |

TABLE 1-continued
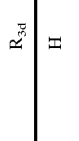
| No. | R₁ | R₂ | R₃ₐ | R₃ᵦ | R₃c | R₃d | R₄ | MS (M+1) |
|---|---|---|---|---|---|---|---|---|
| 100 |  C₂H₂O₂ |  C₈H₁₀N | H | H | H | H | C₂H₂O₂ | 357 |
| 101 |  C₂H₂O₂ | Ph | H | H | H | H | C₂H₂O₂ | 314 |
| 102 | 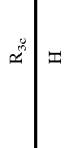 C₂H₂O₂ | p-C₆H₄NO₂ | H | H | H | H | C₂H₂O₂ | 361 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 103 | (ester group) C₂H₂O₂ | naphthyl C₁₀H₇ | H | H | H | H | C₂H₂O₂ | 364 |
| 104 | (ester group) C₂H₂O₂ | 3,5-dimethylphenyl C₈H₉ | H | H | H | H | C₂H₂O₂ | 342 |
| 105 | CO₂H | 4-methylnaphthyl C₁₁H₉ | H | H | H | H | Me | 380 |

TABLE 1-continued
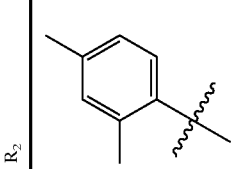
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 106 | CONH$_2$ | 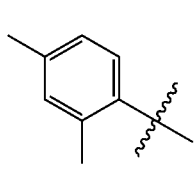 C$_8$H$_9$ | H | H | H | H | Me | 343 |
| 107 | CONHMe | 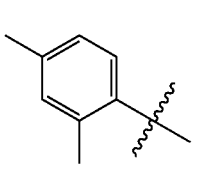 C$_8$H$_9$ | H | H | H | H | Me | 357 |
| 108 | CONMe$_2$ | 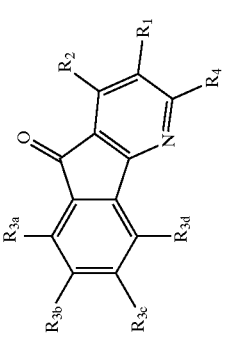 C$_8$H$_9$ | H | H | H | H | Me | 371 |

TABLE 1-continued
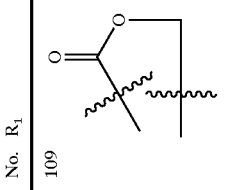
Ia
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 109 | 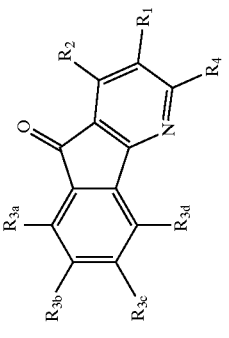 C$_2$H$_2$O$_2$ | 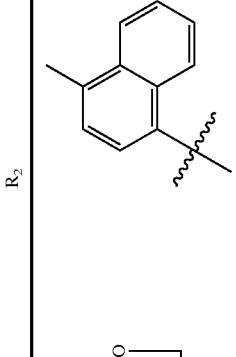 C$_{11}$H$_9$ | H | H | H | H | C$_2$H$_2$O$_2$ | 378 |
| 110 | 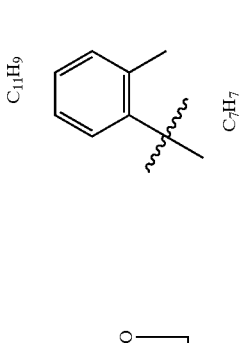 C$_2$H$_2$O$_2$ | 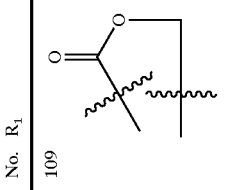 C$_7$H$_7$ | H | H | H | H | C$_2$H$_2$O$_2$ | 328 |
| 111 | 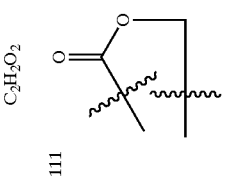 C$_2$H$_2$O$_2$ |  C$_9$H$_{11}$ | H | H | H | H | C$_2$H$_2$O$_2$ | 356 |

TABLE 1-continued
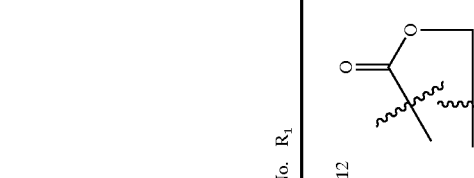
| No. | R₁ | R₂ | R₃ₐ | R₃ᵦ | R₃c | R₃d | R₄ | MS (M + 1) |
|---|---|---|---|---|---|---|---|---|
| 112 | 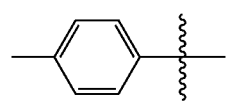 C₂H₂O₂ | 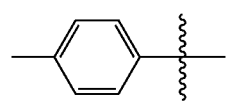 C₇H₇ | H | H | H | H | C₂H₂O₂ | 328 |
| 113 | CO₂Me | 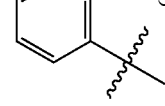 C₆H₄NO₂ | H | H | H | H | Me | 375 |
| 114 | 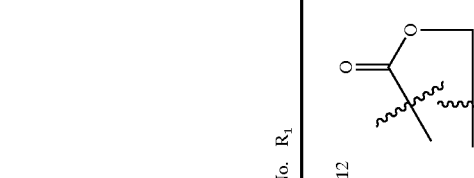 C₂H₂O₂ | 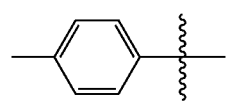 C₇H₇ | H | H | H | H | C₂H₂O₂ | 328 |

TABLE 1-continued
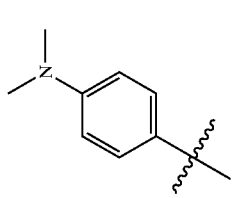
| No. | R₁ | R₂ | R₃ₐ | R₃ᵦ | R₃꜀ | R₃d | R₄ | MS (M+1) |
|---|---|---|---|---|---|---|---|---|
| 115 | CO₂Me | 4-(dimethylamino)phenyl, C₈H₁₀N | H | H | H | H | Me | 373 |
| 116 | CONH₂ | 4-methylnaphthalen-1-yl, C₁₁H₉ | H | H | H | H | Me | 379 |
| 117 | 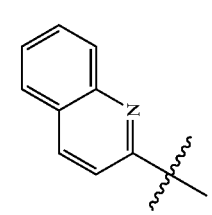 C₂H₂O₂ | quinolin-2-yl, C₉H₆N | H | H | H | H | C₂H₂O₂ | 365 |

TABLE 1-continued
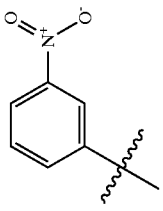
| No. | R1 | R2 | R3a | R3b | R3c | R3d | R4 | MS (M + 1) |
|---|---|---|---|---|---|---|---|---|
| 118 | CO2Me | 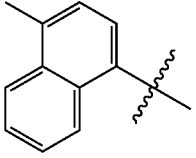 C6H4NO2 | H | H | H | H | Me | 375 |
| 119 | CONHMe | 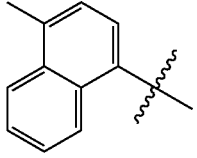 C11H9 | H | H | H | H | Me | 393 |
| 120 | CONMe2 |  C11H9 | H | H | H | H | Me | 407 |

TABLE 1-continued

Ia (structure shown with R1, R2, R3a, R3b, R3c, R3d, R4 substituents on indenopyridinone core)

| No. | R1 | R2 | R3a | R3b | R3c | R3d | R4 | MS (M + 1) |
|---|---|---|---|---|---|---|---|---|
| 121 | CO2Me | quinolin-4-yl-C(Me)2- (C9H6N) | H | H | H | H | Me | 381 |
| 122 | CO2Me | 4-methylnaphthalen-1-yl-C(Me)2- (C11H9) | H | Cl | Cl | H | Me | 463 |
| 123 | CO2Me | 3,5-dimethylphenyl-C(Me)2- (C8H9) | H | Cl | Cl | H | Me | 427 |

TABLE 1-continued
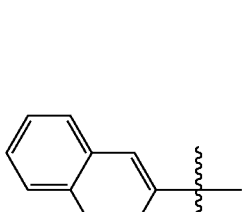
| No. | R₁ | R₂ | R₃ₐ | R₃ᵦ | R₃꜀ | R₃ᵈ | R₄ | MS (M + 1) |
|---|---|---|---|---|---|---|---|---|
| 124 | CO₂Me | 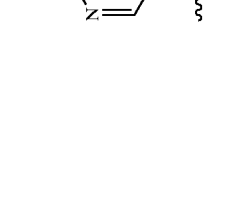 C₉H₆N | H | H | H | H | Me | 381 |
| 125 | CO₂Et | C₁₁H₉ | H | H | H | H | Me | 408 |

TABLE 1-continued

Ia

| No. | R₁ | R₂ | | R₃ₐ | R₃ᵦ | R₃c | R₃d | R₄ | MS (M + 1) |
|---|---|---|---|---|---|---|---|---|---|
| 126 | CO₂Me | 3,5-dibromophenyl-C(Me)- | C₆H₃Br₂ | H | Cl | Cl | H | Me | 555 |
| 127 | CO₂Me | 3,5-dimethylphenyl-C(Me)- | C₈H₉ | Cl | H | H | Cl | Me | 427 |
| 128 | CO₂Me | 2-NO₂-4,5-OCH₂O—C₆H₂ | | H | H | H | H | Me | 421 |

TABLE 1-continued
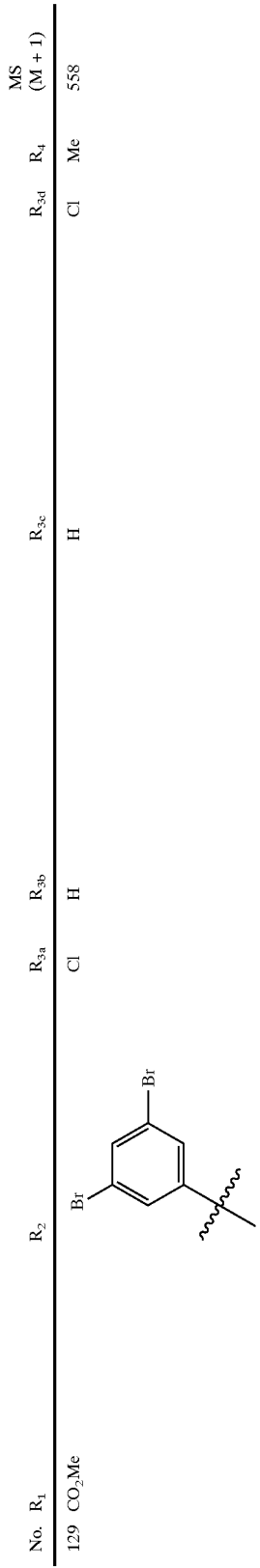
| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 129 | $CO_2Me$ | 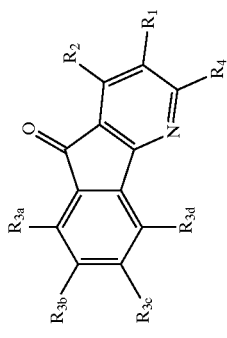 $C_6H_3Br_2$ | Cl | H | H | Cl | Me | 558 |
| 130 | $CO_2Me$ |  $C_6H_6N$ | H | H | H | H | Me | 345 |
| 131 | $CO_2Et$ | 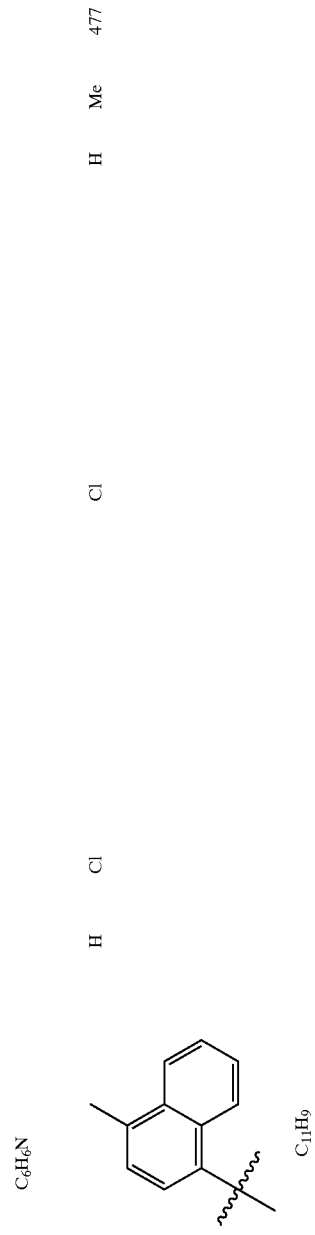 $C_{11}H_9$ | H | Cl | Cl | H | Me | 477 |

TABLE 1-continued

Ia

| No. | R₁ | R₂ | | R₃ₐ | R₃ᵦ | R₃c | R₃d | R₄ | MS (M + 1) |
|---|---|---|---|---|---|---|---|---|---|
| 132 | CO₂Me | 2-NH₂-3,5-dibromophenyl-C(Me)₂- | C₆H₄Br₂N | H | H | H | H | Me | 503 |
| 133 | Ac | 3,5-dibromophenyl-C(Me)₂- | C₆H₃Br₂ | H | H | H | H | Me | 472 |
| 134 | Ac | 3,5-dimethylphenyl-C(Me)₂- | C₈H₉ | H | H | H | H | Me | 342 |

TABLE 1-continued
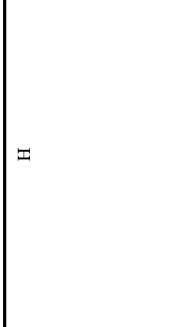
Ia
| No. | R1 | R2 | R3a | R3b | R3c | R3d | R4 | MS (M + 1) |
|---|---|---|---|---|---|---|---|---|
| 135 | CO2Me | 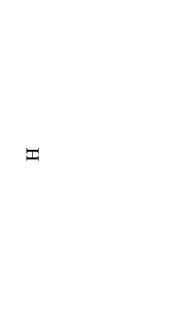 C5H4N | H | H | H | H | Me | 331 |
| 136 |  C4H4NO2 | 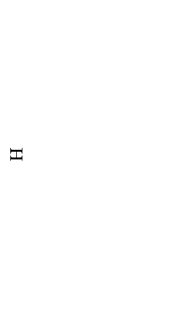 C6H3Br2 | H | H | H | H | Me | 527 |
| 137 |  C4H4NO2 |  C8H9 | H | H | H | H | Me | 397 |

TABLE 1-continued
Ia
| No. | R₁ | R₂ | R₃ₐ | R₃ᵦ | R₃c | R₃d | R₄ | MS (M + 1) |
|---|---|---|---|---|---|---|---|---|
| 138 | CO₂Me | 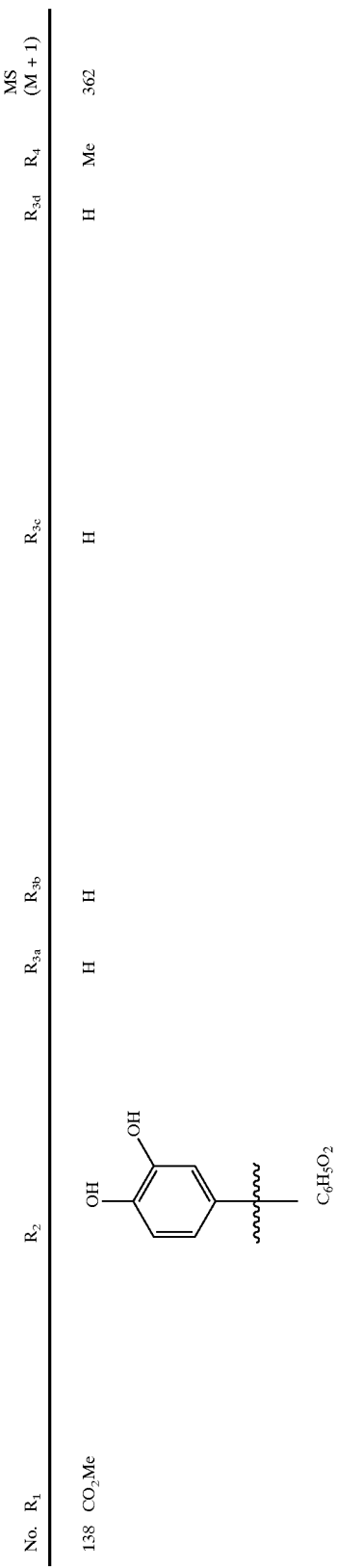 C₆H₅O₂ | H | H | H | H | Me | 362 |
| 139 | CO₂H | 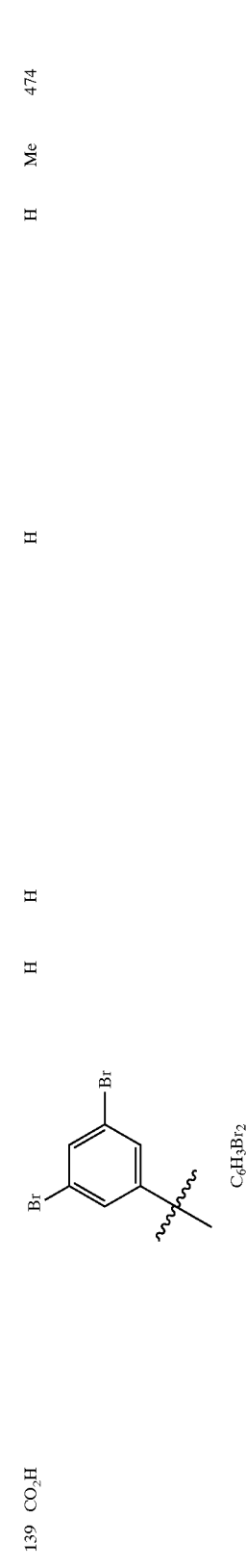 C₆H₃Br₂ | H | H | H | H | Me | 474 |

TABLE 1-continued
| No. | R₁ | R₂ | R₃ₐ | R₃ᵦ | R₃c | R₃d | R₄ | MS (M + 1) |
|---|---|---|---|---|---|---|---|---|
| 140 | CO₂H |  C₈H₉ | H | H | H | H | Me | 344 |
| 141 | CO₂Me |  C₆H₅O | H | H | H | H | Me | 346 |
| 142 | CO₂Me |  C₁₀H₇ | H | H | H | H | Me | 380 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 143 | CO₂Me | —O—C₆H₄—(CH₂)₈CH₃ (C₁₆H₂₅O) | H | H | H | H | Me | 486 |
| 144 | CO₂Me | 3-(benzyloxy)phenyl (C₁₃H₁₁O) | H | H | H | H | Me | 436 |

TABLE 1-continued
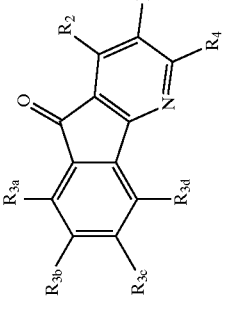
| No. | R₁ | R₂ | R₃ₐ | R₃ᵦ | R₃c | R₃d | R₄ | MS (M+1) |
|---|---|---|---|---|---|---|---|---|
| 145 | CO₂Me | 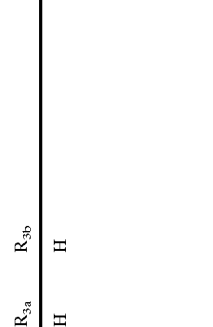 C₇H₅Br₂O | H | H | H | H | Me | 518 |
| 146 | 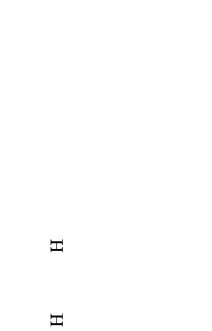 C₄H₄NO₂ |  C₇H₅Br₂O | H | H | H | H | Me | 557 |
| 147 |  C₄H₄NO₂ |  C₈H₉ | H | Cl | Cl | H | Me | 466 |

TABLE 1-continued

Ia: [structure: tricyclic indeno-pyridinone with substituents R1, R2, R3a, R3b, R3c, R3d, R4]

| No. | R1 | R2 | R3a | R3b | R3c | R3d | R4 | MS (M + 1) |
|-----|------|------|-----|-----|-----|-----|----|------------|
| 148 | CO2Et | —NHPh | H | H | H | H | Me | 359 |
| 149 | CO2Me | 2-methoxyphenyl (C7H7O) | H | H | | H | Me | 360 |
| 150 | CO2Me | 3,5-dibromo-4-hydroxyphenyl (C6H3Br2O) | H | H | H | H | Me | 504 |
| 151 | | quinolin-3-yl with 2-cyanoethyl ester linker (C9H6N / C4H4NO2) | H | H | | H | Me | 420 |

TABLE 1-continued

Ia

| No. | R₁ | R₂ | R₃ₐ | R₃ᵦ | R₃ᵧ | R₃ₐ | R₄ | MS (M + 1) |
|---|---|---|---|---|---|---|---|---|
| 152 | C₃H₅O₃ | C₆H₃Br₂O | H | H | H | H | Me | 534 |
| 153 | C₄H₄NO₂ | C₆H₅O | H | H | H | H | Me | 385 |
| 154 | C₂H₄NO₂ | C₈H₉ | H | H | H | H | Me | 373 |

TABLE 1-continued

Ia (structure with R1, R2, R3a, R3b, R3c, R3d, R4 substituents on a fused pyridine-indanone scaffold)

| No. | R1 | R2 | R3a | R3b | R3c | R3d | R4 | MS (M + 1) |
|---|---|---|---|---|---|---|---|---|
| 155 | CO₂Me attached via -C(Me)-OC(O)-CH₂CH₂-C≡N (C₄H₄NO₂) | 3,5-dibromophenyl-C(Me)- (C₆H₃Br₂) | H | H | NO₂ | H | Me | 574 |
| 156 | CO₂Me | 4-methylnaphthalen-1-yl-C(Me)- (C₁₁H₉) | H | Br | H | H | Me | 473 |
| 157 | CO₂Me | 4-methylnaphthalen-1-yl-C(Me)- (C₁₁H₉) | H | H | Br | H | Me | 473 |

TABLE 1-continued

Ia

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 158 | -C(O)OCH₂CH₂CN, C₄H₄NO₂ | 4-quinolinyl-C(CH₃)₂-, C₉H₆N | H | Cl | Cl | H | Me | 489 |
| 159 | -C(O)OCH₂CH₂CN, C₄H₄NO₂ | 3,5-dibromo-4-hydroxyphenyl-C(CH₃)₂-, C₆H₃Br₂O | H | H | NO₂ | H | Me | 590 |
| 160 | -C(O)OCH₂CH₂OH, C₃H₅O₃ | 4-quinolinyl-C(CH₃)₂-, C₉H₆N | H | H | H | H | Me | 411 |

TABLE 1-continued

| No. | R1 | R2 | R3a | R3b | R3c | R3d | R4 | MS (M + 1) |
|---|---|---|---|---|---|---|---|---|
| 161 | CO2Me | 3,5-dimethylphenyl-C(CH3)2- (C8H9) | H | Br | H | H | Me | 436 |
| 162 | CO2Me | 3,5-dimethylphenyl-C(CH3)2- (C8H9) | H | H | Br | H | Me | 438 |
| 163 | CO2Me | 3,5-dimethylphenyl-C(CH3)2- (C8H9) | H | Br | Br | H | Me | 516 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 164 | ⟨ester with CH₂CH₂CN group⟩ C₄H₄NO₂ | 3,5-dibromophenyl-C(CH₃)< C₆H₃Br₂ | H | Cl | Cl | H | Me | 597 |
| 165 | ⟨ester with CH₂CH₂OH group⟩ C₃H₅O₃ | quinolin-4-yl-C(CH₃)< C₉H₆N | H | Cl | Cl | H | Me | 480 |
| 166 | CO₂Me | 4-methylnaphthalen-1-yl-C(CH₃)< C₁₁H₉ | H | Br | Br | H | Me | 552 |

TABLE 1-continued
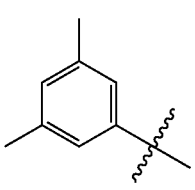
| No. | R1 | R2 | R3a | R3b | R3c | R3d | R4 | MS (M+1) |
|---|---|---|---|---|---|---|---|---|
| 167 | CO2Et | 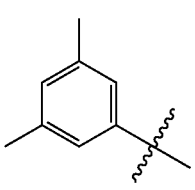 C8H9 | H | Br | Br | H | Me | 530 |
| 168 | CO2Me | 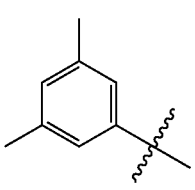 C6H3Br2O | F | H | H | F | Me | 540 |
| 169 | CO2Me | 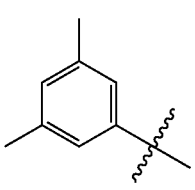 C6H3Br2O | H | H | NO2 | H | Me | 551 |

TABLE 1-continued

Ia

| No. | R₁ | R₂ | R₃ₐ | R₃ᵦ | R₃c | R₃d | R₄ | MS (M+1) |
|---|---|---|---|---|---|---|---|---|
| 170 | CO₂Me | 2,6-dibromo-4-hydroxyphenyl (C₆H₃Br₂O) | H | Cl | Cl | H | Me | 573 |
| 171 | -C(Me)(3,5-dimethylphenyl)- with 2-cyanoethyl ester (C₈H₉ / C₄H₄NO₂) | | H | H | NO₂ | H | Me | 444 |
| 172 | -C(Me)(3,5-dimethylphenyl)- with 2-cyanoethyl ester (C₈H₉ / C₄H₄NO₂) | | H | NO₂ | H | H | Me | 444 |

TABLE 1-continued

Ia

| No. | $R_1$ | $R_2$ | $R_{3a}$ | $R_{3b}$ | $R_{3c}$ | $R_{3d}$ | $R_4$ | MS (M + 1) |
|---|---|---|---|---|---|---|---|---|
| 173 | $CO_2Me$ | 3,5-dimethylphenyl, $C_8H_9$ | F | H | H | F | Me | 394 |
| 174 | ⌇C(Me)(−)C(=O)O−CH$_2$CH$_2$CN, $C_4H_4NO_2$ | 3,5-dimethylphenyl, $C_8H_9$ | F | H | H | F | Me | 433 |
| 175 | $CO_2Me$ | 3,5-dimethoxyphenyl, $C_8H_9O_2$ | H | Br | Br | H | Me | 548 |

TABLE 1-continued
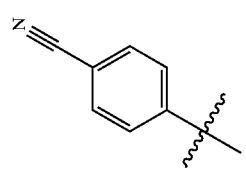
Ia
| No. | R₁ | R₂ | R₃ₐ | R₃ᵦ | R₃꜀ | R₃d | R₄ | MS (M + 1) |
|---|---|---|---|---|---|---|---|---|
| 176 | CO₂Me | 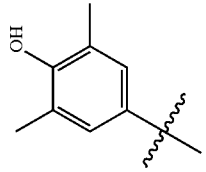 C₇H₄N | H | H | H | H | Me | 355 |
| 177 | CO₂Me | 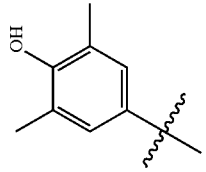 C₈H₉O | H | NO₂ | H | H | Me | 421 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 178 | CO₂Me | OH-2,6-diMe-4-C(Me)₂- (C₈H₉O) | H | H | NO₂ | H | Me | 453 (M+23) |
| 179 | CO₂Me | OH-2,6-diMe-4-C(Me)₂- (C₈H₉O) | H | Cl | Cl | H | Me | 443 |
| 180 | CN | OH-2,6-diMe-4-C(Me)₂- (C₈H₉O) | H | H | H | H | Me | 341 |

TABLE 1-continued
| No. | R1 | R2 | R3a | R3b | R3c | R3d | R4 | MS (M + 1) |
|---|---|---|---|---|---|---|---|---|
| 181 | CO2Me | 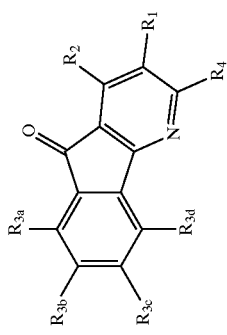 C6H3I2O | H | H | H | H | Me | 598 |
| 182 | CO2Me | 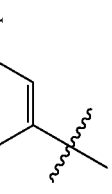 C6H3F2 | H | Cl | Cl | H | Me | 435 |

TABLE 1-continued

Ia

| No. | R₁ | R₂ | R₃ₐ | R₃ᵦ | R₃c | R₃d | R₄ | MS (M+1) |
|---|---|---|---|---|---|---|---|---|
| 183 | CO₂Et | 2,4-dimethylphenyl-NH- (C₈H₁₀N) | H | H | H | H | Me | 387 |
| 184 | CO₂Et | 3-methylphenyl-NH- (C₇H₈N) | H | H | H | H | Me | 373 |

TABLE 1-continued

[Structure Ia: tricyclic indeno-pyridinone with substituents R1, R2, R3a, R3b, R3c, R3d, R4]

| No. | R1 | R2 | R3a | R3b | R3c | R3d | R4 | MS (M + 1) |
|---|---|---|---|---|---|---|---|---|
| 185 | CO2Me | 3,5-diiodo-4-methoxyphenyl-C(Me)- (C7H5I2O) | H | H | H | H | Me | 612 |
| 186 | CO2Et | quinolin-8-ylamino-C(Me)- (C9H7N2) | H | H | H | H | Me | 410 |
| 187 | CO2Me | 3,5-diiodo-4-hydroxyphenyl-C(Me)- (C6H3I2O) | H | H | NO2 | H | Me | 345 |

TABLE 1-continued

Ia (structure shown: fused tricyclic with carbonyl, pyridine nitrogen, substituents R1, R2, R3a, R3b, R3c, R3d, R4)

| No. | R1 | R2 | R3a | R3b | R3c | R3d | R4 | MS (M+1) |
|---|---|---|---|---|---|---|---|---|
| 188 | CO2Me | 4-OH-3,5-diiodophenyl-C(Me)- (C6H3I2O) | H | Cl | Cl | H | Me | 668 |
| 189 | CO2Me | 4-OH-3,5-dibromophenyl-C(Me)- (C6H3Br2O) | H | H | NO2 | H | Me | 413 |
| 190 | CO2H | N-methyl-N-phenylamino-C(Me)- (C7H8N) | H | Cl | Cl | H | Me | 544 |

TABLE 1-continued
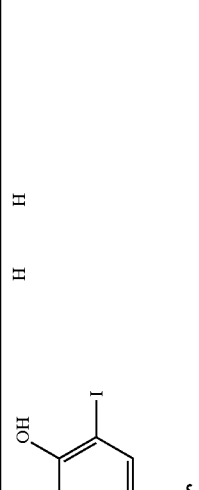
| No. | R₁ | R₂ | R₃ₐ | R₃ᵦ | R₃c | R₃d | R₄ | MS (M + 1) |
|---|---|---|---|---|---|---|---|---|
| 191 | CN | 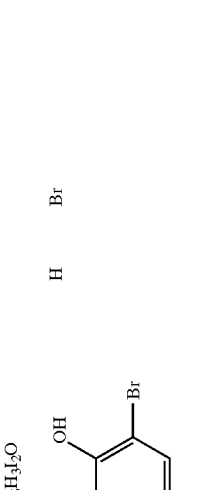 C₆H₃I₂O | H | H | H | H | Me | 565 |
| 192 | CO₂Me | 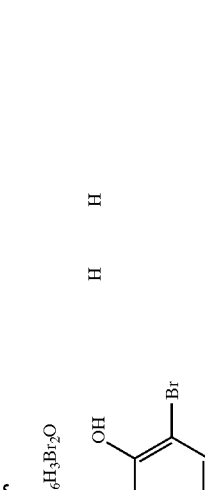 C₆H₃Br₂O | H | Br | H | H | Me | 606 (M + 23) |
| 193 | CO₂Me |  C₆H₃Br₂O | H | H | Br | H | Me | 584 |

TABLE 1-continued
Ia
| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 194 | CO$_2$Et | 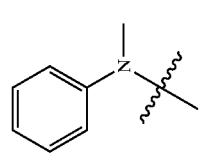 C$_7$H$_8$N | H | H | H | H | Me | 373 |
| 195 | CO$_2$Et | 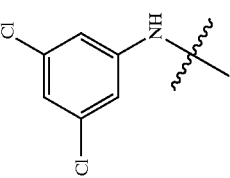 C$_6$H$_4$Cl$_2$N | H | H | H | H | Me | 427 |

TABLE 1-continued

Ia

| No. | R₁ | R₂ | R₃ₐ | R₃ᵦ | R₃c | R₃d | R₄ | MS (M+1) |
|---|---|---|---|---|---|---|---|---|
| 196 | CO₂Et | 3,5-dibromo-4-hydroxyphenyl-C(CH₃)- (C₆H₃Br₂O) | H | Cl | Cl | H | Me | 587 |
| 197 | CO₂Et | 3-bromophenyl-NH-C(CH₃)- (C₆H₅BrN) | H | H | H | H | Me | 437 |

TABLE 1-continued
Ia
| No. | R1 | R2 | R3a | R3b | R3c | R3d | R4 | MS (M + 1) |
|---|---|---|---|---|---|---|---|---|
| 198 | CO2Et | 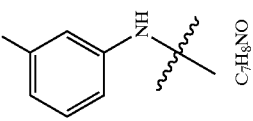 C7H8NO | H | H | H | H | Me | 389 |
| 199 | CO2Et | 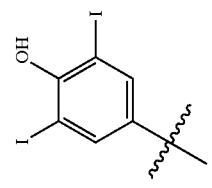 C6H3I2O | H | H | H | H | Me | 612 |

TABLE 1-continued

| No. | R$_1$ | R$_2$ | | R$_{3a}$ | R$_{3b}$ | R$_{3c}$ | R$_{3d}$ | R$_4$ | MS (M + 1) |
|---|---|---|---|---|---|---|---|---|---|
| 200 | CO$_2$Et | 3,5-difluorophenyl-C(Me) | C$_6$H$_3$F$_2$ | H | Cl | Cl | H | Me | 449 |
| 201 | CO$_2$Me | quinolin-4-yl-C(Me) | C$_9$H$_6$N | H | Cl | Cl | H | Me | 450 |
| 202 | CO$_2$Me | 4-(difluoromethoxy)phenyl-C(Me) | C$_7$H$_5$F$_2$O | H | Cl | Cl | H | Me | 465 |

TABLE 1-continued

Ia (structure shown with R1, R2, R3a-d, R4 substituents on fluorenone-pyridine core)

| No. | R₁ | R₂ | R₃ₐ | R₃ᵦ | R₃c | R₃d | R₄ | MS (M+1) |
|---|---|---|---|---|---|---|---|---|
| 203 | CO₂Me | 4-(OCHF₂)C₆H₄-C(Me)- (C₇H₅F₂O) | H | H | H | H | Me | 396 |
| 204 | CO₂Me | 3,5-diMe-C₆H₃-C(Me)- (C₈H₉); with C₄H₆NO₃ (HOOC-CH₂-CH₂-C(O)-NH-) | H | H | H | H | Me | 473 |
| 205 | CO₂Me | 4-NH₂-C₆H₄-C(Me)- (C₆H₆N) | H | H | H | H | Me | 345 |

TABLE 1-continued
Ia
| No. | R1 | R2 | | R3a | R3b | R3c | R3d | R4 | MS (M + 1) |
|---|---|---|---|---|---|---|---|---|---|
| 206 | CO2Me |  | C7H8N | H | H | H | H | Me | 359 |
| 207 | CO2Me |  | C6H4NO2 | H | Cl | Cl | H | Me | 444 |
| 208 | CO2Me |  | C7H4N | H | H | H | H | Me | 355 |

TABLE 1-continued

Ia

| No. | R₁ | R₂ | R₃ₐ | R₃ᵦ | R₃c | R₃d | R₄ | MS (M + 1) |
|---|---|---|---|---|---|---|---|---|
| 209 | CO₂H | naphthalen-1-yl (C₁₀H₇) | H | H | H | H | Me | 366 |
| 210 | CO₂Me | 3-nitrophenyl (C₆H₄NO₂) | H | Cl | Cl | H | Me | 444 |
| 211 | CO₂Me | 3-fluoro-4-methylphenyl (C₇H₆F) | H | Cl | Cl | H | Me | 430 |

TABLE 1-continued
| No. | R₁ | R₂ | R₃ₐ | R₃ᵦ | R₃c | R₃d | R₄ | MS (M+1) |
|---|---|---|---|---|---|---|---|---|
| 212 | CO₂Me | 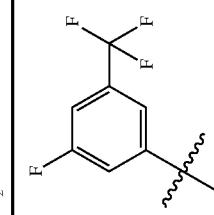 C₇H₃F₄ | H | H | H | H | Me | 416 |
| 213 | CO₂Me | 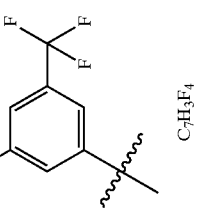 C₇H₆F | H | Cl | Cl | H | Me | 430 |
| 214 | CO₂Me | 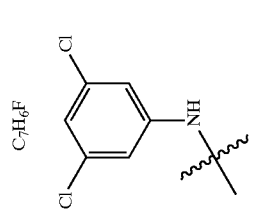 C₆H₄Cl₂N | H | H | H | H | Me | 413 |

TABLE 1-continued
Ia
| No. | R₁ | R₂ | | R₃ₐ | R₃ᵦ | R₃c | R₃d | R₄ | MS (M + 1) |
|---|---|---|---|---|---|---|---|---|---|
| 215 | CO₂Me | 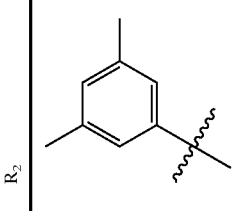 C₈H₉ | | H | OMe | OMe | H | Me | 418 |
| 216 | CO₂Me | 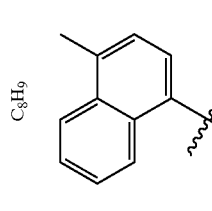 C₁₁H₉ | | H | OMe | OMe | H | Me | 454 |
| 217 | CO₂Me | 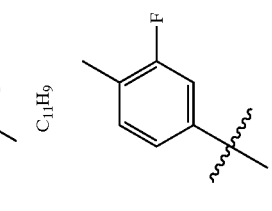 C₇H₆F | | H | H | H | H | Me | 362 |

TABLE 1-continued

| No. | R₁ | R₂ | R₃ₐ | R₃ᵦ | R₃꜀ | R₃d | R₄ | MS (M+1) |
|---|---|---|---|---|---|---|---|---|
| 218 | CO₂Me | 3,5-dimethylphenyl-C(CH₃)- (C₈H₉) | H | HOOC-CH₂CH₂-NH- (C₃H₆NO₂) | H | H | Me | 445 |
| 219 | CO₂Me | PhN(Me)-C(CH₃)- (C₇H₈N) | H | H | H | H | Me | 359 |
| 220 | CO₂Me | —NHPh | H | H | H | H | Me | 345 |

TABLE 1-continued

Ia

| No. | R₁ | R₂ | R₃ₐ | R₃ᵦ | R₃c | R₃d | R₄ | MS (M + 1) |
|---|---|---|---|---|---|---|---|---|
| 221 | CO₂Me | 3-Br-C₆H₄-NH-C(CH₃)₂- (C₆H₅BrN) | H | H | H | H | Me | 423 |
| 222 | CO₂Me | 2-Pyridyl | H | H | H | H | Me | 353 (M + 23) |
| 223 | CO₂Me | 3,5-Cl₂-C₆H₃-C(CH₃)₂- (C₆H₃Cl₂) | H | OMe | OMe | H | Me | 459 |

TABLE 1-continued

| No. | R₁ | R₂ | | R₃ₐ | R₃ᵦ | R₃c | R₃d | R₄ | MS (M+1) |
|---|---|---|---|---|---|---|---|---|---|
| 224 | CO₂Me | 3-F-5-CF₃-phenyl-C(CH₃)< | C₇H₃F₄ | H | Cl | Cl | H | Me | 485 |
| 225 | CO₂Me | 6-methylpyridin-2-yl-C(CH₃)< | C₆H₆N | H | H | H | H | Me | 345 |
| 226 | CO₂Me | 3-NO₂-phenyl-C(CH₃)< | C₆H₄NO₂ | H | H | NO₂ | H | Me | 420 |

TABLE 1-continued

| No. | R₁ | R₂ | R₃a | R₃b | R₃c | R₃d | R₄ | MS (M + 1) |
|---|---|---|---|---|---|---|---|---|
| 227 | CO₂Me | 4-NO₂-C₆H₄- (C₆H₄NO₂) | H | H | NO₂ | H | Me | 420 |
| 228 | CO₂Me | 3-Me-C₆H₄-NH- (C₇H₈N) | H | H | H | H | Me | 359 |

TABLE 1-continued

Ia (structure shown: tricyclic indeno-pyridinone with substituents R1, R2, R3a, R3b, R3c, R3d, R4)

| No. | R1 | R2 | R3a | R3b | R3c | R3d | R4 | MS (M+1) |
|---|---|---|---|---|---|---|---|---|
| 229 | CO2Me | 8-quinolinyl-NH-C(Me)2- (C9H7N2) | H | H | H | H | Me | 396 |
| 230 | CO2Me | (4-methylnaphth-1-yl)-C(Me)2- (C11H9) | H | OH | OH | H | Me | 426 |
| 231 | CO2Me | (3,5-dimethylphenyl)-C(Me)2- (C8H9) | H | H | F | H | Me | 376 |

TABLE 1-continued
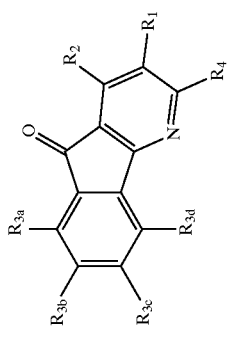
Ia
| No. | R₁ | R₂ | R₃ₐ | R₃ᵦ | R₃c | R₃d | R₄ | MS (M + 1) |
|---|---|---|---|---|---|---|---|---|
| 232 | CO₂Me | 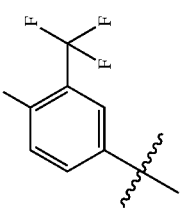 C₇H₃F₄ | H | H | NO₂ | H | Me | 461 |
| 233 | CO₂Me | 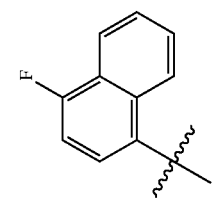 C₁₀H₆F | H | Cl | Cl | H | Me | 468 |

TABLE 1-continued
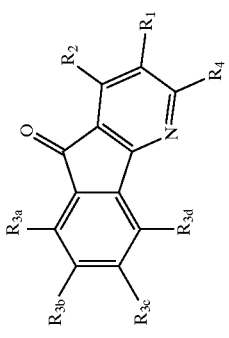
Ia
| No. | R1 | R2 | R3a | R3b | R3c | R3d | R4 | MS (M + 1) |
|---|---|---|---|---|---|---|---|---|
| 234 | CO2Me | 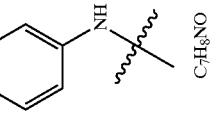 C8H10N | H | H | H | H | Me | 373 |
| 235 | CO2Me | 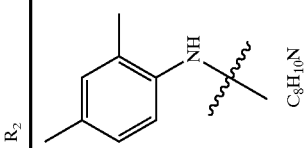 C7H8NO | H | H | H | H | Me | 375 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 236 | CO₂Me | C₁₀H₆F (4-fluoronaphthyl) | H | NO₂ | H | H | Me | 443 |
| 237 | CO₂Me | C₁₀H₆F (4-fluoronaphthyl) | H | H | NO₂ | H | Me | 443 |
| 238 | CO₂Me | C₁₀H₆F (4-fluoronaphthyl) | H | H | H | H | Me | 398 |

TABLE 1-continued
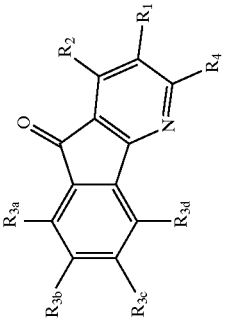
| No. | R₁ | R₂ | R₃ₐ | R₃ᵦ | R₃c | R₃d | R₄ | MS (M + 1) |
|---|---|---|---|---|---|---|---|---|
| 239 | CO₂Me | dimethylamino-naphthyl (C₁₂H₁₂N) | H | Cl | Cl | H | Me | 491 |
| 240 | CO₂Me | methyl-naphthyl (C₁₁H₉) | H | succinamide-CH (C₄H₆NO₃) | H | H | Me | 509 |
| 241 | CO₂Me | 3,5-dimethylphenyl (C₈H₉) | H | H | succinamide-CH (C₄H₆NO₃) | H | Me | 473 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 242 | CO₂Me | C₁₁H₉ (4-methylnaphthyl) | H | H | C₄H₆NO₃ (HOOC-CH₂CH₂-C(O)NH-) | H | Me | 509 |
| 243 | CO₂Me | C₄H₉ (isobutyl) | H | H | H | H | Me | 310 |
| 244 | CO₂Me | C₁₁H₉ (4-methylnaphthyl) | H | H | C₄H₇N₂O₃ (HONH-C(O)-CH₂CH₂-C(O)NH-) | H | Me | 524 |

TABLE 1-continued

Ia (structure shown with R1, R2, R3a, R3b, R3c, R3d, R4 substituents on a fluorenone-pyridine core)

| No. | R₁ | R₂ | R₃ₐ | R₃ᵦ | R₃c | R₃d | R₄ | MS (M + 1) |
|---|---|---|---|---|---|---|---|---|
| 245 | CO₂Me | 3,5-dimethylphenyl (C₈H₉) | H | H | -NH-C(O)-CH₂-CH₂-C(O)-NH-OH (C₄H₇N₂O₃) | H | Me | 488 |
| 246 | CO₂Me | pent-4-en-2-yl (C₄H₇) | H | H | H | H | Me | 308 |
| 247 | CO₂Me | i-Pr | H | H | H | H | Me | 296 |
| 248 | CO₂Me | Cyclohexyl | H | H | H | H | Me | 336 |
| 249 | CO₂Me | Me | H | H | H | H | Me | 268 |

TABLE 1-continued

| No. | R₁ | R₂ | R₃ₐ | R₃ᵦ | R₃꜀ | R₃d | R₄ | MS (M + 1) |
|---|---|---|---|---|---|---|---|---|
| 250 | CO₂Me | 3,5-dimethylphenyl-C(Me)₂- (C₈H₉) | H | H | -C(O)NHCH₂CH₂OH (C₄H₉N₂O₂) | H | Me | 474 |
| 251 | CO₂Me | 3,5-dimethylphenyl-C(Me)₂- (C₈H₉) | H | H | -C(O)CH₂CH₂CO₂H (C₅H₈NO₃) | H | Me | 487 |
| 252 | CO₂Me | N-Morpholino | H | H | H | H | Me | 339 |
| 253 | CO₂Me | cyclopentyl-NH-C(Me)₂- (C₅H₁₀N) | H | H | H | H | Me | 337 |

TABLE 1-continued
| No. | R1 | R2 | R3a | R3b | R3c | R3d | R4 | MS (M+1) |
|---|---|---|---|---|---|---|---|---|
| 254 | CO2Me | 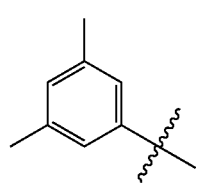 C8H9 | H | H | 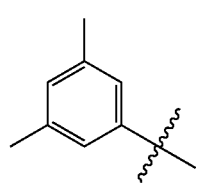 C5H11NO2 | H | Me | 488 |
| 255 | CO2Me |  C8H9 | H | H |  C4H9NO2 | H | Me | 474 |
| 256 | CO2Me |  C8H9 | H | H |  C4H7N2O | H | Me | 456 |

TABLE 1-continued
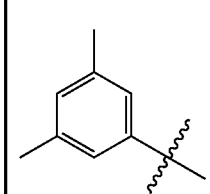
| No. | R₁ | R₂ | R₃ₐ | R₃ᵦ | R₃c | R₃d | R₄ | MS (M + 1) |
|---|---|---|---|---|---|---|---|---|
| 257 | CO₂Me | 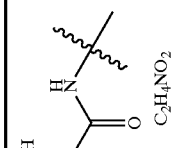 C₈H₉ | H | OH 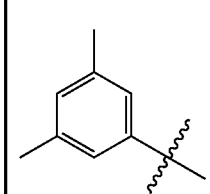 C₂H₄NO₂ | H | H | Me | 431 |
| 258 | CO₂Me | 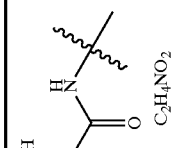 C₈H₉ | H | 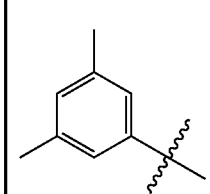 C₆H₁₁N₂O₂ | H | H | Me | 500 |
| 259 | CO₂Me | 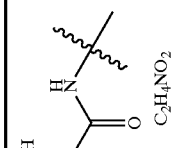 C₈H₉ | H |  C₆H₁₂N₃O | H | H | Me | 499 |

TABLE 1-continued
| No. | R₁ | R₂ | R₃ₐ | R₃ᵦ | R₃c | R₃d | R₄ | MS (M + 1) |
|---|---|---|---|---|---|---|---|---|
| 260 | CO₂Me | 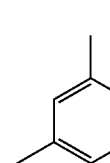 C₈H₉ | H | 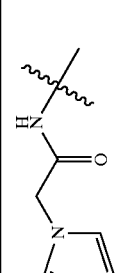 C₅H₆N₃O | H | H | Me | 481 |
| 261 | CO₂Me | 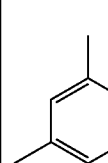 C₈H₉ | H | H | 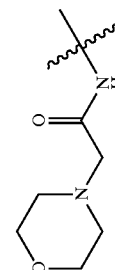 C₆H₁₁N₂O₂ | H | Me | 500 |
| 262 | CO₂Me | 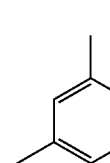 C₈H₉ | H | H | 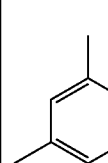 C₆H₁₂N₃O | H | Me | 499 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 263 | CO₂Me | 3,5-dimethylphenyl (C₈H₉) | H | H | -C(O)CH₂NHCH₂NO₂ (C₂H₄NO₂) | H | Me | 431 |
| 264 | CO₂Me | benzo[1,3]dioxol-5-yl (C₇H₅O₂) | H | H | H | H | NH₂ | 397 (M + 23) |
| 265 | CO₂Me | Ph | H | H | H | H | NH₂ | 353 (M + 23) |
| 266 | CO₂Me | 3,4-dimethoxyphenyl | H | H | H | H | NH₂ | 413 (M + 23) |

TABLE 1-continued
Ia
| No. | R₁ | R₂ | R₃ₐ | R₃♭ | R₃c | R₃d | R₄ | MS (M + 1) |
|---|---|---|---|---|---|---|---|---|
| 267 | CO₂Me | 2-Furyl | H | H | H | H | NH₂ | 321 |
| 268 | CO₂Me | 3-Furyl | H | H | H | H | NH₂ | 321 |
| 269 | CO₂Me | 2-Furyl | H | H | H | H | Me | 320 |
| 270 | CO₂Me | 2-Furyl | H | H | H | NH₂ | Me | 335 |
| 271 | CO₂Me | 2-Furyl | NHOH | H | H | H | Me | 351 |
| 272 | CO₂Et | 2-Furyl | H | Br | H | H | NH₂ | 335 |
| 273 | CO₂Et | 2-Furyl | H | H | Br | H | NH₂ | 413 |
| 274 | CO₂Et | 2-Furyl | H | H | Br | H | NH₂ | 413 |
| 275 | CO₂Et | 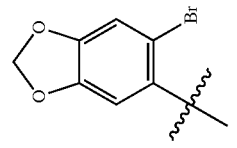 C₇H₄BrO₂ | H | H | H | H | Me | 467 |

TABLE 1-continued

| No. | R₁ | R₂ | R₃ₐ | R₃ᵦ | R₃c | R₃d | R₄ | MS (M+1) |
|---|---|---|---|---|---|---|---|---|
| 276 | CO₂Me | 3,5-dimethylphenyl-C(Me)₂– (C₈H₉) | H | H | imidazol-1-yl-CH₂-C(O)-NH– (C₅H₆N₃O) | H | Me | 481 |
| 277 | CO₂Me | 3,5-dimethylphenyl-C(Me)₂– (C₈H₉) | H | H | 2-oxopiperazin-1-yl (C₄H₇N₂O) | H | Me | 456 |
| 278 | CO₂Me | 3,5-dimethylphenyl-C(Me)₂– (C₈H₉) | H | H | HOOC-CH₂-CH₂-C(O)-NH– (C₄H₆NO₃) | H | Me | 473 |

TABLE 1-continued

| No. | R₁ | R₂ | R₃ₐ | R₃ᵦ | R₃c | R₃d | R₄ | MS (M + 1) |
|---|---|---|---|---|---|---|---|---|
| 279 | CO2Me | 3,5-dimethylphenyl-C(CH₃)₂- (C₈H₉) | H | N-methylpiperazinyl-CH₂-C(O)-NH- | H | H | Me | 513 |
| 280 | CO₂Me | 3,5-dimethylphenyl-C(CH₃)₂- (C₈H₉) | H | MeO₂C-CH(CH₃)-NH-CH₂-C(O)-NH- | H | H | Me | 516 |
| 281 | CO₂Me | 3,5-dimethylphenyl-C(CH₃)₂- (C₈H₉) | H | Me₂N-CH₂CH₂-NH-CH₂-C(O)-NH- | H | H | Me | 501 |

TABLE 1-continued

| No. | R$_1$ | R$_2$ | R$_{3a}$ | R$_{3b}$ | R$_{3c}$ | R$_{3d}$ | R$_4$ | MS (M + 1) |
|---|---|---|---|---|---|---|---|---|
| 282 | CO$_2$Me | 3,5-dimethylphenyl-C(Me)$_2$- (C$_8$H$_9$) | H | 3,4-dimethoxyphenyl-NH-C(O)-CH$_2$-NH- | H | H | Me | 566 |
| 283 | CO$_2$Me | 3,5-dimethylphenyl-C(Me)$_2$- (C$_8$H$_9$) | H | HO-(CH$_2$)$_3$-NH-C(O)-CH$_2$-NH- | H | H | Me | 488 |
| 284 | CO$_2$Me | 3,5-dimethylphenyl-C(Me)$_2$- (C$_8$H$_9$) | H | H | 4-acetylpiperazin-1-yl-CH$_2$-C(O)-NH- | H | Me | 541 |

III. Biological Assays and Activity

Ligand Binding Assay for Adenosine A2a Receptor

Ligand binding assay of adenosine A2a receptor was performed using plasma membrane of HEK293 cells containing human A2a adenosine receptor (PerkinElmer, RB-HA2a) and radioligand [$^3$H]CGS21680 (PerkinElmer, NET1021). Assay was set up in 96-well polypropylene plate in total volume of 200 mL by sequentially adding 20 mL1:20 diluted membrane, 130 mLassay buffer (50 mM Tris-HCl, pH7.4 10 mM $MgCl_2$, 1 mM EDTA) containing [3H] CGS21680, 50 mLdiluted compound (4×) or vehicle control in assay buffer. Nonspecific binding was determined by 80 mM NECA. Reaction was carried out at room temperature for 2 hours before filtering through 96-well GF/C filter plate presoaked in 50 mM Tris.HCl, pH7.4 containing 0.3% polyethylenimine. Plates were then washed 5 times with cold 50 mM Tris.HCl, pH7.4., dried and sealed at the bottom. Microscintillation fluid 30 ml was added to each well and the top sealed. Plates were counted on Packard Topcount for [$^3$H]. Data was analyzed in Microsoft Excel and GraphPad Prism programs. (Varani, K.; Gessi, S.; Dalpiaz, A.; Borea, P. A. British Journal of Pharmacology, 1996, 117, 1693)

Adenosine A2a Receptor Functional Assay

CHO-K1 cells overexpressing human adenosine A2a receptors and containing cAMP-inducible beta-galactosidase reporter gene were seeded at 40–50K/well into 96-well tissue culture plates and cultured for two days. On assay day, cells were washed once with 200 mL assay medium (F-12 nutrient mixture/0.1% BSA). For agonist assay, adenosine A2a receptor agonist NECA was subsequently added and cell incubated at 37 C., 5% $CO_2$ for 5 hrs before stopping reaction. In the case of antagonist assay, cells were incubated with antagonists for 5 minutes at R.T. followed by addition of 50 nM NECA. Cells were then incubated at 37C., 5% $CO_2$ for 5 hrs before stopping experiments by washing cells with PBS twice. 50 mL 1× lysis buffer (Promega, 5× stock solution, needs to be diluted to 1× before use) was added to each well and plates frozen at −20C. For b-galactosidase enzyme colormetric assay, plates were thawed out at room temperature and 50 mL 2× assay buffer (Promega) added to each well. Color was allowed to develop at 37C. for 1 hr. or until reasonable signal appeared. Reaction was then stopped with 150 mL 1M sodium carbonate. Plates were counted at 405 nm on Vmax Machine (Molecular Devices). Data was analyzed in Microsoft Excel and GraphPad Prism programs. (Chen, W. B.; Shields, T. S.; Cone, R. D. Analytical Biochemistry, 1995, 226, 349; Stiles, G. Journal of Biological Chemistry, 1992, 267, 6451)

Assay of Phosphodiesterase Activity

The assay of phosphodiesterase activity follows the homogeneous SPA (scintillation proximity assay) format under the principle that linear nucleotides preferentially bind yttrium silicate beads in the presence of zinc sulfate.

In this assay, the enzyme converts radioactively tagged cyclic nucleotides (reaction substrate) to linear nucleotides (reaction product) which are selectively captured via ion chelation on a scintillant-containing bead. Radiolabeled product bound to the bead surface results in energy transfer to the bead scintillant and generation of a quantifiable signal. Unbound radiolabel fails to achieve close proximity to the scintillant and therefore does not generate any signal.

Specifically, enzyme was diluted in PDE buffer (50 mM pH 7.4 Tris, 8.3 mM $MgCl_2$, 1.7 mM EGTA) with 0.1% ovalbumin such that the final signal:noise (enzyme:no enzyme) ratio is 5–10. Substrate (2,8-$^3$H-cAMP or 8-$^3$H-cGMP, purchased from Amersham Pharmacia) was diluted in PDE (4, 5, 7A) buffer to 1 nCi per $\mu l$ (or 1 $\mu$Ci/ml). For each test well, 48$\mu l$ of enzyme was mixed with 47$\mu l$ substrate and 5 $\mu l$ test compound (or DMSO) in a white Packard plate, followed by shaking to mix and incubation for 15 minutes at room temperature. A 50 $\mu l$ aliquot of evenly suspended yttrium silicate SPA beads in zinc sulfate was added to each well to terminate the reaction and capture the product. The plate was sealed using Topseal-S (Packard) sheets, and the beads were allowed to settle by gravity for 15–20 minutes prior to counting on a Packard TopCount scintillation counter using a $^3$H glass program with color quench correction. Output was in color quench-corrected dpm.

Test compounds were diluted in 100% DMSO to a concentration 20× final assay concentration. DMSO vehicle alone was added to uninhibited control wells. Inhibition (%) was calculated as follows:

Nonspecific binding (NSB)=the mean of CPM of the substrate+buffer+DMSO wells

Total Binding (TB)=the mean of the enzyme+substrate+DMSO wells $$\% \text{ Inhibition listed in Table 1} = \frac{(1 - (\text{Sample } CPM - NSB))}{TB - NSB} \times 100.$$

The $IC_{50}$ values were calculated using the Deltagraph 4-parameter curve-fitting program. The $IC_{50}$ and % Inhibition data on PDE 4, 5, and 7A are listed for the indicated compounds in Table 2 below.

TABLE 2
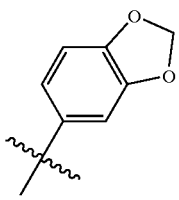
Ia
| No. | R₁ | R₂ | R₃ₐ | R₃ᵦ | R₃c | R₃d | R₄ | MS (M + 1) | IC₅₀(μM)/% inh.@μM PDE7A | PDE4 | PDE5 |
|---|---|---|---|---|---|---|---|---|---|---|---|
| 6 | CO₂H | 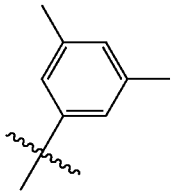<br>C₇H₅O₂ | H | H | H | H | Me | 360 | 45%@20 | 49%@5 | |
| 51 | CO₂Me | 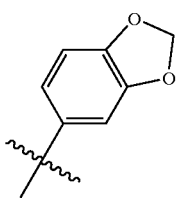<br>C₈H₉ | H | H | H | H | Me | 358 | 0.055 | 0.353 | 2.7 |
| 56 | CO₂Et | 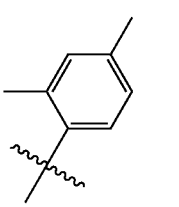<br>C₇H₅O₂ | H | H | NHAc | H | Me | 445 | 0.074 | 0.333 | 2.5 |
| 70 | CO₂Et | 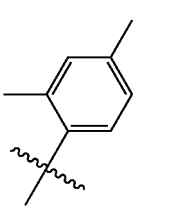<br>C₈H₉ | H | H | H | H | i-Pr | 400 | 2.11 | | |
| 73 | CO₂Me | 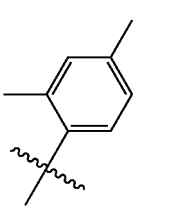<br>C₈H₉ | H | H | H | H | Et | 372 | 1.54 | | 0.998 |

TABLE 2-continued

Structure Ia: tricyclic indeno-pyridinone with substituents $R_{3a}$, $R_{3b}$, $R_{3c}$, $R_{3d}$ on the benzene ring, $R_1$, $R_2$ on the pyridine ring with ketone, and $R_4$ adjacent to N.

| No. | $R_1$ | $R_2$ | $R_{3a}$ | $R_{3b}$ | $R_{3c}$ | $R_{3d}$ | $R_4$ | MS (M+1) | PDE7A | PDE4 | PDE5 |
|---|---|---|---|---|---|---|---|---|---|---|---|
| 82 | $CO_2Me$ | 3,5-dimethylphenyl ($C_8H_9$) | H | $NH_2$ | H | H | Me | 373 | 0.021 | 0.204 | 1.11, 0.864 |
| 90 | $CO_2Me$ | 4-methylnaphthyl ($C_{11}H_9$) | H | $NH_2$ | H | H | Me | 409 | 0.005 | 0.237, 0.172 | 2.33 |
| 98 | CN | 4-methylnaphthyl ($C_{11}H_9$) | H | H | H | H | Me | 361 | 1.13 | | |
| 119 | CONHMe | 4-methylnaphthyl ($C_{11}H_9$) | H | H | H | H | Me | 393 | 0.658 | 41%@20 | |
| 133 | Ac | 3,5-dibromophenyl ($C_6H_3Br_2$) | H | H | H | H | Me | 472 | 1.54 | | |

TABLE 2-continued
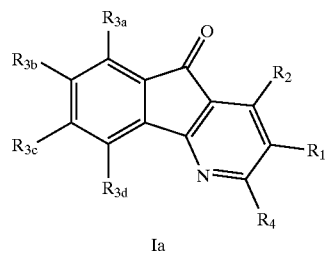
Ia
| No. | $R_1$ | $R_2$ | $R_{3a}$ | $R_{3b}$ | $R_{3c}$ | $R_{3d}$ | $R_4$ | MS (M + 1) | PDE7A | PDE4 | PDE5 |
|---|---|---|---|---|---|---|---|---|---|---|---|
| 134 | Ac | 3,5-dimethylphenyl ($C_8H_9$) | H | H | H | H | Me | 342 | 1.14 | | |
| 169 | $CO_2Me$ | 3,5-dibromo-4-hydroxyphenyl ($C_6H_3Br_2O$) | H | H | $NO_2$ | H | Me | 551 | 0.0053 | | 0.184 |
| 170 | $CO_2Me$ | 3,5-dibromo-4-hydroxyphenyl ($C_6H_3Br_2O$) | H | Cl | Cl | H | Me | 573 | 0.0087 | | 0.557 |
| 190 | $CO_2H$ | 3,5-dibromophenyl ($C_6H_3Br_2$) | H | Cl | Cl | H | Me | 544 | 5.9 | | |
| 191 | CN | 3,5-diiodo-4-hydroxyphenyl ($C_6H_3I_2O$) | H | H | H | H | Me | 565 | 0.593 | | |

TABLE 2-continued
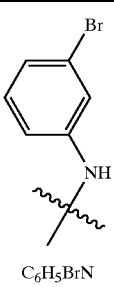
Ia
| No. | R₁ | R₂ | R₃ₐ | R₃ᵦ | R₃c | R₃d | R₄ | MS (M+1) | IC₅₀(μM)/% inh.@μM PDE7A | PDE4 | PDE5 |
|---|---|---|---|---|---|---|---|---|---|---|---|
| 197 | CO₂Et | 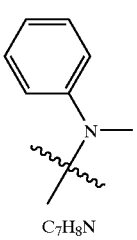 C₆H₅BrN | H | H | H | H | Me | 437 | 0.728 | 69%@5 | 0.362 |
| 219 | CO₂Me | 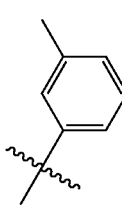 C₇H₈N | H | H | H | H | Me | 359 | 0.964 | 61%@5 | 1.1 |
| 220 | CO₂Me | —NHPh | H | H | H | H | Me | 345 | 0.084 | 1.8 | 0.637 |
| 241 | CO₂Me | 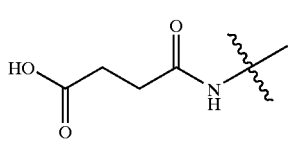 C₈H₉ | H | H | 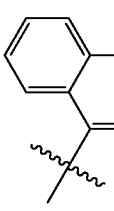 C₄H₆NO₃ | H | Me | 473 | 0.0035 | 0.954 | 0.183 |
| 242 | CO₂Me | 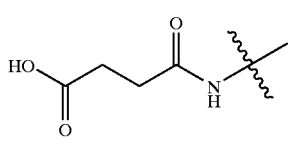 C₁₁H₉ | H | H | 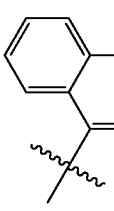 C₄H₆NO₃ | H | Me | 509 | 0.0038 | 0.782 | 0.141 |
| 243 | CO₂Me | 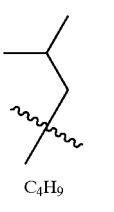 C₄H₉ | H | H | H | H | Me | 310 | 2.6 | | |

TABLE 2-continued
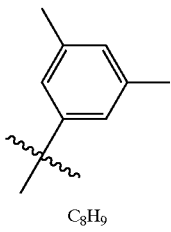
| No. | R₁ | R₂ | R₃ₐ | R₃ᵦ | R₃c | R₃d | R₄ | MS (M + 1) | PDE7A | PDE4 | PDE5 |
|---|---|---|---|---|---|---|---|---|---|---|---|
| 245 | $CO_2Me$ | C₈H₉ (3,5-dimethylphenyl) | H | H | 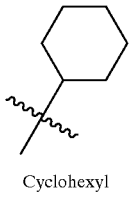 $C_4H_7N_2O_3$ | H | Me | 488 | 0.0053 | 0.875 | 0.185 |
| 248 | $CO_2Me$ | Cyclohexyl | H | H | H | H | Me | 336 | 0.783 | 0.171 | 0.649 |
| 250 | $CO_2Me$ | C₈H₉ (3,5-dimethylphenyl) | H | H | 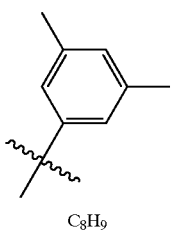 $C_4H_9N_2O_2$ | H | Me | 474 | 0.0074 | 0.684 | 2.4 |
| 251 | $CO_2Me$ | C₈H₉ (3,5-dimethylphenyl) | H | H | 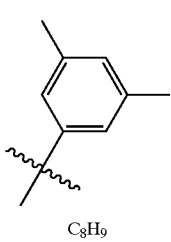 $C_5H_8NO_3$ | H | Me | 487 | 0.0054 | 0.754 | 0.26 |
| 253 | $CO_2Me$ | 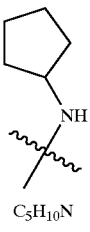 $C_5H_{10}N$ | H | H | H | H | Me | 337 | 0.905 | 0.85 | 0.303 |

TABLE 2-continued
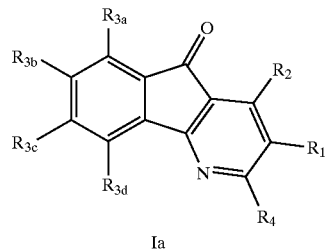
Ia
| No. | $R_1$ | $R_2$ | $R_{3a}$ | $R_{3b}$ | $R_{3c}$ | $R_{3d}$ | $R_4$ | MS (M + 1) | IC$_{50}$(μM)/% inh.@μM PDE7A | PDE4 | PDE5 |
|---|---|---|---|---|---|---|---|---|---|---|---|
| 254 | CO$_2$Me | C$_8$H$_9$ (3,5-dimethylphenyl) | H | H | C$_5$H$_{11}$N$_2$O$_2$ (HO-CH$_2$CH$_2$-N(Me)-CH$_2$-C(O)-NH-) | H | Me | 488 | 0.0067 | 0.664 | 0.765 |
| 261 | CO$_2$Me | C$_8$H$_9$ | H | H | C$_6$H$_{11}$N$_2$O$_2$ (morpholino-CH$_2$-C(O)-NH-) | H | Me | 500 | 0.0063 | 0.477 | 0.63 |
| 262 | CO$_2$Me | C$_8$H$_9$ | H | H | C$_6$H$_{12}$N$_3$O (piperazino-CH$_2$-C(O)-NH-) | H | Me | 499 | 0.008 | 0.702 | 3.7 |

TABLE 3
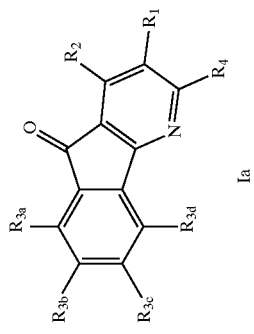
| No. | R₁ | R₂ | R₃ₐ | R₃ᵦ | R₃c | R₃d | R₄ | MS (M+1) | Ki(nM) A2a binding | A2a antagonist function | A1 binding |
|---|---|---|---|---|---|---|---|---|---|---|---|
| 14 | CO₂Et | 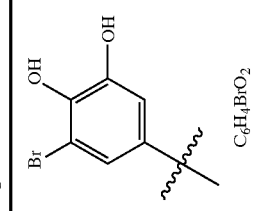  C₆H₄BrO₂ | H | H | H | H | Me | 454 | 451 | | |
| 22 | CO₂Et | 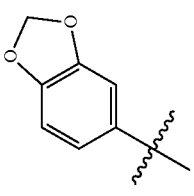  C₇H₅O₂ | H | H | H | H | NH₂ | 411 (M+23) | 70 | 253 | |

TABLE 3-continued

| No. | R₁ | R₂ | R₃ₐ | R₃ᵦ | R₃c | R₃d | R₄ | MS (M+1) | A2a binding | A2a antagonist function | A1 binding |
|---|---|---|---|---|---|---|---|---|---|---|---|
| 18 | CO₂Me | benzo[1,3]dioxol-5-yl-methyl (C₇H₅O₂) | H | H | H | H | Me | 374 | 159 | >1000 | 584 |
| 27 | CO₂Et | Ph | H | H | H | H | NH₂ | 345 | 42 | 36 | 554 |
| 23 | CO₂Et | benzo[1,3]dioxol-4-yl-methyl (C₇H₅O₂) | H | H | H | H | Me | 388 | 251 | | |

TABLE 3-continued

Structure Ia: tricyclic indeno-pyridinone core with substituents R1, R2, R3a, R3b, R3c, R3d, R4

| No. | R1 | R2 | R3a | R3b | R3c | R3d | R4 | MS (M + 1) | Ki(nM) A2a binding | A2a antagonist function | A1 binding |
|---|---|---|---|---|---|---|---|---|---|---|---|
| 275 | CO₂Et | 6-bromo-benzo[1,3]dioxol-5-yl (C₇H₄BrO₂) | H | H | H | H | Me | 467 | 263 | | |
| 41 | CO₂Et | furan-2-yl (C₄H₃O) | H | H | H | H | Me | 334 | 271 | | |
| 57 | CO₂Et | m-tolyl (C₇H₇) | H | H | H | H | Me | 358 | 400 | | |

TABLE 3-continued
Ia
| No. | R₁ | R₂ | R₃ₐ | R₃ᵦ | R₃c | R₃d | R₄ | MS (M+1) | A2a binding | A2a antagonist function | A1 binding |
|---|---|---|---|---|---|---|---|---|---|---|---|
| 67 | CO₂Me |  C₇H₇ | H | H | H | H | Me | 344 | 39 | 128 | 1853 |
| 66 | CO₂Me |  C₇H₇ | H | H | H | H | Me | 344 | 46 | 151 | 1591 |
| 85 | CO₂Me |  C₆H₄Br | H | H | H | H | Me | 431 (M+23) | 35 | >1000 | 5570 |
Ki(nM) column group spans A2a binding, A2a antagonist function, A1 binding.

TABLE 3-continued
Ia
| No. | R₁ | R₂ | R₃ₐ | R₃ᵦ | R₃c | R₃d | R₄ | MS (M+1) | Ki(nM) A2a binding | A2a antagonist function | A1 binding |
|---|---|---|---|---|---|---|---|---|---|---|---|
| 82 | CO₂Me | 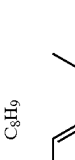 C₈H₉ | H | NH₂ | H | H | Me | 373 | 294 | | |
| 95 | CO₂Me | 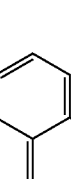 C₁₁H₉ | H | H | H | H | NH₂ | 395 | 286 | | |
| 135 | CO₂Me | 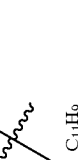 C₅H₄N | H | H | H | H | Me | 331 | 123 | | |

TABLE 3-continued
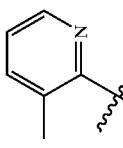
Ia
| No. | R1 | R2 | R3a | R3b | R3c | R3d | R4 | MS (M+1) | Ki(nM) A2a binding | A2a antagonist function | A1 binding |
|---|---|---|---|---|---|---|---|---|---|---|---|
| 130 | CO2Me | 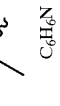 C6H6N | H | H | H | H | Me | 345 | 222 | | |
| 141 | CO2Me | 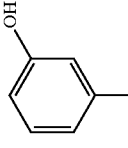 C6H5O | H | H | H | H | Me | 346 | 172 | | |

TABLE 3-continued

[Structure Ia: tricyclic indeno-pyridinone with substituents $R_1$, $R_2$, $R_{3a}$, $R_{3b}$, $R_{3c}$, $R_{3d}$, $R_4$]

| No. | $R_1$ | $R_2$ | $R_{3a}$ | $R_{3b}$ | $R_{3c}$ | $R_{3d}$ | $R_4$ | MS (M + 1) | Ki(nM) A2a binding | A2a antagonist function | A1 binding |
|---|---|---|---|---|---|---|---|---|---|---|---|
| 183 | $CO_2Et$ | 2,4-dimethylphenyl-NH-C(Me)<sub>2</sub>- ($C_8H_{10}N$) | H | H | H | H | Me | 387 | 191 | | |
| 208 | $CO_2Me$ | 3-cyanophenyl-C(Me)<sub>2</sub>- ($C_7H_4N$) | H | H | H | H | Me | 355 | 171 | | |

TABLE 3-continued

Ia

| No. | R₁ | R₂ | R₃ₐ | R₃ᵦ | R₃c | R₃d | R₄ | MS (M+1) | Ki(nM) A2a binding | Ki(nM) A2a antagonist function | Ki(nM) A1 binding |
|---|---|---|---|---|---|---|---|---|---|---|---|
| 197 | CO₂Et | 3-Br-C₆H₄-NH-C(CH₃)- (C₆H₅BrN) | H | H | H | H | Me | 437 | 148 | | |
| 217 | CO₂Me | 3-F-4-Me-C₆H₃-C(CH₃)- (C₇H₆F) | H | H | H | H | Me | 362 | 119 | | |

TABLE 3-continued

[Structure Ia shown]

| No. | R₁ | R₂ | R₃ₐ | R₃ᵦ | R₃c | R₃d | R₄ | MS (M+1) | A2a binding | A2a antagonist function | A1 binding |
|---|---|---|---|---|---|---|---|---|---|---|---|
| 221 | $CO_2Me$ | 3-Br-C₆H₄-NH-C(Me)₂- (C₆H₅BrN) | H | H | H | H | Me | 423 | 76 | 258 | 2180 |
| 222 | $CO_2Me$ | 2-Pyridyl | H | H | H | H | Me | 353 (M+23) | 237 | | |
| 198 | $CO_2Et$ | 3-MeO-C₆H₄-NH-C(Me)₂- (C₇H₈NO) | H | H | H | H | Me | 389 | 185 | | |

TABLE 3-continued
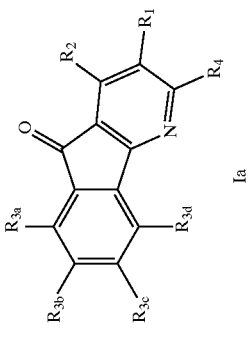
Ia
| No. | R1 | R2 | R3a | R3b | R3c | R3d | R4 | MS (M+1) | Ki(nM) A2a binding | A2a antagonist function | A1 binding |
|---|---|---|---|---|---|---|---|---|---|---|---|
| 199 | CO2Et |  C6H3I2O | H | H | H | H | Me | 612 | 301 | | |
| 279 | CO2Me | 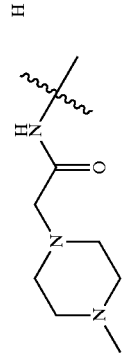 C8H9 | H | H | H | H | Me | 513 | 179 | | |

TABLE 3-continued

| No. | R1 | R2 | R3a | R3b | R3c | R3d | R4 | MS (M+1) | Ki(nM) A2a binding | A2a antagonist function | A1 binding |
|---|---|---|---|---|---|---|---|---|---|---|---|
| 261 | CO2Me | 3,5-dimethylphenyl-C(CH3)- (C8H9) | H | H | morpholinyl-CH2-C(O)-NH- (C6H11N2O2) | H | Me | 500 | 472 | | |
| 280 | CO2Me | 3,5-dimethylphenyl-C(CH3)- (C8H9) | H | H | MeO-C(O)-CH(CH3)-NH-C(O)-CH2-NH- | H | Me | 516 | 237 | | |

TABLE 3-continued
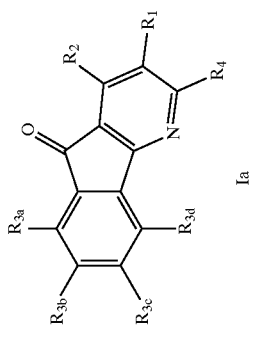
Ia
| No. | R₁ | R₂ | R₃ₐ | R₃ᵦ | R₃c | R₃d | R₄ | MS (M + 1) | Ki(nM) A2a binding | A2a antagonist function | A1 binding |
|---|---|---|---|---|---|---|---|---|---|---|---|
| 276 | CO₂Me | 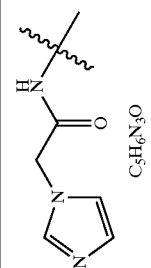 C₈H₉ | H | H | 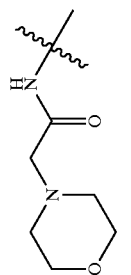 C₅H₆N₃O | H | Me | 481 | 304 | | |
| 258 | CO₂Me |  C₈H₉ | H | H |  C₆H₁₁N₂O₂ | H | Me | 500 | 211 | | |

TABLE 3-continued
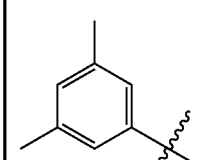
Ia
| No. | R₁ | R₂ | R₃ₐ | R₃ᵦ | R₃꜀ | R₃d | R₄ | MS (M + 1) | Ki(nM) A2a binding | A2a antagonist function | A1 binding |
|---|---|---|---|---|---|---|---|---|---|---|---|
| 281 | CO₂Me |  C₈H₉ | H |  | H | H | Me | 501 | 201 | | |
| 262 | CO₂Me |  C₈H₉ | H | H |  C₆H₁₂N₃O | H | Me | 499 | 332 | | |

TABLE 3-continued
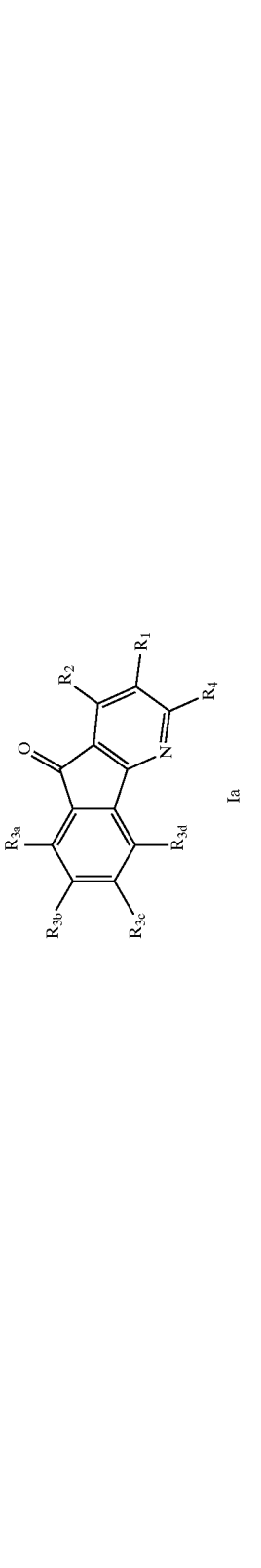
| No. | R₁ | R₂ | R₃ₐ | R₃ᵦ | R₃ᴄ | R₃d | R₄ | MS (M+1) | Ki(nM) A2a binding | A2a antagonist function | A1 binding |
|---|---|---|---|---|---|---|---|---|---|---|---|
| 184 | CO₂Et | NH-C₇H₈N | H | H | H | H | Me | 373 | 140 | | |
| 195 | CO₂Et | 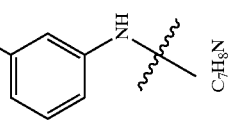C₆H₄Cl₂N | H | H | H | H | Me | 427 | 171 | | |

TABLE 3-continued

| No. | R₁ | R₂ | R₃ₐ | R₃ᵦ | R₃c | R₃d | R₄ | MS (M+1) | Ki(nM) A2a binding | A2a antagonist function | A1 binding |
|---|---|---|---|---|---|---|---|---|---|---|---|
| 260 | CO₂Me | C₈H₉ (3,5-dimethylphenyl) | H | C₅H₆N₃O (imidazolyl-CH₂-C(O)NH-) | H | H | Me | 481 | 163 | | |
| 263 | CO₂Me | C₈H₉ (3,5-dimethylphenyl) | H | H | C₂H₄NO₂ (HOCH₂-C(O)NH-) | H | Me | 431 | 480 | | |

TABLE 3-continued

| No. | R₁ | R₂ | R₃ₐ | R₃ᵦ | R₃c | R₃d | R₄ | MS (M+1) | A2a binding | A2a antagonist function | A1 binding |
|---|---|---|---|---|---|---|---|---|---|---|---|
| 245 | CO₂Me | 3,5-dimethylphenyl (C₈H₉) | H | H | C₄H₇N₂O₃ (—NH-C(=O)-CH₂CH₂-C(=O)-NHOH) | H | Me | 488 | 276 | | |
| 264 | CO₂Me | benzo[1,3]dioxol-5-yl (C₇H₅O₂) | H | H | H | H | NH₂ | 397 (M+23) | 342 | | |
| 265 | CO₂Me | Ph | H | H | H | H | NH₂ | 353 (M+23) | 50 | | |
| 267 | CO₂Me | 2-Furyl | H | H | H | H | NH₂ | 321 | <15 | | |
| 268 | CO₂Me | 3-Furyl | H | H | H | H | NH₂ | 321 | 21 | | |
| 269 | CO₂Me | 2-Furyl | H | H | H | H | Me | 320 | 192 | | |
| 270 | CO₂Me | 2-Furyl | H | H | H | NH₂ | Me | 335 | 303 | | |
| 271 | CO₂Me | 2-Furyl | NH₂ | H | H | H | Me | 351 | 276 | | |

TABLE 3-continued
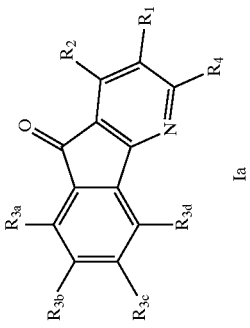
Ia
| No. | $R_1$ | $R_2$ | $R_{3a}$ | $R_{3b}$ | $R_{3c}$ | $R_{3d}$ | $R_4$ | MS (M + 1) | Ki(nM) A2a binding | A2a antagonist function | A1 binding |
|---|---|---|---|---|---|---|---|---|---|---|---|
| 272 | $CO_2Et$ | 2-Furyl | OH | H | H | H | $NH_2$ | 335 | <5 | | |
| 273 | $CO_2Et$ | 2-Furyl | H | Br | H | H | $NH_2$ | 413 | 279 | | |
| 274 | $CO_2Et$ | 2-Furyl | H | H | Br | H | $NH_2$ | 413 | 143 | | |

What is claimed is:

1. A compound having the structure

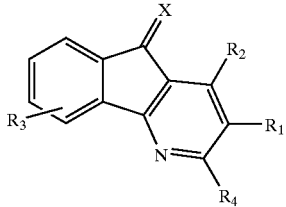

(a) $R_1$ is selected from the group consisting of:
  (i) —$COR_5$, wherein $R_5$ is selected from H, optionally substituted $C_{1-8}$ straight or branched chain alkyl, optionally substituted aryl and optionally substituted arylalkyl;
    wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl;
  (ii) $COOR_6$, wherein $R_6$ is selected from H, optionally substituted $C_{1-8}$ straight or branched chain alkyl, optionally substituted aryl and optionally substituted arylalkyl;
    wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl;
  (iii) cyano;
  (iv) a lactone or lactam formed with $R_4$;
  (v) —$CONR_7R_8$ wherein $R_7$ and $R_8$ are independently selected from H, $C_{1-8}$ straight or branched chain alkyl, $C_{3-7}$ cycloalkyl, trifluoromethyl, hydroxy, alkoxy, acyl, alkylcarbonyl, carboxyl, arylalkyl, and aryl;
    wherein the alkyl, cycloalkyl, alkoxy, acyl, alkylcarbonyl, carboxyl, arylalkyl, and aryl groups may be substituted with carboxyl, alkyl, aryl, substituted aryl, hydroxamic acid, sulfonamide, sulfonyl, hydroxy, thiol, alkoxy or arylalkyl;
  (vi) a carboxylic ester or carboxylic acid bioisostere;
(b) $R_2$ is selected from the group consisting of optionally substituted alkyl, optionally substituted aryl, optionally substituted heterocyclyl, wherein the heterocyclyl is 1,3-dioxolane or furan and optionally substituted $C_{3-7}$ cycloalkyl, or $R_2$ is

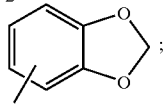;

(c) $R_3$ is from one to four groups independently selected from the group consisting of:
  (i) hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, and aryl;
  (ii) —$NR_{10}R_{11}$ wherein $R_{10}$ and $R_{11}$ are independently selected from H, $C_{1-8}$ straight or branched chain alkyl, arylalkyl, $C_{3-7}$ cycloalkyl, carboxyalkyl, or aryl;
  (iii) —$NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxyalkyl, $R_{30}R_{31}N(CH_2)_p$—, $R_{30}R_{31}NCO(CH_2)_p$—, aryl, and arylalkyl, wherein $R_{30}$ and $R_{31}$ are independently selected from H, OH, alkyl, and alkoxy, and p is an integer from 1–6, (d) $R_4$ is selected from the group consisting of (i) hydrogen, (ii) $C_{1-3}$ straight or branched chain alkyl, (iii) benzyl and (iv) —$NR_{13}R_{14}$, wherein $R_{13}$ and $R_{14}$ are independently selected from hydrogen and $C_{1-6}$ alkyl;
  wherein the $C_{1-3}$alkyl and benzyl groups are optionally substituted with one or more groups selected from $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, amino, $NR_{13}R_{14}$, and aryl; and
(e) X is selected from S and O;
with the proviso that when $R_4$ is isopropyl, then $R_3$ is not halogen, and that when $R_4$ is $C_{1-13}$ straight chain alkyl, then X is not O, $R_3$ is not H and $R_1$ is not COO-methyl and $R_2$ is not 2-methoxyphenyl, and the pharmaceutically acceptable salts, esters and pro-drug forms thereof.

2. The compound of claim 1, wherein $R_1$ is $COOR_6$, wherein $R_6$ is selected from H, optionally substituted $C_{1-8}$ straight or branched chain alkyl, optionally substituted aryl and optionally substituted arylalkyl.

3. The compound of claim 2, wherein $R_6$ is selected from H, or $C_{1-8}$ straight or branched chain alkyl which may be optionally substituted with a substituent selected from CN and hydroxy.

4. The compound of claim 1, wherein $R_2$ is optionally substituted aryl.

5. The compound of claim 4 wherein the aryl group is substituted with one to five members selected from the group consisting of halogen, alkyl, alkoxy, alkoxyphenyl, halo, triflouromethyl, trifluoro or difluoromethoxy, amino, alkylamino, hydroxy, cyano, and nitro.

6. The compound of claim 1 wherein, $R_2$ is optionally substituted furan, phenyl, or napthyl.

7. The compound of claim 1 wherein $R_3$ is selected from:
  (i) hydrogen, halo, $C_{1-8}$ straight or branched chain alkyl $C_{1-8}$ alkoxy, cyano, $C_{1-4}$ carboalkoxy, trifluoromethyl, $C_{1-8}$ alkylsulfonyl, halogen, nitro, and hydroxy;
  (ii) —$NR_{10}R_{11}$ wherein $R_{10}$ and $R_{11}$ are independently selected from H, $C_{1-8}$ straight or branched chain alkyl, aryl$C_{1-8}$alkyl, $C_{3-7}$ cycloalkyl, carboxy$C_{1-8}$alkyl, or aryl;
  (iii) —$NR_{12}COR_{13}$ wherein $R_{12}$ is selected from hydrogen or alkyl and $R_{13}$ is selected from hydrogen, alkyl, substituted alkyl, $C_{1-3}$alkoxyl, carboxy$C_{1-8}$alkyl, aryl, arylalkyl, $R_{30}R_{31}N(CH_2)_p$—, or $R_{30}R_{31}NCO(CH_2)_p$—, wherein $R_{30}$ and $R_{31}$ are independently selected from H, OH, alkyl, and alkoxy, and p is an integer from 1–6.

8. The compound of claim 7, wherein $R_3$ is selected from the group consisting of:

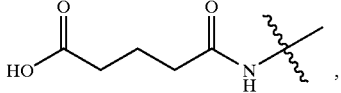

-continued

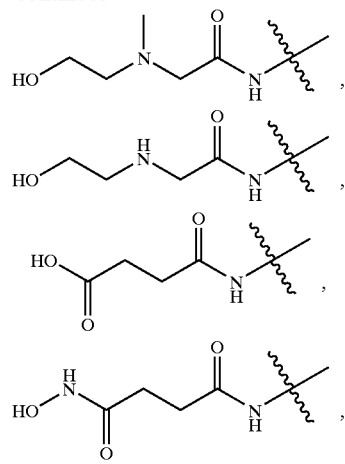

alkyl(CO)NH—, NH$_2$, and NO$_2$.

9. The compound of claim 1 wherein R$_4$ is selected from hydrogen, and C$_{1-3}$ straight or branched chain alkyl.

10. The compound of claim 9, wherein R$_4$ is selected from methyl and amino.

11. The compound of claim 1 wherein R$_1$ is COOR$_6$ and R$_2$ is selected from the group consisting of substituted phenyl, and substituted naphthyl.

12. The compound of claim 1 wherein R$_1$ is COOR$_6$ where R$_6$ is alkyl, R$_2$ is substituted phenyl or naphthyl, and R$_3$ is selected from the group consisting of H, nitro, amino, NHAc, halo, hydroxy, alkoxy, or a moiety of the formulae:

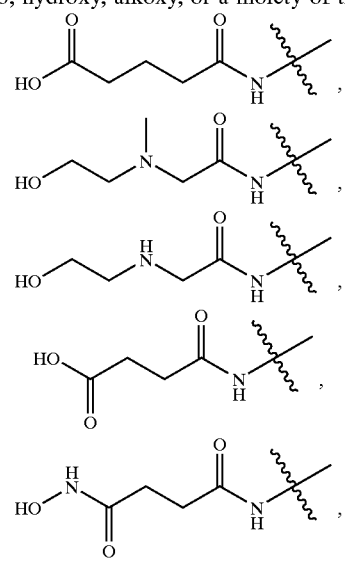

alkyl(CO)NH—, and R$_4$ is selected from hydrogen, C$_{1-3}$ straight or branched chain alkyl and amino and X is Oxygen.

13. A compound having the structure:

Formula I

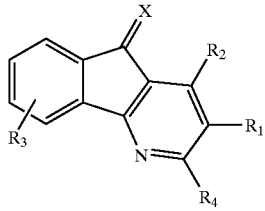

wherein
(a) R$_1$ is selected from the group consisting of:
(i) —COR$_5$, wherein R$_5$ is selected from H, optionally substituted C$_{1-8}$ straight or branched chain alkyl, optionally substituted aryl and optionally substituted arylalkyl;
wherein the substituents on the alkyl, aryl and arylalkyl group are selected from C$_{1-8}$ alkoxy, phenylacetyloxy, hydroxy, halogen, p-tosyloxy, mesyloxy, amino, cyano, carboalkoxy, or NR$_{20}$R$_{21}$ wherein R$_{20}$ and R$_{21}$ are independently selected from the group consisting of hydrogen, C$_{1-8}$ straight or branched chain alkyl, C$_{3-7}$ cycloalkyl, benzyl, or aryl;
(ii) COOR$_6$, wherein R$_6$ is selected from H, optionally substituted C$_{1-8}$ straight or branched chain alkyl, optionally substituted aryl and optionally substituted arylalkyl;
wherein the substituents on the alkyl, aryl and arylalkyl group are selected from C$_{1-8}$ alkoxy, phenylacetyloxy, hydroxy, halogen, p-tosyloxy, mesyloxy, amino, cyano, carboalkoxy, or NR$_{20}$R$_{21}$ wherein R$_{20}$ and R$_{21}$ are independently selected from the group consisting of hydrogen, C$_{1-8}$ straight or branched chain alkyl, C$_{3-7}$ cycloalkyl, benzyl, or aryl;
(iii) cyano;
(iv) a lactone or lactam formed with R$_4$;
(v) —CONR$_7$R$_8$ wherein R$_7$ and R$_8$ are independently selected from H, C$_{1-8}$ straight or branched chain alkyl, C$_{3-7}$ cycloalkyl, trifluoromethyl, hydroxy, alkoxy, acyl, alkylcarbonyl, carboxyl, arylalkyl, or aryl;
wherein the alkyl, cycloalkyl, alkoxy, acyl, alkylcarbonyl, carboxyl, arylalkyl, aryl, heteroaryl and heterocyclyl groups may be substituted with carboxyl, alkyl, aryl, substituted aryl, hydroxamic acid, sulfonamide, sulfonyl, hydroxy, thiol, alkoxy or arylalkyl;
(vi) a carboxylic ester or carboxylic acid;
(b) R$_2$ is —NR$_{15}$R$_{16}$ wherein R$_{15}$ and R$_{16}$ are independently selected from hydrogen, optionally substituted C$_{1-8}$ straight or branched chain alkyl, arylalkyl, C$_{3-7}$ cycloalkyl, aryl; with the proviso that when R$_2$ is NHR$_{16}$, R$_1$ is not —COOR$_6$ where R$_6$ is ethyl;
(c) R$_3$ is from one to four groups independently selected from the group consisting of:
(i) hydrogen, halo, C$_{1-8}$ straight or branched chain alkyl, arylalkyl, C$_{3-7}$ cycloalkyl, C$_{1-8}$ alkoxy, cyano, C$_{1-4}$ carboalkoxy, trifluoromethyl, C$_{1-8}$ alkylsulfonyl, halogen, nitro, hydroxy, trifluoromethoxy, C$_{1-8}$ carboxylate, or aryl;
(ii) —NR$_{10}$R$_{11}$ wherein R$_{10}$ and R$_{11}$ are independently selected from H, C$_{1-8}$ straight or branched chain alkyl, arylalkyl, C$_{3-7}$ cycloalkyl, carboxyalkyl, or aryl;

(iii) —NR$_{12}$COR$_{13}$ wherein R$_{12}$ is selected from hydrogen or alkyl and R$_{13}$ is selected from hydrogen, alkyl, substituted alkyl, C$_{1-3}$alkoxyl, carboxyalkyl, R$_{30}$R$_{31}$N(CH$_2$)$_p$—, R$_{30}$R$_{31}$NCO(CH$_2$)$_p$—, aryl, arylalkyl, heteroaryl and heterocyclyl or R$_{12}$ and R$_{13}$ taken together with the carbonyl form a carbonyl containing heterocyclyl group, wherein, R$_{30}$ and R$_{31}$ are independently selected from H, OH, alkyl, and alkoxy, and p is an integer from 1–6, wherein the alkyl group may be substituted with carboxyl, alkyl, aryl, substituted aryl, hydroxamic acid, sulfonamide, sulfonyl, hydroxy, thiol, alkoxy or arylalkyl;

(d) R$_4$ is selected from the group consisting of (i) hydrogen, (ii) C$_{1-3}$ straight or branched chain alkyl, (iii) benzyl and (iv) —NR$_{13}$R$_{14}$, wherein R$_{13}$ and R$_{14}$ are independently selected from hydrogen and C$_{1-6}$ alkyl; wherein the C$_{1-3}$alkyl and benzyl groups are optionally substituted with one or more groups selected from C$_{3-7}$ cycloalkyl, C$_{1-8}$ alkoxy, cyano, C$_{1-4}$ carboalkoxy, trifluoromethyl, C$_{1-8}$ alkylsulfonyl, halogen, nitro, hydroxy, trifluoromethoxy, C$_{1-8}$ carboxylate, amino, NR$_{13}$R$_{14}$, or aryl; and (e) X is selected from S and O;

provided that when R$_4$ is C$_{1-3}$ straight chain alkyl, then X is not O, R$_3$ is not H and R$_1$ is not COO-methyl and R$_2$ is not 2-methoxyphenyl, and the pharmaceutically acceptable salts, esters and pro-drug forms thereof.

14. The compound of claim 13, wherein R$_1$ is COOR$_6$ wherein R$_6$ is alkyl, R$_2$ is NR$_6$R$_7$, and R$_3$ is selected from the group consisting of

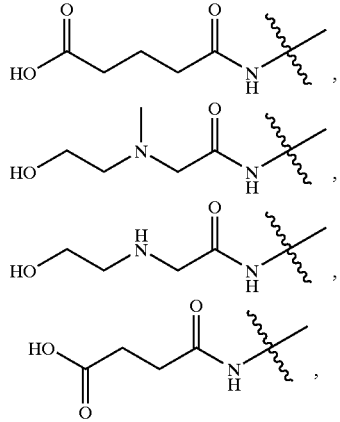

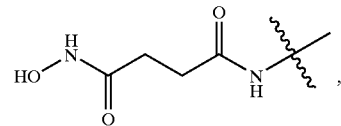

alkyl(CO)NH—, NH$_2$, NO$_2$, halogen, and hydrogen, and R$_4$ is selected from hydrogen, C$_{1-3}$ straight or branched chain alkyl and amino and X is Oxygen.

15. The compound of claim 1, which is 5H-indeno[1,2-b]pyridine-3-carboxylic acid, 4-phenyl-2-amino-5-oxo-, ethyl ester.

16. The compound of claim 1, which is 5H-indeno[1,2-b]pyridine-3-carboxylic acid, 4-(4-methylphenyl)-2-methyl-5-oxo-, methyl ester.

17. The compound of claim 1, which is 5H-indeno[1,2-b]pyridine-3-carboxylic acid, 4-(3-bromophenyl)-2-methyl-5-oxo-, methyl ester.

18. The compound of claim 1, which is 5H-indeno[1,2-b]pyridine-3-carboxylic acid, 4-(3-bromophenylamino)-2-methyl-5-oxo-, methyl ester.

19. The compound of claim 1, which is 5H-indeno[1,2-b]pyridine-3-carboxylic acid, 4-phenyl-2-amino-5-oxo-, methyl ester.

20. The compound of claim 1, which is 5H-indeno[1,2-b]pyridine-3-carboxylic acid, 4-(2-furyl)-2-amino-5-oxo-, methyl ester.

21. The compound of claim 1, which is 5H-indeno[1,2-b]pyridine-3-carboxylic acid, 4-(3-furyl)-2-amino-5-oxo-, methyl ester.

22. The compound of claim 1, which is 5H-indeno[1,2-b]pyridine-3-carboxylic acid, 4-(2-furyl)-2-amino-5-oxo-, ethyl ester.

23. A pharmaceutical composition comprising the compound of claim 1 and a pharmaceutically acceptable carrier.

24. A pharmaceutical composition comprising the compound of claim 13 and a pharmaceutically acceptable carrier.

* * * * *